United States Patent
Chen et al.

(10) Patent No.: US 7,374,779 B2
(45) Date of Patent: May 20, 2008

(54) PHARMACEUTICAL FORMULATIONS AND SYSTEMS FOR IMPROVED ABSORPTION AND MULTISTAGE RELEASE OF ACTIVE AGENTS

(75) Inventors: Feng-Jing Chen, Salt Lake City, UT (US); Srinivasan Venkateshwaran, Salt Lake City, UT (US); Steven L. Krill, Park City, UT (US); Mahesh V. Patel, Salt Lake City, UT (US)

(73) Assignee: Lipocine, Inc., Salt Lake City, UT (US)

( * ) Notice: Subject to any disclaimer, the term of this patent is extended or adjusted under 35 U.S.C. 154(b) by 1012 days.

(21) Appl. No.: 10/074,687

(22) Filed: Feb. 11, 2002

(65) Prior Publication Data

US 2003/0077297 A1 Apr. 24, 2003

Related U.S. Application Data

(60) Continuation-in-part of application No. 09/898,553, filed on Jul. 20, 2001, now Pat. No. 6,451,339, which is a continuation of application No. 09/258,654, filed on Feb. 26, 1999, now Pat. No. 6,294,192, application No. 10/074,687, which is a continuation-in-part of application No. 09/877,541, filed on Jun. 8, 2001, now Pat. No. 6,761,903, which is a continuation-in-part of application No. 09/345,615, filed on Jun. 30, 1999, now Pat. No. 6,297,985, application No. 10/074,687, which is a continuation-in-part of application No. 09/800,593, filed on Mar. 6, 2001, now Pat. No. 6,569,463, which is a division of application No. 09/447,690, filed on Nov. 23, 1999, now Pat. No. 6,248,363.

(51) Int. Cl.
*A61K 9/48* (2006.01)
*A61K 9/40* (2006.01)
*A61K 9/14* (2006.01)
*A61K 9/66* (2006.01)
*A61K 9/52* (2006.01)

(52) U.S. Cl. ............. 424/451; 424/455; 424/457; 424/489; 424/464

(58) Field of Classification Search ........... 424/464, 424/451, 450
See application file for complete search history.

(56) References Cited

U.S. PATENT DOCUMENTS 4,897,269 A * 1/1990 Mezei ................ 424/450

(Continued)

FOREIGN PATENT DOCUMENTS

EP 0184942 B1 8/1990

(Continued)

OTHER PUBLICATIONS

"Accutane," *Physicians Desk Reference*, 54th Edition, pp. 2610-2613 (2000).

(Continued)

*Primary Examiner*—Lakshmi S. Channavajjala
(74) *Attorney, Agent, or Firm*—Thorpe North & Western LLP

(57) ABSTRACT

The present invention pertains to pharmaceutical formulations and systems for delivery of active agents, wherein a first fraction of an active agent is suspended in a vehicle and a second fraction of active agent is solubilized in the vehicle, with the suspended fraction representing about 5 wt. % to about 80 wt. % of the active agent and the second fraction representing about 20 wt. % to about 95 wt. % of the active agent. One or more additional active agents, which may be fully solubilized, partially solubilized, or suspended, may also be present. The first and second fractions of the active agent may or may not have different release profiles. Generally, a significant fraction of the solubilized drug will release rapidly, providing for rapid onset, while the suspended drug may be formulated for delayed and/or sustained release.

86 Claims, 7 Drawing Sheets

U.S. PATENT DOCUMENTS

| | | |
|---|---|---|
| 5,091,187 A | 2/1992 | Haynes |
| 5,091,188 A | 2/1992 | Haynes |
| 5,145,684 A | 9/1992 | Liversidge et al. |
| 5,560,931 A | 10/1996 | Eickhoff et al. |
| 5,571,536 A | 11/1996 | Eickhoff et al. |
| 5,589,513 A * | 12/1996 | Magyar et al. ............. 514/654 |
| 5,629,021 A | 5/1997 | Wright |
| 5,922,355 A * | 7/1999 | Parikh et al. ............... 424/489 |
| 5,976,574 A | 11/1999 | Gordon |
| 6,086,376 A | 7/2000 | Moussa et al. |
| 6,096,338 A * | 8/2000 | Lacy et al. ................. 424/455 |
| 6,303,662 B1 * | 10/2001 | Nagahama et al. ......... 424/522 |
| 6,340,471 B1 | 1/2002 | Kershman et al. |
| 6,368,634 B1 | 4/2002 | Remon |
| 6,447,806 B1 * | 9/2002 | Gassmann et al. .......... 424/490 |

FOREIGN PATENT DOCUMENTS

| | | |
|---|---|---|
| GB | 2098865 A * | 12/1982 |
| WO | WO 00/25772 | 5/2000 |
| WO | WO 01/21154 | 3/2001 |

OTHER PUBLICATIONS

"Depo-Provera," *Physicians Desk Reference*, 54th Edition, pp. 2435-2437 (2000).

"Prometrium" *Physicians Desk Reference*, 54th Edition, pp. 3073-3076 (2000).

* cited by examiner

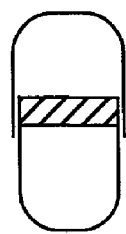 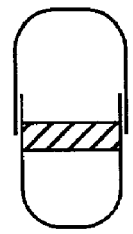
FIG. 3A  FIG. 3B
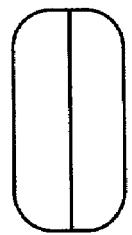 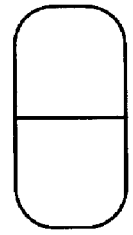
FIG. 4A  FIG. 4B
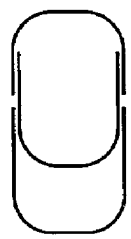 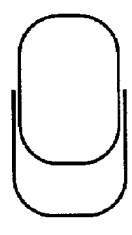 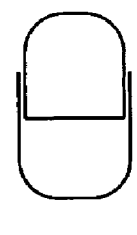
FIG. 5A  FIG. 5B  FIG. 5C

PHARMACEUTICAL FORMULATIONS AND SYSTEMS FOR IMPROVED ABSORPTION AND MULTISTAGE RELEASE OF ACTIVE AGENTS

CROSS-REFERENCE TO RELATED APPLICATIONS

This application is a continuation-in-part of U.S. patent application Ser. No. 09/898,553, filed Jul. 20, 2001 now U.S. Pat. No. 6,451,339, which is a continuation of U.S. patent application Ser. No. 09/258,654, filed Feb. 26, 1999, which issued on Sep. 25, 2001 as U.S. Pat. No. 6,294,192. This application is also a continuation-in-part of U.S. patent application Ser. No. 09/877,541, filed Jun. 8, 2001 now U.S. Pat. No. 6,761,903, which is a continuation-in-part of U.S. patent application Ser. No. 09/345,615, filed Jun. 30, 1999, issued on Jul. 31, 2001 as U.S. Pat. No. 6,297,985. This application is also a continuation-in-part of U.S. patent application Ser. No. 09/800,593, filed Mar. 6, 2001 now U.S. Pat. No. 6,569,463, which is a divisional of U.S. patent application Ser. No. 09/447,690, filed Nov. 23, 1999, issued on Jun. 19, 2001 as U.S. Pat. No. 6,248,363. The disclosures of the aforementioned patent applications are incorporated by reference herein.

TECHNICAL FIELD

The present invention relates generally to the field of drug delivery. More specifically, the invention relates to novel pharmaceutical compositions for administration of active agents to patients, wherein the compositions provide for multi-stage drug release. The invention additionally relates to processes for preparing the suspensions and methods of using the suspensions to administer an active agent to a patient. The invention has utility in the fields of pharmaceutical formulation, pharmacology, and medicine.

BACKGROUND

Those working in the fields of pharmaceutical formulation and drug delivery continue to be limited by a number of difficulties presented by different active agents. It has proved particularly problematic to provide therapeutically effective formulations for administration of drugs exhibiting low bioavailability and absorption. A well-designed formulation must, at a minimum, be capable of presenting a therapeutically effective amount of the active agent to the desired absorption site, in an absorbable form. Even this minimal functionality can be difficult to achieve, however, e.g., when delivery of a hydrophobic active agent requires interaction with aqueous physiological environments, such as gastric fluids and intestinal fluids.

A number of approaches to formulating active agents having low aqueous solubility are known. One well-known approach uses surfactant micelles to solubilize and transport the therapeutic agent. Micelles are agglomerates of colloidal dimensions formed by amphiphilic compounds under certain conditions. Micelles, and pharmaceutical compositions containing micelles, have been extensively studied and are described in detail in the literature; see, e.g., Remington: The Science and Practice of Pharmacy, Nineteenth Ed. (Easton, Pa.: Mack Publishing Company, 1995). In aqueous solution, micelles can incorporate hydrophobic therapeutic agents in the hydrocarbon core of the micelle, or entangled at various positions within the micelle walls. Although micellar formulations can solubilize a variety of hydrophobic therapeutic agents, the loading capacity of conventional micelle formulations is limited by the solubility of the therapeutic agent in the micelle surfactant. For many therapeutic agents, such solubility is too low to offer formulations that can deliver therapeutically effective doses.

Another conventional approach takes advantage of the increased solubility of hydrophobic therapeutic agents in lipids, particularly oils, i.e., triglycerides. However, traditional lipid-based formulations are generally limited by a low drug loading capacity, which in turn precludes delivery of a therapeutically effective amount of an active agent in a single unit dosage form, a significant drawback in terms of patient compliance. For example, the administration of vitamins typically requires multiple dosage units, as does the administration of a number of pharmacologically active agents (e.g., ritonavir and various other antiviral agents). Furthermore, the properties of oil-based formulations are determined by such factors as the size of the triglyceride/therapeutic agent colloidal particles and the presence or absence of surfactant additives. Although triglyceride-based pharmaceutical compositions are useful in solubilizing and delivering some hydrophobic therapeutic agents, such compositions are subject to a number of significant limitations and disadvantages. Emulsions are thermodynamically unstable, and colloidal emulsion particles will spontaneously agglomerate, eventually leading to complete phase separation. The tendency to agglomerate and phase separate presents problems of storage and handling, and increases the likelihood that pharmaceutical emulsions initially properly prepared will be in a less optimal, less effective, and poorly-characterized state upon ultimate administration to a patient. Uncharacterized degradation is particularly disadvantageous, since increased particle size slows the rate of transport of the colloidal particle and digestion of the oil component, and hence the rate and extent of absorption of the therapeutic agent. These problems lead to poorly-characterized and potentially harmful changes in the effective dosage received by the patient. Moreover, changes in colloidal emulsion particle size are also believed to render absorption more sensitive to and dependent upon conditions in the gastrointestinal tract, such as pH, enzyme activity, bile components, and stomach contents. Such uncertainty in the rate and extent of ultimate absorption of the therapeutic agent severely compromises the medical professional's ability to safely administer therapeutically effective dosages. A further disadvantage of triglyceride-containing compositions is the dependence of therapeutic agent absorption on the rate and extent of lipolysis. Although colloidal emulsion particles can transport hydrophobic therapeutic agents through the aqueous environment of the gastrointestinal tract, ultimately the triglyceride must be digested and the therapeutic agent must be released in order to be absorbed through the intestinal mucosa. The triglyceride carrier is emulsified by bile salts and hydrolyzed, primarily by pancreatic lipase. The rate and extent of lipolysis, however, are dependent upon several factors that are difficult to adequately control.

Hydrophilic active agents, however, also present formulation problems, and although readily dissolved in the gastrointestinal environment, simple dissolution is not sufficient to provide efficient bioabsorption of the therapeutic agent. Barriers to absorption are presented by the mucous layer, the intestinal epithelial cell membrane, and the junctional structure such as tight junctions between the epithelial cells. Due to the presence of the negatively charged mucosal layer, significant electrostatic binding or repulsion of charged molecules can be encountered. The epithelial cell membranes are composed of phospholipid bilayers in which proteins are embedded via the hydrophobic segments. These bilayers at the apical and/or basolateral cell surface represent very strong barriers for transport of hydrophilic substances, including peptides and proteins. Frequently, hydrophilic therapeutic agents are also subject to enzymatic attack and are degraded before they can be presented to the absorption site.

Much effort has been expended to develop methods of overcoming these absorption barriers, in order to enhance the bioavailability of hydrophilic active agents. For example, the enzymatic barrier can be attacked by administering enzyme inhibitors to prevent or at least lessen the extent of presystemic degradation in the gastrointestinal tract (see, e.g., Bernkop-Schnurch (1998), "The use of inhibitory agents to overcome the enzymatic barrier to perorally administered therapeutic peptides and proteins," *Journal of Controlled Release* 52:1-16). Other efforts have focused on, for example, the use of absorption promoters to enhance epithelial permeability (e.g., LeCluyse and Sutton (1997), "In vitro models for selection of development candidates. Permeability studies to define mechanisms of absorption enhancement," *Advanced Drug Delivery Reviews* 23:163-183). However, the effectiveness of absorption enhancers such as permeability enhancers or enzyme inhibitors depends upon the ability of a pharmaceutical carrier to effectively present the absorption enhancers and the hydrophilic therapeutic agent to the absorption site, and prior efforts have not provided carriers which can do so efficiently. Moreover, maintaining effective carrier concentrations at the epithelium is not easily controlled in vivo. Too little carrier, or carrier concentrations only briefly maintained, may be ineffective. Too much carrier, or carrier concentrations maintained for too long, may result in compromised safety.

Traditional pharmaceutical suspensions of drugs are primarily composed of an aqueous continuous phase with little or no solubilized fraction. However, there are a few non-aqueous compositions on the market, e.g., Prometrium® (Solvay), an encapsulated formulation of micronized progesterone for oral administration, Accutane® (Roche), an encapsulated formulation of isotretinoin (cis-retinoic acid, indicated for treatment of severe nodular acne), also for oral administration, and Depo Provera® (Pharmacia), an injectable medroxyprogesterone acetate suspension. These non-aqueous dispersions have a very small fraction of drug in the dissolved state, typically far less than 10% of the total drug in the formulation. Moreover, because these traditional compositions lack any therapeutically significant solubilized fraction of drug, they are incapable of either enhancing the rate and extent of absorption or rapidly providing a therapeutically effective blood level of drug. For many types of drugs, these are significant limitations.

Current sustained release dosage forms provide a longer duration of action; however, their therapeutic utility is limited by the failure to provide any rapid onset, in turn a result of slow dissolution, low solubility, and the lack of any significant fraction of predissolved drug. For many therapeutic indications, such as pain, there is a need for both rapid onset of action and a longer duration of action.

With fundamental limitations presenting such enormous challenges for those attempting to formulate effective drug delivery systems, more complex formulation aspects have largely been ignored. For example, it would be highly desirable to provide a drug delivery system that not only provides for enhanced bioavailability and absorption of an active agent, but also exhibits long-term chemical and physical stability, and that, furthermore, may be readily tailored during manufacture to provide any of a number of unique drug release profiles, e.g., immediate release combined with delayed and/or sustained release, pulsatile release, targeted release, and the like.

SUMMARY OF THE INVENTION

The present invention is addressed to the aforementioned need in the art, and provides pharmaceutical formulations and drug delivery systems exhibiting numerous advantages relative to prior formulations and systems, including, but not limited to, the following: (1) significantly enhanced rate and extent of absorption, substantially increasing the bioavailability of both hydrophilic and hydrophobic active agents; (2) as a result of (1), the capability of administering a therapeutically sufficient amount of drug using fewer dosage units than previously possible, without compromising pharmacokinetic/pharmacodynamic properties; (3) reduced interpatient variability; (4) reduced impact of food on drug absorption; and (5) the capability of providing any of a variety of drug release profiles, e.g., rapid onset coupled with rapid apparent elimination, and rapid onset coupled with a longer duration of action.

In one aspect of the invention, a pharmaceutical formulation is provided in which a first fraction of an active agent is suspended in a vehicle, and the remaining, second fraction of the active agent is solubilized in the vehicle. The first fraction of the active agent, i.e., the suspended fraction, is comprised of a plurality of solid particles and represents about 5 wt. % to about 80 wt. % of the total active agent in the formulation, such that the second fraction, i.e., the solubilized fraction, represents approximately 20 wt. % to about 95 wt. % of the total active agent. The vehicle is comprised of at least one compound selected from the group consisting of a hydrophilic surfactant, a lipophilic surfactant, a triglyceride and a solubilizer, and is preferably comprised of at least two such compounds. The solid particles representing the second fraction of the active agent, generally although not necessarily having a mean diameter in the range of about 0.1 μm to about 100 μm, may be suspended in particulate form, or they may associate so as to form one or more larger dosage units such as a granule, pellet, bead or tablet, which dosage unit or units are then suspended in the vehicle. Alternatively, the solid particles representing the second fraction of the active agent may be contained within a capsule, which is in turn suspended in the vehicle.

The first and second fractions of the active agent may or may not have different release profiles. Generally, however, a significant fraction of the solubilized drug will release rapidly, providing for rapid onset, while the suspended drug will be released from the formulation and/or absorbed somewhat more slowly. Accordingly, the formulation provides for "multistage release," meaning that not all of the active agent in the formulation is released at once. If a sufficiently substantial fraction of active agent is solubilized and the suspended fraction is not specifically formulated for delayed or extended release (e.g., with an enteric and/or sustained release coating), the release profile provided by the formulation as a whole will involve rapid onset as well as rapid apparent elimination. Alternatively, an overall release profile that involves rapid onset coupled with an extended release period and/or duration of action may be provided by formulating the suspended fraction of drug so as to have desired extended and/or delayed release characteristics.

In the aforementioned embodiment, the first and second fractions of the active agent may be physically segregated such that they are not in contact. In such a case, the formulation further includes a means for physically segregating the first and second fractions so as to prevent contact therebetween, which can be, by way of example, a vehicle-impermeable coating on the second fraction of active agent, i.e., a coating on the individual solid particles when the second fraction is in particulate form, a coating on the one or more larger dosage units when the solid particles are associated with each other to form such dosage units, e.g., granules, pellets, beads, or tablets, or a coating on a capsule when the solid particles of the second fraction are encapsulated and suspended in capsule form. As another example, the formulation may be housed within a dosage form such as a capsule, and the means for physically segregating the first and second fractions comprises a wall, a plug, or a septum dividing the dosage form into a first region that contains the first fraction and a second region that contains the second fraction.

In a further aspect of the invention, a method is provided for administering an active agent to a mammalian patient, generally although not necessarily a human patient, wherein the method involves administering an amount of the aforementioned formulation that is sufficient to deliver a therapeutically effective amount of the active agent to the patient. Preferably, the formulation is orally administered.

In another aspect of the invention, a pharmaceutical system is provided for administration of an active agent, wherein the system is comprised of an active agent and a vehicle as above, i.e., a vehicle comprising at least one compound selected from the group consisting of a hydrophilic surfactant, a lipophilic surfactant, a triglyceride and a solubilizer, wherein the relative amounts of the active agent and the vehicle are such that upon admixture thereof, a first fraction of the active agent becomes suspended in the vehicle, and a second fraction of the active agent becomes solubilized in the vehicle, wherein the second fraction represents about 20 wt. % to about 95 wt. % of the total active agent in the formulation.

In a related aspect of the invention, a method is provided for administering an active agent to a mammalian patient, generally although not necessarily a human patient, wherein the method involves administering to the patient a pharmaceutical system of a) a therapeutically effective amount of an active agent; and (b) a pharmaceutically acceptable vehicle comprising at least one compound selected from the group consisting of a hydrophilic surfactant, a lipophilic surfactant, a triglyceride and a solubilizer, wherein the relative amounts of the active agent and the vehicle are such that upon admixture thereof, a first fraction of the active agent is suspended in the vehicle, and a second fraction of the active agent is solubilized in the vehicle, wherein the second fraction represents about 20 wt. % to about 95 wt. % of the total active agent in the formulation. The active agent, the vehicle, and the at least one compound may be administered simultaneously, in a single formulation or in two or more formulations, or at least two of the active agent, the vehicle, and the at least one compound are not administered simultaneously, in which case they may or may not be housed in different dosage forms.

In contrast to prior formulations, the present invention provides a pharmaceutical suspension in which a significant fraction of the active agent, on the order of 20 wt. % to 95 wt. %, is solubilized in the vehicle. The vehicle is highly water-dispersible so that the solubilized fraction of the active agent can be dispersed and available for absorption immediately.

BRIEF DESCRIPTION OF THE DRAWINGS

FIGS. 3A and 3B schematically illustrate, in cross-sectional view, capsules having an internal septum dividing the capsule interior into two regions, one of which may contain solubilized drug and the other of which may contain suspended drug.

FIGS. 4A and 4B schematically illustrate, in cross-sectional view, one-piece capsules having an internal wall separating the capsule interior into two regions, one of which may contain solubilized drug and the other of which may contain suspended drug.

FIGS. 5A, 5B, and 5C schematically illustrate various ways that dosage forms can be prepared so that an outer capsule encapsulates and inner capsule, allowing one fraction of a formulation to be encapsulated in the inner capsule, and a second fraction of a formulation to be encapsulated in the outer capsule along with the sealed inner capsule.

DETAILED DESCRIPTION OF THE INVENTION

Figure 1:
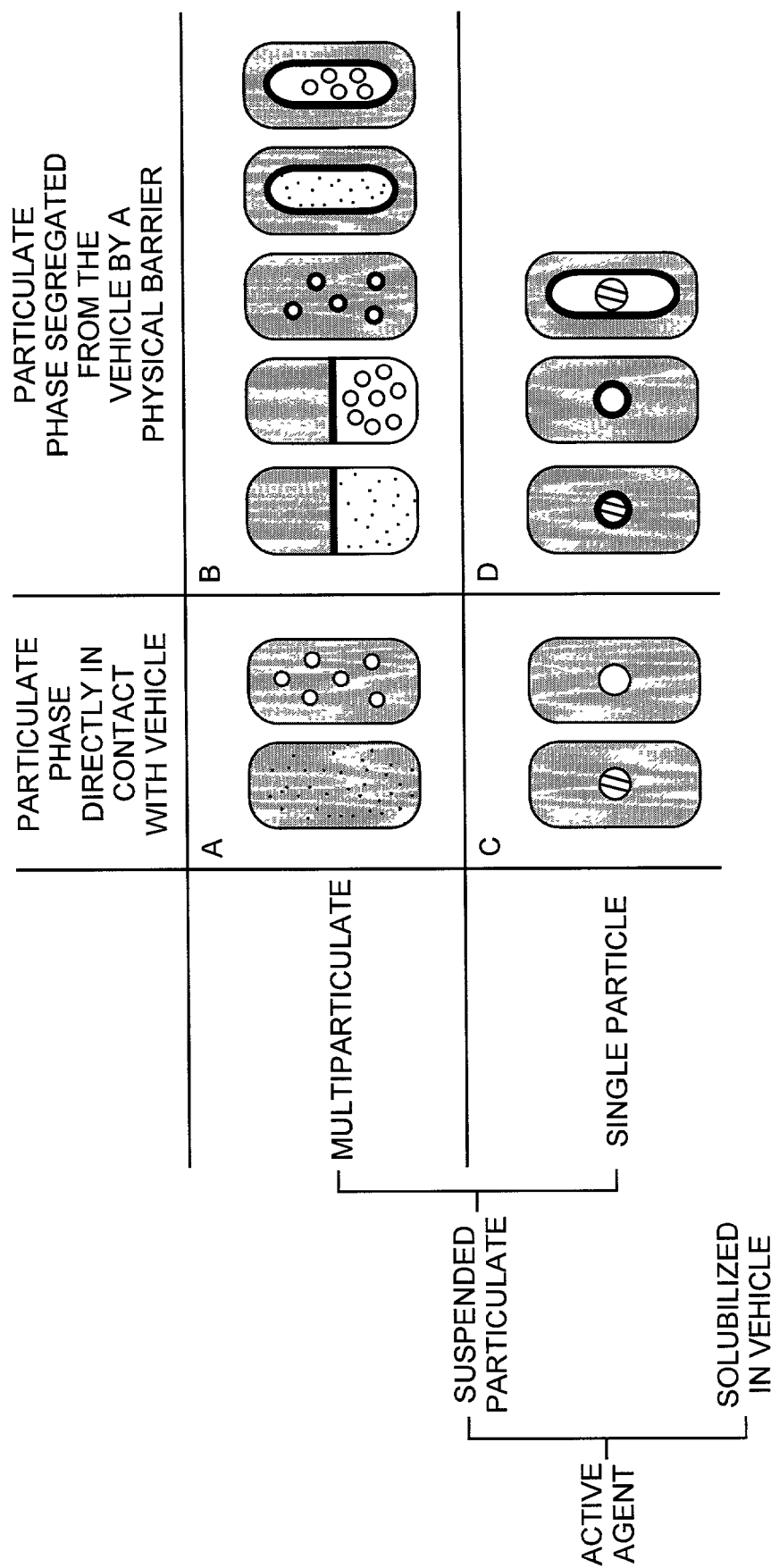
FIG. 1 schematically various embodiments of the invention wherein the pharmaceutical formulation, including both the suspended and solubilized fractions of active agent, are included in a single dosage form. The shaded regions represent the solubilized fractions of the formulation, wherein the active agent is solubilized in the vehicle.

I. Definitions and Overview:

It is to be understood that unless otherwise indicated, this invention is not limited to specific active agents, vehicles, excipients, dosage forms, or the like, as such may vary. It is also to be understood that the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "an active agent" includes a single active agent as well a two or more different active agents in combination, reference to "an excipient" includes mixtures of two or more excipients as well as a single excipient, and the like.

In describing and claiming the present invention, the following terminology will be used in accordance with the definitions set out below.

The terms "active agent," "pharmacologically active agent," and "drug" are used interchangeably herein to refer to any chemical compound, complex or composition that has a beneficial biological effect, preferably a therapeutic effect in the treatment of a disease or abnormal physiological condition. The terms also encompass pharmaceutically acceptable, pharmacologically active derivatives of those active agents specifically mentioned herein, including, but not limited to, salts, esters, amides, prodrugs, active metabolites, isomers, fragments, analogs, and the like. When the terms "active agent," "pharmacologically active agent" and "drug" are used, then, or when a particular active agent is specifically identified, it is to be understood that applicants intend to include the active agent per se as well as pharmaceutically acceptable, pharmacologically active salts, esters, amides, prodrugs, active metabolites, isomers, fragments, analogs, etc.

The term "dosage form" denotes any form of a pharmaceutical composition that contains an amount of active agent sufficient to achieve a therapeutic effect with a single administration. When the formulation is a tablet or capsule, the dosage form is usually one such tablet or capsule. The frequency of administration that will provide the most effective results in an efficient manner without overdosing will vary with the characteristics of the particular active agent, including both its pharmacological characteristics and its physical characteristics, such as hydrophilicity.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, "treating" a patient involves prevention of a particular disorder or adverse physiological event in a susceptible individual as well as treatment of a clinically symptomatic individual by inhibiting or causing regression of a disorder or disease.

By an "effective" amount or a "therapeutically effective amount" of an active agent is meant a nontoxic but sufficient amount of the agent to provide the desired effect. The amount of active agent that is "effective" will vary from subject to subject, depending on the age and general condition of the individual, the particular active agent or agents, and the like. Thus, it is not always possible to specify an exact "effective amount." However, an appropriate "effective" amount in any individual case may be determined by one of ordinary skill in the art using routine experimentation By "pharmaceutically acceptable," such as in the recitation of a "pharmaceutically acceptable excipient," or a "pharmaceutically acceptable additive," is meant a material that is not biologically or otherwise undesirable, i.e., the material may be incorporated into a pharmaceutical composition administered to a patient without causing any undesirable biological effects or interacting in a deleterious manner with any of the other components of the composition in which it is contained. "Pharmacologically active" (or simply "active"), as in a "pharmacologically active" derivative of an active agent, refers to a derivative having the same type of pharmacological activity as the parent compound and approximately equivalent in degree. When the term "pharmaceutically acceptable" is used to refer to a derivative (e.g., a salt) of an active agent, it is to be understood that the compound is pharmacologically active as well. When the term "pharmaceutically acceptable" is used to refer to an excipient, it implies that the excipient has met the required standards of toxicological and manufacturing testing or that it is on the Inactive Ingredient Guide prepared by the FDA.

The term "multistage release" refers to a drug-containing formulation or system wherein some of the drug is released according to a first release profile (e.g., immediate release), and the remainder of the drug is released according to one or more different release profiles (e.g., sustained release and/or delayed release as defined below). "Pulsatile release" is a form of multistage release wherein discrete pulses of drug are released over an extended time period.

The term "controlled release" refers to a drug-containing formulation or fraction thereof in which release of the drug is not immediate, i.e., with a "controlled release" formulation, administration does not result in immediate release of the drug into an absorption pool. The term is used interchangeably with "nonimmediate release" as defined in *Remington: The Science and Practice of Pharmacy*, Nineteenth Ed. (Easton, Pa.: Mack Publishing Company, 1995). In general, the term "controlled release" as used herein includes sustained release and delayed release formulations.

The term "sustained release" (synonymous with "extended release") is used in its conventional sense to refer to a drug formulation that provides for gradual release of a drug over an extended period of time, and that preferably, although not necessarily, results in substantially constant blood levels of a drug over an extended time period.

The term "delayed release" is used in its conventional sense to refer to a drug formulation in which there is a time delay provided between oral administration of a drug dosage form and the release of the drug therefrom. "Delayed release" may or may not involve gradual release of drug over an extended period of time, and thus may or may not be "sustained release." Preferred "delayed release" formulations are enterically coated compositions.

The term "polymer" as used herein refers to a molecule containing a plurality of covalently attached monomer units, and includes branched, dendrimeric and star polymers as well as linear polymers. The term also includes both homopolymers and copolymers, e.g., random copolymers, block copolymers and graft copolymers, as well as uncrosslinked polymers and slightly to moderately to substantially crosslinked polymers.

"Vehicles" refer to conventional pharmaceutically acceptable carrier materials suitable for drug administration, and include any such materials known in the art that are nontoxic and do not interact with other components of a pharmaceutical formulation or drug delivery system in a deleterious manner.

Accordingly, the invention pertains to a novel pharmaceutical formulation that provides for increased absorption and bioavailability of active agents, particularly active agents that are administered orally. In a first embodiment, the formulation is comprised of an active agent having a first fraction suspended in a vehicle, and the remaining, second fraction solubilized in the vehicle. The first fraction of the active agent, i.e., the suspended fraction, is comprised of a plurality of solid particles and represents about 5 wt. % to about 80 wt. % of the total active agent in the formulation.

The vehicle is comprised of at least one compound selected from the group consisting of a hydrophilic surfactant, a lipophilic surfactant, a triglyceride and a solubilizer. The individual components of the formulation are described in detail below.

II. The Active Agent:

The active agents that may be administered using the formulations, systems and methods of the invention are not limited, as the invention enables the effective delivery of a wide variety of active agents. Therefore, the active agent administered may be selected from any of the various classes of such agents including, but not limited to, analgesic agents, anesthetic agents, anti-anginal agents, antiarthritic agents, anti-arrhythmic agents, antiasthmatic agents, antibacterial agents, anti-BPH agents, anticancer agents, anticholinergic agents, anticoagulants, anticonvulsants, antidepressants, antidiabetic agents, antidiarrheals, anti-epileptic agents, antifungal agents, antigout agents, antihelminthic agents, antihistamines, antihypertensive agents, antiinflammatory agents, antimalarial agents, antimigraine agents, antimuscarinic agents, antinauseants, antineoplastic agents, anti-obesity agents, antiosteoporosis agents, antiparkinsonism agents, antiprotozoal agents, antipruritics, antipsychotic agents, antipyretics, antispasmodics, antithyroid agents, antitubercular agents, antiulcer agents, anti-urinary incontinence agents, antiviral agents, anxiolytics, appetite suppressants, attention deficit disorder (ADD) and attention deficit hyperactivity disorder (ADHD) drugs, calcium channel blockers, cardiac inotropic agents, beta-blockers, central nervous system stimulants, cognition enhancers, corticosteroids, COX-2 inhibitors, decongestants, diuretics, gastrointestinal agents, genetic materials, histamine receptor antagonists, hormonolytics, hypnotics, hypoglycemic agents, immunosuppressants, keratolytics, leukotriene inhibitors, lipid-regulating agents, macrolides, mitotic inhibitors, muscle relaxants, narcotic antagonists, neuroleptic agents, nicotine, nutritional oils, parasympatholytic agents, sedatives, sex hormones, sympathomimetic agents, tranquilizers, vasodilators, vitamins, and combinations thereof. Active agents that may be administered according to the invention also include nutrients, cosmeceuticals, diagnostic agents, and nutritional agents. Some agents, as will be appreciated by those of ordinary skill in the art, and as may be deduced from the discussion below, are encompassed by two or more of the aforementioned groups.

The active agent can be hydrophobic, amphiphilic, or hydrophilic. The intrinsic water solubility of those active agents referred to as "hydrophobic" herein, i.e., the aqueous solubility of the active agent in electronically neutral, non-ionized form, is generally less than 1% by weight, and typically less than 0.1% or 0.01% by weight. Hydrophilic and amphiphilic active agents herein (which, unless otherwise indicated, are collectively referred to herein as "hydrophilic" active agents) have apparent water solubilities of at least 0.1% by weight, and typically at least 1% by weight. Both hydrophobic active agents and hydrophilic active agents may be selected from any of the active agent classes enumerated earlier in this section.

Among the various active agent categories, preferred classes of active agents for administration using the present method and formulations are lipid regulating agents, sex hormones, anti-hypertensive agents, anti-diabetic agents, anti-viral agents (including protease inhibitors), peptidyl drugs, genetic materials, and combinations of any of the foregoing.

Lipid-regulating agents that are generally classified as hydrophobic include HMG CoA reductase inhibitors such as atorvastatin, simvastatin, fluvastatin, pravastatin, lovastatin, cerivastatin, rosuvastatin, and pitavastatin, as well as other lipid-lowering ("antihyperlipidemic") agents such as bezafibrate, beclobrate, binifibrate, ciprofibrate, clinofibrate, clofibrate, clofibric acid, ezetimibe, etofibrate, fenofibrate, fenofibric acid, gemfibrozil, nicofibrate, pirifibrate, probucol, ronifibrate, simfibrate, and theofibrate. A particularly preferred lipid-regulating agent that may be administered using the methods and formulations of the invention is fenofibrate.

Preferred sex hormones for administration using according to the invention include progestins (progestogens), estrogens, and combinations thereof. Progestins include acetoxypregnenolone, allylestrenol, anagestone acetate, chlormadinone acetate, cyproterone, cyproterone acetate, desogestrel, dihydrogesterone, dimethisterone, ethisterone (17α-ethinyltestosterone), ethynodiol diacetate, flurogestone acetate, gestadene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, progesterone, and trimgestone. Also included within this general class are estrogens, e.g.: estradiol (i.e., 1,3,5-estratriene-3,17β-diol, or "17β-estradiol") and its esters, including estradiol benzoate, valerate, cypionate, heptanoate, decanoate, acetate and diacetate; 17α-estradiol; ethinylestradiol (i.e., 17α-ethinylestradiol) and esters and ethers thereof, including ethinylestradiol 3-acetate and ethinylestradiol 3-benzoate; estriol and estriol succinate; polyestrol phosphate; estrone and its esters and derivatives, including estrone acetate, estrone sulfate, and piperazine estrone sulfate; quinestrol; mestranol; and conjugated equine estrogens. In many contexts, e.g., in female contraception and in hormone replacement therapy (HRT), a combination of a progestin and estrogen is used, e.g., progesterone and 17 β-estradiol. For HRT, an androgenic agent may be advantageously included as well. Androgenic agents for this purpose include, for example, dehydroepiandrosterone (DHEA; also termed "prasterone"), sodium dehydroepiandrosterone sulfate, 4-dihydrotestosterone (DHT; also termed "stanolone"), and testosterone, and pharmaceutically acceptable esters of testosterone and 4-dihydrotestosterone, typically esters formed from the hydroxyl group present at the C-17 position, including, but not limited to, the enanthate, propionate, cypionate, phenylacetate, acetate, isobutyrate, buciclate, heptanoate, decanoate, undecanoate, caprate and isocaprate esters.

Androgenic agents may also be administered for other purposes well known in the art. In addition to the androgenic agents enumerated above, other androgenic agents include, but are not limited to, androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, ethylestrenol, oxandrolone, nandrolone phenpropionate, nandrolone decanoate, nandrolone furylpropionate, nandrolone cyclohexane-propionate, nandrolone benzoate, nandrolone cyclohexanecarboxylate, stanozolol, dromostanolone, and dromostanolone propionate.

Antihypertensive agents include, without limitation, amlodipine, benazepril, benidipine, candesartan, captopril, carvedilol, darodipine, dilitazem, diazoxide, doxazosin, enalapril, epleronone, eposartan, felodipine, fenoldopam, fosinopril, guanabenz, iloprost, irbesartan, isradipine, lercardinipine, lisinopril, losartan, minoxidil, nebivolol, nicardipine, nifedipine, nimodipine, nisoldipine, omapatrilat, phenoxybenzamine, prazosin, quinapril, reserpine, semotiadil, sitaxsentan, terazosin, telmisartan, and valsartan.

Anti-diabetic agents include, by way of example, acetohexamide, chlorpropamide, ciglitazone, farglitazar, glibenclamide, gliclazide, glipizide, glucagon, glyburide, glymepiride, miglitol, pioglitazone, nateglinide, pimagedine, repaglinide, rosiglitazone, tolazamide, tolbutamide, triampterine, and troglitazone.

Antiviral agents that can be delivered using the present methods and dosage forms include the antiherpes agents acyclovir, famciclovir, foscarnet, ganciclovir, idoxuridine, sorivudine, trifluridine, valacyclovir, and vidarabine, and otherantiviral agents such as abacavir, amantadine, amprenavir, delviridine, didanosine, efavirenz, indinavir, interferon alpha, lamivudine, nelfinavir, nevirapine, ribavirin, rimantadine, ritonavir, saquinavir, stavudine, tipranavir, valganciclovir, zalcitabine, and zidovudine; and other antiviral agents such as abacavir, indinavir, interferon alpha, nelfinavir, ribavirin, rimantadine, tipranavir, ursodeoxycholic acid, and valganciclovir.

Peptidyl drugs include therapeutic peptides and proteins per se, whether naturally occurring, chemically synthesized, recombinantly produced, and/or produced by biochemical (e.g., enzymatic) fragmentation of larger molecules, and may contain the native sequence or an active fragment thereof. Specific peptidyl drugs include, without limitation, the peptidyl hormones activin, amylin, angiotensin, atrial natriuretic peptide (ANP), calcitonin, calcitonin gene-related peptide, calcitonin N-terminal flanking peptide, ciliary neurotrophic factor (CNTF), corticotropin (adrenocorticotropin hormone, ACTH), corticotropin-releasing factor (CRF or CRH), epidermal growth factor (EGF), follicle-stimulating hormone (FSH), gastrin, gastrin inhibitory peptide (GIP), gastrin-releasing peptide, gonadotropin-releasing factor (GnRF or GNRH), growth hormone releasing factor (GRF, GRH), human chorionic gonadotropin (hCH), inhibin A, inhibin B, insulin, luteinizing hormone (LH), luteinizing hormone-releasing hormone (LHRH), α-melanocyte-stimulating hormone, β-melanocyte-stimulating hormone, γ-melanocyte-stimulating hormone, melatonin, motilin, oxytocin (pitocin), pancreatic polypeptide, parathyroid hormone (PTH), placental lactogen, prolactin (PRL), prolactin-release inhibiting factor (PIF), prolactin-releasing factor (PRF), secretin, somatotropin (growth hormone, GH), somatostatin (SIF, growth hormone-release inhibiting factor, GIF), thyrotropin (thyroid-stimulating hormone, TSH), thyrotropin-releasing factor (TRH or TRF), thyroxine, vasoactive intestinal peptide (VIP),and vasopressin. Other peptidyl drugs are the cytokines, e.g., colony stimulating factor 4, heparin binding neurotrophic factor (HBNF), interferon-α, interferon α-2a, interferon α-2b, interferon α-n3, interferon-β, etc., interleukin-1, interleukin-2, interleukin-3, interleukin-4, interleukin-5, interleukin-6, etc., tumor necrosis factor, tumor necrosis factor-α, granuloycte colony-stimulating factor (G-CSF), granulocyte-macrophage colony-stimulating factor (GM-CSF), macrophage colony-stimulating factor, midkine (MD), and thymopoietin. Still other peptidyl drugs that can be advantageously delivered using the methodology and formulations of the present invention include endorphins (e.g., dermorphin, dynorphin, α-endorphin, β-endorphin, γ-endorphin, σ-endorphin, [Leu$^5$]enkephalin, [Met$^5$]enkephalin, substance P), kinins (e.g., bradykinin, potentiator B, bradykinin potentiator C, kallidin), LHRH analogues (e.g., buserelin, deslorelin, fertirelin, goserelin, histrelin, leuprolide, lutrelin, nafarelin, tryptorelin), and the coagulation factors, such as $\alpha_1$-antitrypsin, $\alpha_2$-macroglobulin, antithrombin III, factor I (fibrinogen), factor II (prothrombin), factor III (tissue prothrombin), factor V (proaccelerin), factor VII (proconvertin), factor VIII (antihemophilic globulin or AHG), factor IX (Christmas factor, plasma thromboplastin component or PTC), factor X (Stuart-Power factor), factor XI (plasma thromboplastin antecedent or PTA), factor XII (Hageman factor), heparin cofactor II, kallikrein, plasmin, plasminogen, prekallikrein, protein C, protein S, and thrombomodulin and combinations thereof.

Genetic material may also be delivered using the present methods and formulations, including, for example, nucleic acids, RNA, DNA, recombinant RNA, recombinant DNA, antisense RNA, antisense DNA, ribozymes, ribooligonucleotides, deoxyribonucleotides, antisense ribooligonucleotides, and antisense deoxyribooligonucleotides. Representative genes include those encoding for vascular endothelial growth factor, fibroblast growth factor, Bcl-2, cystic fibrosis transmembrane regulator, nerve growth factor, human growth factor, erythropoietin, tumor necrosis factor, and interleukin-2, as well as histocompatibility genes such as HLA-B7.

Other therapeutic agents that can be delivered using the present methods and formulations include the following representative compounds:

anti-inflammatory agents and non-opioid analgesics, such as aloxiprin, auranofin, azapropazone, azathioprine, benorylate, butorphenol, capsaicin, celecoxib, diclofenac, diflunisal, esonarimod, etodolac, fenbufen, fenoprofen calcium, flurbiprofen, ibuprofen, indomethacin, ketoprofen, ketorolac, leflunomide, meclofenamic acid, mefenamic acid, nabumetone, naproxen, novantrone, oxaprozin, oxyphenbutazone, parecoxib, phenylbutazone, piclamilast, piroxicam, rofecoxib, ropivacaine, sulindac, tetrahydrocannabinol, tramadol, tromethamine, valdecoxib, and ziconotide, as well as the urinary analgesics phenazopyridine and tolterodine;

anti-angina agents, such as mibefradil, refludan, nahnefene, carvedilol, cromafiban, lamifiban, fasudil, ranolazine, tedisamil, nisoldipine, and tizanidine;

antihelminthics, such as albendazole, bephenium hydroxynaphthoate, cambendazole, dichlorophen, ivermectin, mebendazole, oxamniquine, oxfendazole, oxantel embonate, praziquantel, pyrantel embonate and thiabendazole;

anti-arrhythmic agents, such as amiodarone, disopyramide, flecainide acetate and quinidine sulfate;

anti-asthma agents, such as zileuton, zafirlukast, terbutaline sulfate, montelukast, and albuterol;

anti-bacterial agents, such as alatrofloxacin, azithromycin, baclofen, benethamine penicillin, cinoxacin, ciprofloxacin, clarithromycin, clofazimine, cloxacillin, demeclocycline, dirithromycin, doxycycline, erythromycin, ethionamide, furazolidone, grepafloxacin, imipenem, levofloxacin, lorefloxacin, moxifloxacin, nalidixic acid, nitrofurantoin, norfloxacin, ofloxacin, rifampicin, rifabutine, rifapentine, sparfloxacin, spiramycin, sulphabenzamide, sulphadoxine, sulphamerazine, sulphacetamide, sulphadiazine, sulphafurazole, sulphamethoxazole, sulphapyridine, tetracycline, trimethoprim, trovafloxacin, and vancomycin;

anti-cancer agents and immunosuppressants, such as alitretinoin, aminoglutethimide, amsacrine, anastrozole, azathioprine, bexarotene, bicalutamide, biricodar, bisantrene, busulfan, camptothecin, candoxatril, capecitabine, cytarabine, chlorambucil, cyclosporin, dacarbazine, decitabine, ellipticine, estramustine, etoposide, gemcitabine, irinotecan, lasofoxifene, letrozole, lomustine, melphalan, mercaptopurine, methotrexate, mitomycin, mitotane, mitoxantrone, mofetil, mycophenolate, nebivolol, nilutamide, paclitaxel, palonosetron, procarbazine, ramipril, rubitecan, sirolimus, tacrolimus, tamoxifen, teniposide, testolactone, thalidomide, tirapazamine, topotecan, toremifene citrate, vitamin A, vitamin A derivatives, and zacopride;

anti-coagulants and other agents for preventing and treating stroke, such as cilostazol, citicoline, clopidogrel, cromafiban, dexanabinol, dicumarol, dipyridamole, nicoumalone, oprelvekin, perindopril erbumine, phenindione, ramipril, repinotan, ticlopidine, tirofiban, and heparin, including heparin salts formed with organic or inorganic bases, and low molecular weight heparin, i.e., heparin fragments generally having a weight average molecular weight in the range of about 1000 to about 10,000 D and exemplified by enoxaparin, dalteparin, danaproid, gammaparin, nadroparin, ardeparin, tinzaparin, certoparin, and reviparin;

anti-diabetics, such as acetohexamide, chlorpropamide, farglitazar, glibenclamide, gliclazide, glipizide, glimepiride, miglitol, nateglinide, pimagedine, pioglitazone, repaglinide, rosiglitazone, tolazamide, tolbutamide, troglitazone, and voglibose;

anti-epileptics, such as beclamide, carbamazepine, clonazepam, ethotoin, felbamate, fosphenytoin, lamotrigine, methoin, methsuximide, methylphenobarbitone, oxcarbazepine, paramethadione, phenacemide, phenobarbitone, phenytoin, phensuximide, primidone, sulthiame, tiagabine, topiramate, valproic acid, and vigabatrin;

anti-fungal agents, such as amphotericin, butenafine, butoconazole nitrate, clotrimazole, econazole nitrate, fluconazole, flucytosine, griseofulvin, itraconazole, ketoconazole, miconazole, natamycin, nystatin, sulconazole nitrate, oxiconazole, terbinafine, terconazole, tioconazole and undecenoic acid;

anti-gout agents, such as allopurinol, probenecid and sulphin-pyrazone;

antihistamines and allergy medications, such as acrivastine, astemizole, chlorpheniramine, cinnarizine, cetirizine, clemastine, cyclizine, cyproheptadine, desloratadine, dexchlorpheniramine, dimenhydrinate, diphenhydramine, epinastine, fexofenadine, flunarizine, loratadine, meclizine, mizolastine, oxatomide, and terfenadine;

anti-malarials, such as amodiaquine, chloroquine, chlorproguanil, halofantrine, mefloquine, proguanil, pyrimethamine and quinine sulfate;

agents for treating headaches, including anti-migraine agents, such as almotriptan, butorphanol, dihydroergotamine, dihydroergotamine mesylate, eletriptan, ergotamine, frovatriptan, methysergide, naratriptan, pizotyline, rizatriptan, sumatriptan, tonaberstat, and zolmitriptan;

anti-muscarinic agents, such as atropine, benzhexol, biperiden, ethopropazine, hyoscyamine, mepenzolate bromide, oxyphencyclimine, scopolamine, and tropicamide;

anti-protozoal agents, such as atovaquone, benznidazole, clioquinol, decoquinate, diiodohydroxyquinoline, diloxanide furoate, dinitolmide, furazolidone, metronidazole, nimorazole, nitrofirazone, ornidazole and tinidazole;

anti-thyroid agents, such as carbimazole, paricalcitol, and propylthiouracil;

anti-tussives, such as benzonatate;

anxiolytics, sedatives, and hypnotics, such as alprazolam, amylobarbitone, barbitone, bentazepam, bromazepam, bromperidol, brotizolam, butobarbitone, carbromal, chlordiazepoxide, chlormethiazole, chlorpromazine, chlorprothixene, clonazepam, clobazam, clotiazepam, clozapine, dexmethylphenidate (d-threo-methylphenidate) diazepam, droperidol, ethinamate, flunanisone, flunitrazepam, triflupromazine, flupenthixol decanoate, fluphenazine, flurazepam, gabapentin, gaboxadol, γ-hydroxybutyrate, haloperidol, lamotrigine, lorazepam, lormetazepam, medazepam, meprobamate, mesoridazine, methaqualone, methylphenidate, midazolam, modafinil, molindone, nitrazepam, olanzapine, oxazepam, pentobarbitone, perphenazine pimozide, pregabalin, prochlorperazine, pseudoephedrine, quetiapine, rispiridone, sertindole, siramesine, sulpiride, sunepitron, temazepam, thioridazine, triazolam, zaleplon, zolpidem, and zopiclone;

appetite suppressants, anti-obesity drugs and drugs for treatment of eating disorders, such as amphetamine, bromocriptine, dextroamphetamine, diethylpropion, lintitript, mazindol, methamphetamine, orlistat, phentermine, and topiramate;

cardiovascular drugs, including: angiotensin converting enzyme (ACE) inhibitors such as enalapril, ramipril, perindopril erbumine, 1-carboxymethyl-3-1-carboxy-3-phenyl-(1S)-propylamino-2,3,4,5-tetrahydro-1H-(3S)-1-benzazepine-2-one, 3-(5-amino-1-carboxy-1S-pentyl)amino-2,3,4,5-tetrahydro-2-oxo-3S-1H-1-benzazepine-1acetic acid or 3-(1-ethoxycarbonyl-3-phenyl-(1S)-propylamino)-2,3,4,5-tetrahydro-2-oxo-(3S)-benzazepi acid monohydrochloride; cardiac glycosides and cardiac inotropes such as amrinone, digoxin, digitoxin, enoximone, lanatoside C, medigoxin, and milrinone; calcium channel blockers such as verapamil, nifedipine, nicardipene, felodipine, isradipine, nimodipine, amlodipine and diltiazem; beta-blockers such as acebutolol, alprenolol, atenolol, labetalol, metoprolol, nadolol, oxyprenolol, pindolol, propafenone, propranolol, esmolol, sotalol, timolol, and acebutolol; antiarrhythmics such as moricizine, dofetilide, ibutilide, nesiritide, procainamide, quinidine, disopyramide, lidocaine, phenytoin, tocainide, mexiletine, flecainide, encainide, bretylium and amiodarone; cardioprotective agents such as dexrazoxane and leucovorin; vasodilators such as nitroglycerin; diuretic agents such as azetazolamide, amiloride, bendroflumethiazide, bumetanide, chlorothiazide, chlorthalidone, ethacrynic acid, furosemide, hydrochlorothiazide, metolazone, nesiritide, spironolactone, and triamterine; and miscellaneous cardiovascular drugs such as monteplase and corlopam;

corticosteroids, such as beclomethasone, betamethasone, budesonide, cortisone, desoxymethasone, dexamethasone, fludrocortisone, flunisolide, fluocortolone, fluticasone propionate, hydrocortisone, methylprednisolone, prednisolone, prednisone and triamcinolone;

erectile dysfunction drugs, such as apomorphine, phentolamine, and vardenafil;

gastrointestinal agents, such as alosetron, bisacodyl, cilansetron, cimetidine, cisapride, diphenoxylate, domperidone, esomeprazole, famotidine, granisetron, lansoprazole, loperamide, mesalazine, nizatidine, omeprazole, ondansetron, prantoprazole, rabeprazole sodium, ranitidine, risperidone, sulphasalazine, and tegaserod;

keratolytics, such as such as acetretin, calcipotriene, calcifediol, calcitriol, cholecalciferol, ergocalciferol, etretinate, retinoids, targretin, and tazarotene;

lipid regulating agents, such as atorvastatin, bezafibrate, cerivastatin, ciprofibrate, clofibrate, ezetimibe, fenofibrate, fluvastatin, gemfibrozil, pitavastatin, pravastatin, probucol, rosuvastatin, and simvastatin;

muscle relaxants, such as cyclobenzaprine, dantrolene sodium and tizanidine HCl;

agents to treat neurodegenerative diseases, including active agents for treating Alzheimer's disease such as akatinol, donezepil, donepezil hydrochloride, dronabinol, galantamine, neotrofin, rasagiline, physostigmine, physostigmine salicylate, propentofylline, quetiapine, rivastigmine, tacrine, tacrine hydrochloride, thalidomide, and xaliproden; active agents for treating Huntington's Disease, such as fluoxetine and carbamazepine; anti-parkinsonism drugs useful herein include amantadine, apomorphine, bromocriptine, entacapone, levodopa (particularly a levodopa/carbidopa combination), lysuride, pergolide, pramipexole, rasagiline, riluzole, ropinirole, selegiline, sumanirole, tolcapone, trihexyphenidyl, and trihexyphenidyl hydrochloride; and active agents for treating ALS such as the anti-spastic agents baclofen, diazemine, and tizanidine;

nitrates and other anti-anginal agents, such as amyl nitrate, glyceryl trinitrate, isosorbide dinitrate, isosorbide mononitrate and pentaerythritol tetranitrate;

neuroleptic drugs, including antidepressant drugs, antimanic drugs, and antipsychotic agents, wherein antidepressant drugs include (a) the tricyclic antidepressants such as amoxapine, amitriptyline, clomipramine, desipramine, doxepin, imipramine, maprotiline, nortriptyline, protriptyline, and trimipramine, (b) the serotonin reuptake inhibitors citalopram, fluoxetine, fluvoxamine, paroxetine, sertraline, and venlafaxine, (c) monoamine oxidase inhibitors such as phenelzine, tranylcypromine, and (−)-selegiline, and (d) other antidepressants such as aprepitant, bupropion, duloxetine, gepirone, igmesine, lamotrigine, maprotiline, mianserin, mirtazapine, nefazodone, rabalzotan, sunepitron, trazodone and venlafaxine, and wherein antimanic and antipsychotic agents include (a) phenothiazines such as acetophenazine, acetophenazine maleate, chlorpromazine, chlorpromazine hydrochloride, fluphenazine, fluphenazine hydrochloride, fluphenazine enanthate, fluphenazine decanoate, mesoridazine, mesoridazine besylate, perphenazine, thioridazine, thioridazine hydrochloride, trifluoperazine, and trifluoperazine hydrochloride, (b) thioxanthenes such as chlorprothixene, thiothixene, and thiothixene hydrochloride, and (c) other heterocyclic drugs such as carbamazepine, clozapine, droperidol, haloperidol, haloperidol decanoate, loxapine succinate, molindone, molindone hydrochloride, olanzapine, pimozide, quetiapine, risperidone, and sertindole.

nutritional agents, such as calcitriol, carotenes, dihydrotachysterol, essential fatty acids, non-essential fatty acids, phytonadiol, vitamin A, vitamin $B_2$, vitamin D, vitamin E and vitamin K.

opioid analgesics, such as alfentanil, apomorphine, buprenorphine, butorphanol, codeine, dextropropoxyphene, diamorphine, dihydrocodeine, fentanyl, hydrocodone, hydromorphone, levorphanol, meperidine, meptazinol, methadone, morphine, nalbuphine, oxycodone, oxymorphone, pentazocine, propoxyphene, sufentanil, and tramadol;

stimulants, including active agents for treating narcolepsy, attention deficit disorder (ADD) and attention deficit hyperactivity disorder (ADHD), such as amphetamine, dexamphetamine, dexfenfluramine, fenfluramine, mazindol, methylphenidate (including d-threo-methylphenidate, or "dexmethylphenidate," as well as racemic d,l-threo-methylphenidate), modafinil, pemoline, and sibutramine.

Preferred hydrophobic active agents include, but are not limited to, acetretin, acetyl coenzyme Q, albendazole, albuterol, aminoglutethimide, amiodarone, amlodipine, amphetamine, amphotericin B, atorvastatin, atovaquone, azithromycin, baclofen, beclomethasone, benazepril, benzonatate, betamethasone, bicalutanide, budesonide, bupropion, busulfan, butenafine, calcifediol, calcipotriene, calcitriol, camptothecin, candesartan, capsaicin, carbamezepine, carotenes, celecoxib, cerivastatin, cetirizine, chlorpheniramine, cholecalciferol, cilostazol, cimetidine, cinnarizine, ciprofloxacin, cisapride, clarithromycin, clemastine, clomiphene, clomipramine, clopidogrel, codeine, coenzyme Q10, cyclobenzaprine, cyclosporin, danazol, dantrolene, dexchlorpheniramine, diclofenac, dicumarol, digoxin, dehydroepiandrosterone, dihydroergotamine, dihydrotachysterol, dirithromycin, donezepil, efavirenz, eposartan, ergocalciferol, ergotamine, essential fatty acid sources, estradiol, etodolac, etoposide, famotidine, fenofibrate, fentanyl, fexofenadine, finasteride, fluconazole, flurbiprofen, fluvastatin, fosphenytoin, frovatriptan, furazolidone, gabapentin, gemfibrozil, glibenclamide, glipizide, glyburide, glimepiride, griseofulvin, halofantrine, ibuprofen, irbesartan, irinotecan, isosorbide dinitrate, isotretinoin, itraconazole, ivermectin, ketoconazole, ketorolac, lamotrigine, lansoprazole, leflunomide, lisinopril, loperamide, loratadine, lovastatin, L-thyroxine, lutein, lycopene, medroxyprogesterone, mifepristone, mefloquine, megestrol acetate, methadone, methoxsalen, metronidazole, miconazole, midazolam, miglitol, minoxidil, mitoxantrone, montelukast, nabumetone, nalbuphine, naratriptan, nelfinavir, nifedipine, nisoldipine, nilutanide, nitro furantoin, nizatidine, omeprazole, oprevelkin, oxaprozin, paclitaxel, paracalcitol, paroxetine, pentazocine, pioglitazone, pizofetin, pravastatin, prednisolone, probucol, progesterone, pseudoephedrine, pyridostigmine, rabeprazole, raloxifene, repaglinide, rifabutine, rifapentine, rimexolone, ritanovir, rizatriptan, rofecoxib, rosiglitazone, saquinavir, sertraline, sibutramine, sildenafil citrate, simvastatin, sirolimus, spironolactone, sumatriptan, tacrine, tacrolimus, tamoxifen, tamsulosin, targretin, tazarotene, telmisartan, teniposide, terbinafine, terazosin, tetrahydrocannabinol, tiagabine, ticlopidine, tirofiban, tizanidine, topiramate, topotecan, toremifene, tramadol, tretinoin, troglitazone, trovafloxacin, ubidecarenone, valsartan, venlafaxine, verteporfin, vigabatrin, vitamin A, vitamin D, vitamin E, vitamin K, zafirlukast, zileuton, zolmitriptan, zolpidem, zopiclone, and combinations thereof.

Preferred hydrophilic active agents that may be delivered using the method and formulations of the present invention include, without limitation, acarbose, acyclovir, acetyl cysteine, acetylcholine chloride, alatrofloxacin, alendronate, alglucerase, amantadine hydrochloride, ambenomium, amifostine, amiloride hydrochloride, aminocaproic acid, amphotericin B, antihemophilic factor (human), antihemophilic factor (porcine), antihemophilic factor (recombinant), aprotinin, asparaginase, atenolol, atracurium besylate, atropine, azithromycin, aztreonam, BCG vaccine, bacitracin, becaplermin, belladona, bepridil hydrochloride, bleomycin sulfate, calcitonin human, calcitonin salmon, carboplatin, capecitabine, capreomycin sulfate, cefamandole nafate, cefazolin sodium, cefepime hydrochloride, cefixime, cefonicid sodium, cefoperazone, cefotetan disodium, cefotaxime, cefoxitin sodium, ceftizoxime, ceftriaxone, cefuroxime axetil, cephalexin, cephapirin sodium, cholera vaccine, chorionic gonadotropin, cidofovir, cisplatin, cladribine, clidinium bromide, clindamycin and clindamycin derivatives, ciprofloxacin, clodronate, colistimethate sodium, colistin sulfate, corticotropin, cosyntropin, cromolyn sodium, cytarabine, dalteparin sodium, danaparoid, deferoxamine, denileukin diftitox, desmopressin, diatrizoate meglumine and diatrizoate sodium, dicyclomine, didanosine, dirithromycin, dopamine hydrochloride, dornase alpha, doxacurium chloride, doxorubicin, etidronate disodium, enalaprilat, enkephalin, enoxaparin, enoxaprin sodium, ephedrine, epinephrine, epoetin alpha, erythromycin, esmolol hydrochloride, factor IX, famciclovir, fludarabine, fluoxetine, foscamet sodium, ganciclovir, granulocyte colony stimulating factor, granulocyte-macrophage stimulating factor, recombinant human growth hormone, bovine growth hormine, gentamycin, glucagon, glycopyrolate, gonadotropin releasing hormone and synthetic analogs thereof, gonadorelin, grepafloxacin, haemophilus B conjugate vaccine, hepatitis A virus vaccine inactivated, hepatitis B virus vaccine inactivated, heparin sodium, indinavir sulfate, influenza virus vaccine, interleukin-2, interleukin-3, insulin-human, insulin lispro, insulin procine, insulin NPH, insulin aspart, insulin glargine, insulin detemir, interferon alpha, interferon beta, ipratropium bromide, ifosfamide, Japanese encephalitis virus vaccine, lamivudine, leucovorin calcium, leuprolide acetate, levofloxacin, lincomycin and lincomycin derivatives, lobucavir, lomefloxacin, loracarbef, mannitol, measles virus vaccine, meningococcal vaccine, menotropins, mepenzolate bromide, mesalamine, methenamine, methotrexate, methscopolamine, metformin hydrochloride, metoprolol, mezlocillin sodium, mivacurium chloride, mumps viral vaccine, nedocromil sodium, neostigmine bromide, neostigmine methyl sulfate, neurontin, norfloxacin, octreotide acetate, ofloxacin, olpadronate, oxytocin, pamidronate disodium, pancuronium bromide, paroxetine, perfloxacin, pentamidine isethionate, pentostatin, pentoxifylline, penciclovir, pentagastrin, phentolamine mesylate, phenylalanine, physostigmine salicylate, plague vaccine, piperacillin sodium, platelet derived growth factor, pneumococcal vaccine polyvalent, poliovirus vaccine (inactivated), poliovirus vaccine live (OPV), polymyxin B sulfate, pralidoxime chloride, pramlintide, pregabalin, propafenone, propenthaline bromide, pyridostigmine bromide, rabies vaccine, risedronate, ribavirin, rimantadine hydrochloride, rotavirus vaccine, salmeterol xinafoate, sincalide, small pox vaccine, solatol, somatostatin, sparfloxacin, spectinomycin, stavudine, streptokinase, streptozocin, suxamethonium chloride, tacrine hydrochloride, terbutaline sulfate, thiopeta, ticarcillin, tiludronate, timolol, tissue type plasminogen activator, TNFR:Fc, TNK-tPA, trandolapril, trimetrexate gluconate, trospectomycin, trovafloxacin, tubocurarine chloride, tumor necrosis factor, typhoid vaccine live, urea, urokinase, vancomycin, valacyclovir, valsartan, varicella virus vaccine live, vasopressin and vasopressin derivatives, vecuronium bromide, vinblastine, vincristine, vinorelbine, vitamin B12, warfarin sodium, yellow fever vaccine, zalcitabine, zanamivir, zolendronate, zidovudine, and combinations thereof.

Of course, certain active agents indicated as hydrophobic may be readily converted to and commercially available in hydrophilic form, e.g., by ionizing a non-ionized active agent so as to form a pharmaceutically acceptable, pharmacologically active salt. Conversely, certain active agents indicated as hydrophilic may be readily converted to and commercially available in hydrophobic form, e.g., by neutralization, esterification, or the like. Thus, it should be understood that the above categorization of certain active agents as hydrophilic or hydrophobic is not intended to be limiting.

Any of the aforementioned active agents may also be administered in combination using the present formulations. Active agents administered in combination may be from the same therapeutic class (e.g., lipid-regulating agents or anticoagulants) or from different therapeutic classes (e.g., a lipid-regulating agent and an anticoagulant). Examples of particularly important drug combination products include, but are not limited to:

(1) female contraceptive compositions containing both a progestogen and an estrogen;

female HRT compositions containing a progestogen, an estrogen, and an androgen;

(3) combinations of lipid-regulating agents, e.g., (a) a fibrate and a statin, such as fenofibrate and atorvastatin, fenofibrate and simvastatin, fenofibrate and lovastatin, or fenofibrate and pravastatin; (b) a fibrate and nicotinic acid, such fenofibrate and niacin; and (c) a statin and a nicotinic acid, such as lovastatin and niacin;

(4) combinations of a lipid-regulating agent and an antiviral agent, e.g., a fibrate and a protease inhibitor, such as fenofibrate and ritonavir;

(5) combinations of a lipid-regulating agent and an anticoagulant, e.g., (a) a fibrate and a salicylate, such as fenofibrate and aspirin, (b) a fibrate and another anticoagulant, such as fenofibrate and clopidogrel, (c) a statin and a salicylate, such as simvastatin and aspirin, and (d) a statin and another anticoagulant such as pravastatin and clopidogrel;

(6) combinations of a lipid-regulating agent and an antidiabetic agent, including (a) a fibrate and a insulin sensitizer such as a thiazolidinedione, e.g., fenofibrate and pioglitazone, or fenofibrate and rosiglitazone, (b) a fibrate and an insulin stimulant such as a sulfonylurea, e.g., fenofibrate and glimepiride, or fenofibrate and glipizide, a statin and and insulin sensitizer such as a thiazolidinedione, e.g., lovastatin and pioglitazone, simvastatin and rosiglitazone, pravastatin and pioglitazone, or the like;

(7) combinations of a lipid regulating agent and a cardiovascular drug, e.g., (a) a fibrate and a calcium channel blocker, such as fenofibrate and amlodipine, or fenofibrate and irbesartan, or (b) a statin and a calcium channel blocker, such as fosinopril and pravastatin;

(8) combinations of anticoagulants, e.g., (a) a salicylate and a platelet receptor binding inhibitor, such as aspirin and clopidogrel, (b) a salicylate and a low molecular weight heparin, such as aspirin and dalteparin, and (c) a platelet receptor binding inhibitor and a low molecular weight heparin, such as clopidogrel and enoxaparin;

(9) combinations of antidiabetics, e.g., (a) an insulin sensitizer and an insulin stimulant, such as (i) a thiazolidinedione such as glitazone or pioglitazone and a sulfonylurea such as glimepiride, and (ii) a biguanide such as metformin and a meglitinide such as repaglinide, (b) an insulin sensitizer and an α-glucosidase inhibitor, such as metformin and acarbose, (c) an insulin stimulant and an α-glucosidase inhibitor, such as (i) a sulfonylurea such as glyburide combined with acarbose, (ii) acarbose and a meglitinide such as repaglinide, (iii) miglitol and a sulfonylurea such as glipizide, or (iv) acarbose and a thiazolidinedione such as pioglitazone;

(10) combinations of cardiovascular drugs, such as combinations of ACE inhibitors, e.g., lisinopril and candesartan; a combination of an ACE inhibitor with a diuretic agent such as losartan and hydrochlorothiazide; a combination of a calcium channel blocker and a β-blocker such as nifedipine and atenolol; and a combination of a calcium channel blocker and an ACE inhibitor such as felodipine and ramipril;

(11) combinations of an antihypertensive agent and an antidiabetic agent, such as an ACE inhibitor and a sulfonylurea, e.g., irbesartan and glipizide;

(12) combinations of antihistamines and antiasthmatic agents, e.g., an antihistamine and a leukotriene receptor antagonist such as loratadine and zafirlukast, desloratidine and zafirlukast, and cetirazine and montelukast;

(13) combinations of antiinflammatory agents and analgesics, e.g., a COX-2 inhibitor and a nonsteroidal antiinflammatory agent (NSAID) such as rofecoxib and naproxen, or a COX-2 inhibitor and a salicylate such as celecoxib and aspirin;

(14) combinations of an anti-obesity drug and an antidiabetic agent, e.g., a lipase inhibitor such as orlistat in combination with metformin;

(15) combinations of a lipid-regulating agent and a drug for treating coronary artery disease, e.g., fenofibrate and ezetimibe, or lovastatin and ezetimibe; and other combinations, such as docetaxel and cisplatin, tirapazamine and cisplatin, metoclopramide and naproxen sodium, an opioid analgesic such as oxycodone and an anti-inflammatory agent, an agent for treating erectile dysfunction, such as alprostadil, with an antihypertensive/vasodilator such as prazosin.

The aforementioned examples are merely illustrative, and it must be emphasized that any given drug identified by structural or functional class may be replaced with another drug of the same structural or functional class.

It should also be emphasized that when the formulations and systems of the invention contain more than one active agent, the requirement of the preferred embodiment herein that at least 20% of the active agent be solubilized means, in this case, that at least 20% of only one active agent need be solubilized. Additional active agent(s) present may or may not be solubilized, i.e., they may be entirely contained in a suspended fraction of the formulation or system.

Any of the active agents may be administered in the form of a salt, ester, amide, prodrug, active metabolite, isomer, analog, fragment, or the like, provided that the salt, ester, amide, prodrug, active metabolite, isomer, analog or fragment, is pharmaceutically acceptable and pharmacologically active in the present context. Salts, esters, amides, prodrugs, metabolites, analogs, fragments, and other derivatives of the active agents may be prepared using standard procedures known to those skilled in the art of synthetic organic chemistry and described, for example, by J. March, Advanced Organic Chemistry: Reactions, Mechanisms and Structure, 4th Edition (New York: Wiley-Interscience, 1992).

For example, acid addition salts are prepared from a drug in the form of a free base using conventional methodology involving reaction of the free base with an acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt may be reconverted to the free base by treatment with a suitable base. Conversely, preparation of basic salts of acid moieties that may be present on an active agent may be carried out in a similar manner using a pharmaceutically acceptable base such as sodium hydroxide, potassium hydroxide, ammonium hydroxide, calcium hydroxide, trimethylamine, or the like. Preparation of esters involves transformation of a carboxylic acid group via a conventional esterification reaction involving nucleophilic attack of an $RO^-$ moiety at the carbonyl carbon. Esterification may also be carried out by reaction of a hydroxyl group with an esterification reagent such as an acid chloride. Esters can be reconverted to the free acids, if desired, by using conventional hydrogenolysis or hydrolysis procedures. Amides may be prepared from esters, using suitable amine reactants, or they may be prepared from an anhydride or an acid chloride by reaction with ammonia or a lower alkyl amine. Prodrugs and active metabolites may also be prepared using techniques known to those skilled in the art or described in the pertinent literature. Prodrugs are typically prepared by covalent attachment of a moiety that results in a compound that is therapeutically inactive until modified by an individual's metabolic system.

Other derivatives and analogs of the active agents may be prepared using standard techniques known to those skilled in the art of synthetic organic chemistry, or may be deduced by reference to the pertinent literature. In addition, chiral active agents may be in isomerically pure form, or they may be administered as a racemic mixture of isomers.

III. Vehicle:

The vehicle of the present formulations and systems is comprised of at least one compound selected from the group consisting of a hydrophilic surfactant, a lipophilic surfactant, a triglyceride, and a solubilizer. Such compounds provide the formulations and systems with any of several advantageous characteristics, including, but not limited to, (1) an increased amount of solubilized active agent available for immediate release, (2) improved physical and/or chemical stability of the active agent and/or formulation, (3) enhanced influx of the active agent at the site of absorption by inhibition of the efflux pump, and (4) enhanced transport of the active agent across membranes (e.g., cell membranes) or other transport barriers, i.e., an increased rate of transport, an increase in the amount of active agent transported, or both, relative to formulations in which less than 20 wt. % of an active agent to be delivered is solubilized in a vehicle. Additional advantages include improved dissolution of an active agent with respect to the extent and/or rate of dissolution under a given condition (e.g., pH, temperature, etc.), e.g., physiological conditions, and improved solubilization of the active agent released from the formulation upon dispersion in an aqueous medium, e.g., gastrointestinal fluid (with respect to the equilibrium solubility and/or the degree of supersaturation in such aqueous media).

The vehicle preferably exists as at least one liquid at a temperature of about 40° C. The liquid can be a monotropic solution or it can have a biphasic structure comprised of, for example, lamellar, cubic, hexagonal, reversed hexagonal, micellar, and/or reversed micellar phases. When the vehicle is comprised of two or more liquids, the liquids can be completely miscible, forming a single phase, or they can be partially miscible or completely immiscible, in which case the vehicle is comprised of more than two distinct phases. The liquid phase(s) in the vehicle may consist entirely of the at least one compound noted above, i.e., a hydrophilic surfactant, a lipophilic surfactant, a triglyceride, and/or a solubilizer, or a liquid carrier may be added to the aforementioned compound(s) to form the vehicle. Any pharmaceutically acceptable liquid carrier may be added, providing that in all cases, the vehicle is capable of solubilizing a significant fraction of the active agent in the formulation, i.e., at least 20 wt. % of the total active agent.

A. Surfactants:

Hydrophilic surfactants can be used to provide any of several advantageous characteristics to the compositions, including: increased solubility of the active agent in the vehicle; improved dissolution of the suspended active agent; improved solubilization of the active agent upon dissolution; enhanced absorption and/or bioavailability of the active agent; and improved stability, both physical and chemical, of the active agent. The hydrophilic surfactant can be a single hydrophilic surfactant or a mixture of hydrophilic surfactants, and can be ionic or non-ionic.

Likewise, various embodiments of the invention include a lipophilic component, which can be a lipophilic surfactant, a triglyceride, or a mixture thereof. The lipophilic surfactant and triglyceride can provide any of the advantageous characteristics listed above for hydrophilic surfactants. These various embodiments are described in more detail below. For convenience, the surfactants are described in this section, and the triglycerides in the section that follows.

As is well known in the art, the terms "hydrophilic" and "lipophilic" are relative terms. To function as a surfactant, a compound must necessarily include polar or charged hydrophilic moieties as well as non-polar hydrophobic (lipophilic) moieties; i.e., a surfactant compound must be amphiphilic. An empirical parameter commonly used to characterize the relative hydrophilicity and lipophilicity of non-ionic amphiphilic compounds is the hydrophilic-lipophilic balance (the "HLB" value). Surfactants with lower HLB values are more lipophilic, and have greater solubility in oils, whereas surfactants with higher HLB values are more hydrophilic, and have greater solubility in aqueous solutions.

Using HLB values as a rough guide, hydrophilic surfactants are generally considered to be those compounds having an HLB value greater than about 10, as well as anionic, cationic, or zwitterionic compounds for which the HLB scale is not generally applicable. Similarly, lipophilic surfactants are compounds having an HLB value less than about 10.

It should be appreciated that the HLB value of a surfactant is merely a rough guide used to enable the formulation of industrial, pharmaceutical, and cosmetic emulsions. For many important surfactants, including several polyethoxylated surfactants, it has been reported that HLB values can differ by as much as about 8 HLB units, depending upon the empirical method chosen to determine the HLB value (Schott, J. Pharm. Sciences, 79(1), 87-88 (1990)). Likewise, for certain polypropylene oxide containing block copolymers (poloxamers, available commercially as PLURONIC® surfactants, BASF Corp.), the HLB values may not accurately reflect the true physical and chemical nature of the compounds. Finally, commercial surfactant products are generally not pure compounds, but are often complex mixtures of compounds, and the HLB value reported for a particular compound may more accurately be characteristic of the commercial product of which the compound is a major component. Different commercial products having the same primary surfactant component can, and typically do, have different HLB values. In addition, a certain amount of lot-to-lot variability is expected, even for a single commercial surfactant product. Keeping these inherent difficulties in mind, and using HLB values as a guide, one skilled in the art can readily identify surfactants having suitable hydrophilicity or lipophilicity for use in the present invention, as described herein.

Surfactants can be any surfactant suitable for use in pharmaceutical compositions. Suitable surfactants can be anionic, cationic, zwitterionic, or non-ionic. Such surfactants can be grouped into the following general chemical classes detailed in the Tables herein. The HLB values given in the Tables below generally represent the HLB value as reported by the manufacturer of the corresponding commercial product. In cases where more than one commercial product is listed, the HLB value in the Tables is the value as reported for one of the commercial products, a rough average of the reported values, or a value that, in the judgment of the present inventors, is more reliable.

It should be emphasized that the invention is not limited to the surfactants in the Tables, which show representative, but not exclusive, lists of available surfactants. In addition, refined, distilled, or fractionated surfactants, purified fractions thereof, or re-esterified fractions, are also within the scope of the invention, although not specifically listed in the Tables.

Polyethoxylated Fatty Acids: Although polyethylene glycol (PEG) itself does not function as a surfactant, a variety of PEG-fatty acid esters have useful surfactant properties. Among the PEG-fatty acid monoesters, esters of lauric acid, oleic acid, and stearic acid are especially useful. Among the surfactants of Table 2, preferred hydrophilic surfactants include PEG-8 laurate, PEG-8 oleate, PEG-8 stearate, PEG-9 oleate, PEG-10 laurate, PEG-10 oleate, PEG-12 laurate, PEG-12 oleate, PEG-15 oleate, PEG-20 laurate and PEG-20 oleate. Examples of polyethoxylated fatty acid monoester surfactants commercially available are shown in Table 1.

TABLE 1

PEG-Fatty Acid Monoester Surfactants

| COMPOUND | COMMERCIAL PRODUCT (Supplier) | HLB |
|---|---|---|
| PEG 4-100 monolaurate | Crodet L series (Croda) | >9 |
| PEG 4-100 monooleate | Crodet O series (Croda) | >8 |
| PEG 4-100 monostearate | Crodet S series (Croda), Myrj Series (Atlas/ICI) | >6 |
| PEG 400 distearate | Cithrol 4DS series (Croda) | >10 |
| PEG 100, 200, 300 monolaurate | Cithrol ML series (Croda) | >10 |
| PEG 100, 200, 300 monooleate | Cithrol MO series (Croda) | >10 |
| PEG 400 dioleate | Cithrol 4DO series (Croda) | >10 |
| PEG 400-1000 monostearate | Cithrol MS series (Croda) | >10 |
| PEG-1 stearate | Nikkol MYS-1EX (Nikko), Coster K1 (Condea) | 2 |
| PEG-2 stearate | Nikkol MYS-2 (Nikko) | 4 |
| PEG-2 oleate | Nikkol MYO-2 (Nikko) | 4.5 |
| PEG-4 laurate | Mapeg ® 200 ML (PPG), Kessco ® PEG 200 ML (Stepan), LIPOPEG 2L (Lipo Chem.) | 9.3 |

TABLE 1-continued

PEG-Fatty Acid Monoester Surfactants

| COMPOUND | COMMERCIAL PRODUCT (Supplier) | HLB |
|---|---|---|
| PEG-4 oleate | Mapeg ® 200 MO (PPG), Kessco ® PEG 200 MO (Stepan), | 8.3 |
| PEG-4 stearate | Kessco ® PEG 200 MS (Stepan), Hodag 20 S (Calgene), Nikkol MYS-4 (Nikko) | 6.5 |
| PEG-5 stearate | Nikkol TMGS-5 (Nikko) | 9.5 |
| PEG-5 oleate | Nikkol TMGO-5 (Nikko) | 9.5 |
| PEG-6 oleate | Algon OL 60 (Auschem SpA), Kessco ® PEG 300 MO Stepan), Nikkol A6 (Condea) | 8.5 |
| PEG-7 oleate | Algon OL 70 (Auschem SpA) | 10.4 |
| PEG-6 laurate | Kessco ® PEG 300 ML (Stepan) | 11.4 |
| PEG-7 laurate | Lauridac 7 (Condea) | 13 |
| PEG-6 stearate | Kessco ® PEG 300 MS (Stepan) | 9.7 |
| PEG-8 laurate | Mapeg ® 400 ML (PPG), LIPOPEG 4DL (Lipo Chem.) | 13 |
| PEG-8 oleate | Mapeg ® 400 MO (PPG), Emulgante A8 (Condea) | 12 |
| PEG-8 stearate | Mapeg ® 400 MS (PPG), Myrj 45 | 12 |
| PEG-9 oleate | Emulgante A9 (Condea) | >10 |
| PEG-9 stearate | Cremophor S9 (BASF) | >10 |
| PEG-10 laurate | Nikkol MYL-10 (Nikko), Lauridac 10 (Croda) | 13 |
| PEG-10 oleate | Nikkol MYO-10 (Nikko) | 11 |
| PEG-10 stearate | Nikkol MYS-10 (Nikko), Coster K100 (Condea) | 11 |
| PEG-12 laurate | Kessco ® PEG 600 ML (Stepan) | 15 |
| PEG-12 oleate | Kessco ® PEG 600 MO (Stepan) | 14 |
| PEG-12 ricinoleate | (CAS #9004-97-1) | >10 |
| PEG-12 stearate | Mapeg ® 600 MS (PPG), Kessco ® PEG 600 MS (Stepan) | 14 |
| PEG-15 stearate | Nikkol TMGS-15 (Nikko), Koster K15 (Condea) | 14 |
| PEG-15 oleate | Nikkol TMGO-15 (Nikko) | 15 |
| PEG-20 laurate | Kessco ® PEG 1000 ML (Stepan) | 17 |
| PEG-20 oleate | Kessco ® PEG 1000 MO (Stepan) | 15 |
| PEG-20 stearate | Mapeg ® 1000 MS (PPG), Kessco ® PEG 1000 MS Stepan), Myrj 49 | 16 |
| PEG-25 stearate | Nikkol MYS-25 (Nikko) | 15 |
| PEG-32 laurate | Kessco ® PEG 1540 ML (Stepan) | 16 |
| PEG-32 oleate | Kessco ® PEG 1540 MO (Stepan) | 17 |
| PEG-32 stearate | Kessco ® PEG 1540 MS (Stepan) | 17 |
| PEG-30 stearate | Myrj 51 | >10 |
| PEG-40 laurate | Crodet L40 (Croda) | 17.9 |
| PEG-40 oleate | Crodet O40 (Croda) | 17.4 |
| PEG-40 stearate | Myrj 52, Emerest ® 2715 (Henkel), Nikkol MYS-40 (Nikko) | >10 |
| PEG-45 stearate | Nikkol MYS-45 (Nikko) | 18 |
| PEG-50 stearate | Myrj 53 | >10 |
| PEG-55 stearate | Nikkol MYS-55 (Nikko) | 18 |
| PEG-100 oleate | Crodet O-100 (Croda) | 18.8 |
| PEG-100 stearate | Myrj 59, Arlacel 165 (ICI) | 19 |
| PEG-200 oleate | Albunol 200 MO (Taiwan Surf.) | >10 |
| PEG-400 oleate | LACTOMUL (Henkel), Albunol 400 MO (Taiwan Surf.) | >10 |
| PEG-600 oleate | Albunol 600 MO (Taiwan Surf.) | >10 |

PEG-Fatty Acid Diesters: Polyethylene glycol (PEG) fatty acid diesters are also suitable for use as surfactants in the compositions of the present invention. Among the surfactants in Table 2, preferred hydrophilic surfactants include PEG-20 dilaurate, PEG-20 dioleate, PEG-20 distearate, PEG-32 dilaurate, and PEG-32 dioleate. Representative PEG-fatty acid diesters are shown in Table 2.

TABLE 2

PEG-Fatty Acid Diester Surfactants

| COMPOUND | COMMERCIAL PRODUCT (Supplier) | HLB |
|---|---|---|
| PEG-4 dilaurate | Mapeg ® 200 DL (PPG), Kessco ® PEG 200 DL (Stepan), LIPOPEG 2-DL (Lipo Chem.) | 7 |
| PEG-4 dioleate | Mapeg ® 200 DO (PPG), | 6 |
| PEG-4 distearate | Kessco ® 200 DS (Stepan) | 5 |
| PEG-6 dilaurate | Kessco ® PEG 300 DL (Stepan) | 9.8 |
| PEG-6 dioleate | Kessco ® PEG 300 DO (Stepan) | 7.2 |
| PEG-6 distearate | Kessco ® PEG 300 DS (Stepan) | 6.5 |
| PEG-8 dilaurate | Mapeg ® 400 DL (PPG), Kessco ® PEG 400 DL (Stepan), LIPOPEG 4 DL (Lipo Chem.) | 11 |
| PEG-8 dioleate | Mapeg ® 400 DO (PPG), Kessco ® PEG 400 DO (Stepan), LIPOPEG 4 O (Lipo Chem.) | 8.8 |
| PEG-8 distearate | Mapeg ® 400 DS (PPG), CDS 400 (Nikkol) | 11 |
| PEG-10 dipalmitate | Polyaldo 2PKFG | >10 |
| PEG-12 dilaurate | Kessco ® PEG 600 DL (Stepan) | 11.7 |
| PEG-12 distearate | Kessco ® PEG 600 DS (Stepan) | 10.7 |
| PEG-12 dioleate | Mapeg ® 600 DO (PPG), Kessco ® 600 DO (Stepan) | 10 |
| PEG-20 dilaurate | Kessco ® PEG 1000 DL (Stepan) | 15 |
| PEG-20 dioleate | Kessco ® PEG 1000 DO (Stepan) | 13 |
| PEG-20 distearate | Kessco ® PEG 1000 DS (Stepan) | 12 |
| PEG-32 dilaurate | Kessco ® PEG 1540 DL (Stepan) | 16 |
| PEG-32 dioleate | Kessco ® PEG 1540 DO (Stepan) | 15 |
| PEG-32 distearate | Kessco ® PEG 1540 DS (Stepan) | 15 |
| PEG-400 dioleate | Cithrol 4DO series (Croda) | >10 |
| PEG-400 distearate | Cithrol 4DS series (Croda) | >10 |

PEG-Fatty Acid Mono- and Di-Ester Mixtures: In general, mixtures of surfactants are also useful in the present invention. Several PEG-fatty acid esters are marketed commercially as mixtures of mono- and diesters. Representative surfactant mixtures are shown in Table 3.

TABLE 3

PEG-Fatty Acid Mono- and Diester Mixtures

| COMPOUND | COMMERCIAL PRODUCT (Supplier) |
|---|---|
| PEG 4-150 mono, dilaurate | Kessco ® PEG 200-6000 mono, dilaurate (Stepan) |
| PEG 4-150 mono, dioleate | Kessco ® PEG 200-6000 mono, dioleate (Stepan) |
| PEG 4-150 mono, distearate | Kessco ® 200-6000 mono, distearate (Stepan) |

Polyethylene Glycol Glycerol Fatty Acid Esters: Suitable PEG glycerol fatty acid esters are shown in Table 4. Among the surfactants in the Table, preferred hydrophilic surfactants are PEG-20 glyceryl laurate, PEG-30 glyceryl laurate, PEG-40 glyceryl laurate, PEG-20 glyceryl oleate, and PEG-30 glyceryl oleate.

TABLE 4

PEG Glycerol Fatty Acid Esters

| COMPOUND | COMMERCIAL PRODUCT (Supplier) | HLB |
|---|---|---|
| PEG-20 glyceryl laurate | Tagat ® L (Goldschmidt) | 16 |
| PEG-30 glyceryl laurate | Tagat ® L2 (Goldschmidt) | 16 |
| PEG-15 glyceryl laurate | Glycerox L series (Croda) | 15 |
| PEG-40 glyceryl laurate | Glycerox L series (Croda) | 15 |
| PEG-20 glyceryl stearate | Capmul ® EMG (ABITEC), Aldo ® MS-20 KFG (Lonza) | 13 |
| PEG-20 glyceryl oleate | Tagat ® O (Goldschmidt) | >10 |
| PEG-30 glyceryl oleate | Tagat ® O2 (Goldschmidt) | >10 |

Alcohol—Oil Transesterification Products: A large number of surfactants of different degrees of hydrophobicity or hydrophilicity can be prepared by reaction of alcohols or polyalcohols with a variety of natural and/or hydrogenated oils. Most commonly, the oils used are castor oil or hydrogenated castor oil, or an edible vegetable oil such as corn oil, olive oil, peanut oil, palm kernel oil, apricot kernel oil, or almond oil. Preferred alcohols include glycerol, propylene glycol, ethylene glycol, polyethylene glycol, sorbitol, and pentaerythritol. Among these alcohol-oil transesterified surfactants, preferred hydrophilic surfactants are PEG-35 castor oil (Incrocas®-35), PEG-40 hydrogenated castor oil (Cremophor® RH 40), PEG-25 trioleate (TAGAT® TO), PEG-60 corn glycerides (Crovol® M70), PEG-60 almond oil (Crovol® A70), PEG-40 palm kernel oil (Crovol® PK70), PEG-50 castor oil (Emalex® C-50), PEG-50 hydrogenated castor oil (Emalex® HC-50), PEG-8 caprylic/capric glycerides (Labrasol®), and PEG-6 caprylic/capric glycerides (Softigen® 767). Preferred lipophilic surfactants in this class include PEG-5 hydrogenated castor oil, PEG-7 hydrogenated castor oil, PEG-9 hydrogenated castor oil, PEG-6 corn oil (Labrafil® M 2125 CS), PEG-6 almond oil (Labrafil® M 1966 CS), PEG-6 apricot kernel oil (Labrafil® M 1944 CS), PEG-6 olive oil (Labrafil® M 1980 CS), PEG-6 peanut oil (Labrafil® M 1969 CS), PEG-6 hydrogenated palm kernel oil (Labrafil® M 2130 BS), PEG-6 palm kernel oil (Labrafil® M 2130 CS), PEG-6 triolein (Labrafil® M 2735 CS), PEG-8 corn oil (Labrafil® WL 2609 BS), PEG-20 corn glycerides (Crovol® M40), and PEG-20 almond glycerides (Crovol® A40). The latter two surfactants are reported to have HLB values of 10, which is generally considered to be the approximate border line between hydrophilic and lipophilic surfactants. For purposes of the present invention, these two surfactants are considered to be lipophilic. Representative surfactants of this class suitable for use in the present invention are shown in Table 5.

TABLE 5

Transesterification Products of Oils and Alcohols

| COMPOUND | COMMERCIAL PRODUCT (Supplier) | HLB |
|---|---|---|
| PEG-3 castor oil | Nikkol CO-3 (Nikko) | 3 |
| PEG-5, 9, and 16 castor oil | ACCONON CA series (ABITEC) | 6-7 |
| PEG-20 castor oil | Emalex C-20 (Nihon Emulsion), Nikkol CO-20 TX (Nikko) | 11 |
| PEG-23 castor oil | Emulgante EL23 | >10 |
| PEG-30 castor oil | Emalex C-30 (Nihon Emulsion), Alkamuls ® EL 620 (Rhone-Poulenc), Incrocas 30 (Croda) | 11 |
| PEG-35 castor oil | Cremophor EL and EL-P (BASF), Emulphor EL, Incrocas-35 (Croda), Emulgin RO 35 (Henkel) | |
| PEG-38 castor oil | Emulgante EL 65 (Condea) | |
| PEG-40 castor oil | Emalex C-40 (Nihon Emulsion), Alkamuls ® EL 719 (Rhone-Poulenc) | 13 |
| PEG-50 castor oil | Emalex C-50 (Nihon Emulsion) | 14 |
| PEG-56 castor oil | Eumulgin ® PRT 56 (Pulcra SA) | >10 |
| PEG-60 castor oil | Nikkol CO-60TX (Nikko) | 14 |
| PEG-100 castor oil | Thornley | >10 |
| PEG-200 castor oil | Eumulgin ® PRT 200 (Pulcra SA) | >10 |
| PEG-5 hydrogenated castor oil | Nikkol HCO-5 (Nikko) | 6 |
| PEG-7 hydrogenated castor oil | Simusol ® 989 (Seppic), Cremophor WO7 (BASF) | 6 |
| PEG-10 hydrogenated castor oil | Nikkol HCO-10 (Nikko) | 6.5 |
| PEG-20 hydrogenated castor oil | Nikkol HCO-20 (Nikko) | 11 |
| PEG-25 hydrogenated castor oil | Simulsol ® 1292 (Seppic), Cerex ELS 250 (Auschem SpA) | 11 |
| PEG-30 hydrogenated castor oil | Nikkol HCO-30 (Nikko) | 11 |
| PEG-40 hydrogenated castor oil | Cremophor RH 40 (BASF), Croduret (Croda), Emulgin HRE 40 (Henkel) | 13 |
| PEG-45 hydrogenated castor oil | Cerex ELS 450 (Auschem Spa) | 14 |
| PEG-50 hydrogenated castor oil | Emalex HC-50 (Nihon Emulsion) | 14 |
| PEG-60 hydrogenated castor oil | Nikkol HCO-60 (Nikko); Cremophor RH 60 (BASF) | 15 |

TABLE 5-continued

Transesterification Products of Oils and Alcohols

| COMPOUND | COMMERCIAL PRODUCT (Supplier) | HLB |
|---|---|---|
| PEG-80 hydrogenated castor oil | Nikkol HCO-80 (Nikko) | 15 |
| PEG-100 hydrogenated castor oil | Nikkol HCO-100 (Nikko) | 17 |
| PEG-6 corn oil | Labrafil ® M 2125 CS (Gattefosse) | 4 |
| PEG-6 almond oil | Labrafil ® M 1966 CS (Gattefosse) | 4 |
| PEG-6 apricot kernel oil | Labrafil ® M 1944 CS (Gattefosse) | 4 |
| PEG-6 olive oil | Labrafil ® M 1980 CS (Gattefosse) | 4 |
| PEG-6 peanut oil | Labrafil ® M 1969 CS (Gattefosse) | 4 |
| PEG-6 hydrogenated palm kernel oil | Labrafil ® M 2130 BS (Gattefosse) | 4 |
| PEG-6 palm kernel oil | Labrafil ® M 2130 CS (Gattefosse) | 4 |
| PEG-6 triolein | Labrafil ® M 2735 CS (Gattefosse) | 4 |
| PEG-8 corn oil | Labrafil ® WL 2609 BS (Gattefosse) | 6-7 |
| PEG-20 corn glycerides | Crovol M40 (Croda) | 10 |
| PEG-20 almond glycerides | Crovol A40 (Croda) | 10 |
| PEG-25 trioleate | TAGAT ® TO (Goldschmidt) | 11 |
| PEG-40 palm kernel oil | Crovol PK-70 | >10 |
| PEG-60 corn glycerides | Crovol M70 (Croda) | 15 |
| PEG-60 almond glycerides | Crovol A70 (Croda) | 15 |
| PEG-4 caprylic/capric triglyceride | Labrafac ® Hydro (Gattefosse), | 4-5 |
| PEG-8 caprylic/capric glycerides | Labrasol (Gattefosse), Labrafac CM 10 (Gattefosse) | >10 |
| PEG-6 caprylic/capric glycerides | SOFTIGEN ® 767 (Hüls), Glycerox 767 (Croda) | 19 |
| Lauroyl macrogol-32 glyceride | GELUCIRE 44/14 (Gattefosse) | 14 |
| Stearoyl macrogol glyceride | GELUCIRE 50/13 (Gattefosse) | 13 |
| Mono, di, tri, tetra esters of vegetable oils and sorbitol | SorbitoGlyceride (Gattefosse) | <10 |
| Pentaerythrityl tetraisostearate | Crodamol PTIS (Croda) | <10 |
| Pentaerythrityl distearate | Albunol DS (Taiwan Surf.) | <10 |
| Pentaerythrityl tetraoleate | Liponate PO-4 (Lipo Chem.) | <10 |
| Pentaerythrityl tetrastearate | Liponate PS-4 (Lipo Chem.) | <10 |
| Pentaerythrityl tetracaprylate/tetracaprate | Liponate PE-810 (Lipo Chem.), Crodamol PTC (Croda) | <10 |
| Pentaerythrityl tetraoctanoate | Nikkol Pentarate 408 (Nikko) | |

Also included as oils in this category of surfactants are oil-soluble vitamin substances. The oil-soluble vitamin substances include vitamins A, D, E, K, and isomers, analogues, and derivatives thereof. The derivatives include organic acid esters of these oil-soluble vitamin substances, such as the esters of vitamin E or vitamin A with succinic acid. Thus, derivatives of these vitamins, such as tocopheryl PEG-1000 succinate (Vitamin E TPGS, available from Eastman) and other tocopheryl PEG succinate derivatives with various molecular weights of the PEG moiety, such as PEG 100-8000, are also suitable surfactants.

Polyglycerized Fatty Acids: Polyglycerol esters of fatty acids are also suitable surfactants for the present invention.

Among the polyglyceryl fatty acid esters, preferred lipophilic surfactants include polyglyceryl oleate (Plurol Oleique®), polyglyceryl-2 dioleate (Nikkol DGDO), and polyglyceryl-10 trioleate. Preferred hydrophilic surfactants include polyglyceryl-10 laurate (Nikkol Decaglyn 1-L), polyglyceryl-10 oleate (Nikkol Decaglyn 1-O), and polyglyceryl-10 mono dioleate (Caprol® PEG 860). Polyglyceryl polyricinoleates (Polymuls) are also preferred hydrophilic and hydrophobic surfactants. Examples of suitable polyglyceryl esters are shown in Table 6.

TABLE 6

Polyglycerized Fatty Acids

| COMPOUND | COMMERCIAL PRODUCT (Supplier) | HLB |
|---|---|---|
| Polyglyceryl-2 stearate | Nikkol DGMS (Nikko) | 5-7 |
| Polyglyceryl-2 oleate | Nikkol DGMO (Nikko) | 5-7 |
| Polyglyceryl-2 isostearate | Nikkol DGMIS (Nikko) | 5-7 |
| Polyglyceryl-3 oleate | Caprol ® 3GO (ABITEC), Drewpol 3-1-O (Stepan) | 6.5 |
| Polyglyceryl-4 oleate | Nikkol Tetraglyn 1-O (Nikko) | 5-7 |
| Polyglyceryl-4 stearate | Nikkol Tetraglyn 1-S (Nikko) | 5-6 |
| Polyglyceryl-6 oleate | Drewpol 6-1-O (Stepan), Nikkol Hexaglyn 1-O (Nikko) | 9 |
| Polyglyceryl-10 laurate | Nikkol Decaglyn 1-L (Nikko) | 15 |
| Polyglyceryl-10 oleate | Nikkol Decaglyn 1-O (Nikko) | 14 |
| Polyglyceryl-10 stearate | Nikkol Decaglyn 1-S (Nikko) | 12 |
| Polyglyceryl-6 ricinoleate | Nikkol Hexaglyn PR-15 (Nikko) | >8 |
| Polyglyceryl-10 linoleate | Nikkol Decaglyn 1-LN (Nikko) | 12 |
| Polyglyceryl-6 pentaoleate | Nikkol Hexaglyn 5-O (Nikko) | <10 |
| Polyglyceryl-3 dioleate | Cremophor GO32 (BASF) | <10 |
| Polyglyceryl-3 distearate | Cremophor GS32 (BASF) | <10 |
| Polyglyceryl-4 pentaoleate | Nikkol Tetraglyn 5-O (Nikko) | <10 |

TABLE 6-continued

Polyglycerized Fatty Acids

| COMPOUND | COMMERCIAL PRODUCT (Supplier) | HLB |
| --- | --- | --- |
| Polyglyceryl-6 dioleate | Caprol ® 6G20 (ABITEC); Hodag PGO-62 (Calgene), PLUROL OLEIQUE CC 497 (Gattefosse) | 8.5 |
| Polyglyceryl-2 dioleate | Nikkol DGDO (Nikko) | 7 |
| Polyglyceryl-10 trioleate | Nikkol Decaglyn 3-O (Nikko) | 7 |
| Polyglyceryl-10 pentaoleate | Nikkol Decaglyn 5-O (Nikko) | 3.5 |
| Polyglyceryl-10 septaoleate | Nikkol Decaglyn 7-O (Nikko) | 3 |
| Polyglyceryl-10 tetraoleate | Caprol ® 10G4O (ABITEC); Hodag PGO-62 (CALGENE), Drewpol 10-4-O (Stepan) | 6.2 |
| Polyglyceryl-10 decaisostearate | Nikkol Decaglyn 10-IS (Nikko) | <10 |
| Polyglyceryl-101 decaoleate | Drewpol 10-10-O (Stepan), Caprol 10G10O (ABITEC), Nikkol Decaglyn 10-O | 3.5 |
| Polyglyceryl-10 mono, dioleate | Caprol ® PGE 860 (ABITEC) | 11 |
| Polyglyceryl polyricinoleate | Polymuls (Henkel) | 3-20 |

Propylene Glycol Fatty Acid Esters: Esters of propylene glycol and fatty acids are suitable surfactants for use in the present invention. In this surfactant class, preferred lipophilic surfactants include propylene glycol monocaprylate (Capryol® 90), propylene glycol monolaurate (Lauroglycol FCC), propylene glycol ricinoleate (Propymuls®), propylene glycol monooleate (Myverol® PO-6), propylene glycol dicaprylate/dicaprate (Captex® 200; Miglylol® 840), and propylene glycol dioctanoate (Captex® 800). Examples of surfactants of this class are given in Table 7.

TABLE 7

Propylene Glycol Fatty Acid Esters

| COMPOUND | COMMERCIAL PRODUCT (Supplier) | HLB |
| --- | --- | --- |
| Propylene glycol monocaprylate | Capryol 90 (Gattefosse), Nikkol Sefsol 218 (Nikko) | <10 |
| Propylene glycol monolaurate | Lauroglycol 90 (Gattefosse), Lauroglycol FCC (Gattefosse) | <10 |
| Propylene glycol oleate | Lutrol OP2000 (BASF) | <10 |
| Propylene glycol myristate | Mirpyl | <10 |
| Propylene glycol monostearate | ADM PGME-03 (ADM), LIPO PGMS (Lipo Chem.), Aldo ® PGHMS (Lonza) | 3-4 |
| Propylene glycol hydroxy stearate |  | <10 |
| Propylene glycol ricinoleate | PROPYMULS (Henkel) | <10 |
| Propylene glycol isostearate |  | <10 |
| Propylene glycol monooleate | Myverol P-O6 (Eastman) | <10 |
| Propylene glycol dicaprylate/dicaprate | Captex ® 200 (ABITEC), Miglyol ® 840 (Hüls), Neobee ® M-20 | >6 |
| Propylene glycol dioctanoate | Captex ® 800 (ABITEC) | >6 |
| Propylene glycol caprylate/caprate | LABRAFAC PG (Gattefosse) | >6 |
| Propylene glycol dilaurate |  | >6 |
| Propylene glycol distearate | Kessco ® PGDS (Stepan) | >6 |
| Propylene glycol dicaprylate | Nikkol Sefsol 228 (Nikko) | >6 |
| Propylene glycol dicaprate | Nikkol PDD (Nikko) | >6 |

TABLE 8

Glycerol/Propylene Glycol Fatty Acid Esters

| COMPOUND | COMMERCIAL PRODUCT (Supplier) | HLB |
| --- | --- | --- |
| Oleic | ATMOS 300, ARLACEL 186 (ICI) | 3-4 |
| Stearic | ATMOS 150 | 3-4 |

Mixtures of Propylene Glycol Esters—Glycerol Esters: In general, mixtures of surfactants are also suitable for use in the present invention. In particular, mixtures of propylene glycol fatty acid esters and glycerol fatty acid esters are suitable and are commercially available. One preferred mixture is composed of the oleic acid esters of propylene glycol and glycerol (Arlacel® 186). Examples of these surfactants are shown in Table 8.

Mono- and Diglycerides: A particularly important class of surfactants is the class of mono- and diglycerides. These surfactants are generally hydrophobic. Preferred lipophilic surfactants in this class of compounds include glyceryl monooleate (Peceol), glyceryl ricinoleate, glyceryl laurate, glyceryl dilaurate (Capmul® GDL), glyceryl dioleate (Capmul® GDO), glyceryl mono- and di-oleate (Capmul® GMO-K), glyceryl caprylate/caprate (Capmul® MCM), caprylic acid mono- and di-glycerides (Imwitor® 988), and mono- and diacetylated monoglycerides (Myvacet® 9-45). Examples of these surfactants are given in Table 9.

ylene glycol moeity. Examples of surfactants in this class are shown in Table 10.

TABLE 9

Mono- and Diglyceride Surfactants

| COMPOUND | COMMERCIAL PRODUCT (Supplier) | HLB |
| --- | --- | --- |
| Monopalmitolein (C16:1) | (Larodan) | <10 |
| Monoelaidin (C18:1) | (Larodan) | <10 |
| Monocaproin (C6) | (Larodan) | <10 |
| Monocaprylin | (Larodan) | <10 |
| Monocaprin | (Larodan) | <10 |
| Monolaurin | (Larodan) | <10 |
| Glyceryl monomyristate (C14) | Nikkol MGM (Nikko) | 3-4 |
| Glyceryl monooleate (C18:1) | PECEOL (Gattefosse), Hodag GMO-D, Nikkol MGO (Nikko) | 3-4 |
| Glyceryl monooleate | RYLO series (Danisco), DIMODAN series (Danisco), EMULDAN (Danisco), ALDO ® MO FG (Lonza), Kessco GMO (Stepan), MONOMULS ® series (Henkel), TEGIN O, DREWMULSE GMO (Stepan), Atlas G-695 (ICI), GMOrphic 80 (Eastman), ADM DMG-40, 70, and 100 (ADM), Myverol (Eastman) | 3-4 |
| Glycerol monooleate/linoleate | OLICINE (Gattefosse) | 3-4 |
| Glycerol monolinoleate | Maisine (Gattefosse), Myverol 18-92, Myverol 18-06 (Eastman) | 3-4 |
| Glyceryl ricinoleate | Softigen ® 701 (Hüls), HODAG GMR-D (Calgene), ALDO ® MR | 6 |
| Glyceryl monolaurate | ALDO ® MLD (Lonza), Hodag GML (Calgene) | 6.8 |
| Glycerol monopalmitate | Emalex GMS-P (Nihon) | 4 |
| Glycerol monostearate | Capmul ® GMS (ABITEC), Myvaplex (Eastman), Imwitor ® 191 (Hüls), CUTINA ® GMS, Aldo ® MS (Lonza), Nikkol MGS series (Nikko) | 5-9 |
| Glyceryl mono-, dioleate | Capmul ® GMO-K (ABITEC) | <10 |
| Glyceryl palmitic/stearic | CUTINA MD-A, ESTAGEL-G18 | <10 |
| Glyceryl acetate | Lamegin ® EE (Grünau GmbH) | <10 |
| Glyceryl laurate | Imwitor ® 312 (Hüls), Monomuls ® 90-45 (Grünau GmbH), Aldo ® (Lonza) | 4 |
| Glyceryl citrate/lactate/oleate/linoleate | Imwitor ® 375 (Hüls) | <10 |
| Glyceryl caprylate | Imwitor ® 308 (Hüls), Capmul ® MCMC8 (ABITEC) | 5-6 |
| Glyceryl caprylate/caprate | Capmul ® MCM (ABITEC) | 5-6 |
| Caprylic acid mono/diglycerides | Imwitor ® 988 (Hüls) | 5-6 |
| Caprylic/capric glycerides | Imwitor ® 742 (Hüls) | <10 |
| Mono- and diacetylated monoglycerides | Myvacet ® 9-45, Myvacet ® 9-40, Myvacet ® 9-08 (Eastman), Lamegin ® (Grünau) | 3.8-4 |
| Glyceryl monostearate | Aldo ® MS, Arlacel 129 (ICI), LIPO GMS (Lipo Chem.), Imwitor ® 191 (Hüls), Myvaplex (Eastman) | 4.4 |
| Lactic acid esters of mono, diglycerides | LAMEGIN GLP (Henkel) | <10 |
| Dicaproin (C6) | (Larodan) | <10 |
| Dicaprin (C10) | (Larodan) | <10 |
| Dioctanoin (C8) | (Larodan) | <10 |
| Dimyristin (C14) | (Larodan) | <10 |
| Dipalmitin (C16) | (Larodan) | <10 |
| Distearin | (Larodan) | <10 |
| Glyceryl dilaurate (C12) | Capmul ® GDL (ABITEC) | 3-4 |
| Glyceryl dioleate | Capmul ® GDO (ABITEC) | 3-4 |
| Glycerol esters of fatty acids | GELUCIRE 39/01 (Gattefosse), GELUCIRE 43/01 (Gattefosse) | 1 |
|  | GELUCIRE 37/06 (Gattefosse) | 6 |
| Dipalmitolein (C16:1) | (Larodan) | <10 |
| 1,2 and 1,3-diolein (C18:1) | (Larodan) | <10 |
| Dielaidin (C18:1) | (Larodan) | <10 |
| Dilinolein (C18:2) | (Larodan) | <10 |

Sterol and Sterol Derivatives: Sterols and derivatives of sterols are suitable surfactants for use in the present invention. These surfactants can be hydrophilic or lipophilic. A preferred sterol in this class is cholesterol or the esters of cholesterol with an organic acid, such cholesteryl succinate. Preferred derivatives include the polyethylene glycol derivatives. These derivatives could be esters and ethers depending upon the chemical bonds formed between the polyethylene glycol moiety and the sterol moiety. Preferred hydrophilic surfactants in this class include PEG-24 cholesterol ether (Solulan C-24) and cholesteryl polyethylene glycol succinate, containing various molecular weights of the polyeth-

TABLE 10

Sterol and Sterol Derivative Surfactants

| COMPOUND | COMMERCIAL PRODUCT (Supplier) | HLB |
| --- | --- | --- |
| Cholesterol, sitosterol, lanosterol |  | <10 |
| PEG-24 cholesterol ether | Solulan C-24 (Amerchol) | >10 |
| PEG-30 cholestanol | Nikkol DHC (Nikko) | >10 |
| Phytosterol | GENEROL series (Henkel) | <10 |
| PEG-25 phyto sterol | Nikkol BPSH-25 (Nikko) | >10 |
| PEG-5 soya sterol | Nikkol BPS-5 (Nikko) | <10 |
| PEG-10 soya sterol | Nikkol BPS-10 (Nikko) | <10 |

TABLE 10-continued

Sterol and Sterol Derivative Surfactants

| COMPOUND | COMMERCIAL PRODUCT (Supplier) | HLB |
|---|---|---|
| PEG-20 soya sterol | Nikkol BPS-20 (Nikko) | <10 |
| PEG-30 soya sterol | Nikkol BPS-30 (Nikko) | >10 |

Polyethylene Glycol Sorbitan Fatty Acid Esters: A variety of PEG-sorbitan fatty acid esters are commercially available and are suitable for use as surfactants in the present invention. In general, these surfactants are hydrophilic, although several lipophilic surfactants of this class can be used. Among the PEG-sorbitan fatty acid esters, preferred hydrophilic surfactants include PEG-20 sorbitan monolaurate (Tween-20), PEG-sorbitan monopalmitate (Tween-40), PEG-20 sorbitan monostearate (Tween-60), and PEG-20 sorbitan monooleate (Tween-80). Examples of these surfactants are shown in Table 11.

TABLE 11

PEG-Sorbitan Fatty Acid Esters

| COMPOUND | COMMERCIAL PRODUCT (Supplier) | HLB |
|---|---|---|
| PEG-10 sorbitan laurate | Liposorb L-10 (Lipo Chem.) | >10 |
| PEG-20 sorbitan monolaurate | Tween-20 (Atlas/ICI), Crillet 1 (Croda), DACOL MLS 20 (Condea) | 17 |
| PEG-4 sorbitan monolaurate | Tween-21 (Atlas/ICI), Crillet 11 (Croda) | 13 |
| PEG-80 sorbitan monolaurate | Hodag PSML-80 (Calgene); T-Maz 28 | >10 |
| PEG-6 sorbitan monolaurate | Nikkol GL-1 (Nikko) | 16 |
| PEG-20 sorbitan monopalmitate | Tween-40 (Atlas/ICI), Crillet 2 (Croda) | 16 |
| PEG-20 sorbitan monostearate | Tween-60 (Atlas/ICI), Crillet 3 (Croda) | 15 |
| PEG-4 sorbitan monostearate | Tween-61 (Atlas/ICI), Crillet 31 (Croda) | 9.6 |
| PEG-8 sorbitan monostearate | DACOL MSS (Condea) | >10 |
| PEG-6 sorbitan monostearate | Nikkol TS106 (Nikko) | 11 |
| PEG-20 sorbitan tristearate | Tween-65 (Atlas/ICI), Crillet 35 (Croda) | 11 |
| PEG-6 sorbitan tetrastearate | Nikkol GS-6 (Nikko) | 3 |
| PEG-60 sorbitan tetrastearate | Nikkol GS-460 (Nikko) | 13 |
| PEG-5 sorbitan monooleate | Tween-81 (Atlas/ICI), Crillet 41 (Croda) | 10 |
| PEG-6 sorbitan monooleate | Nikkol TO-106 (Nikko) | 10 |
| PEG-20 sorbitan monooleate | Tween-80 (Atlas/ICI), Crillet 4 (Croda) | 15 |
| PEG-40 sorbitan oleate | Emalex ET 8040 (Nihon Emulsion) | 18 |
| PEG-20 sorbitan trioleate | Tween-85 (Atlas/ICI), Crillet 45 (Croda) | 11 |
| PEG-6 sorbitan tetraoleate | Nikkol GO-4 (Nikko) | 8.5 |
| PEG-30 sorbitan tetraoleate | Nikkol GO-430 (Nikko) | 12 |
| PEG-40 sorbitan tetraoleate | Nikkol GO-440 (Nikko) | 13 |
| PEG-20 sorbitan monoisostearate | Tween-120 (Atlas/ICI), Crillet 6 (Croda) | >10 |
| PEG sorbitol hexaoleate | Atlas G-1086 (ICI) | 10 |
| PEG-6 sorbitol hexastearate | Nikkol GS-6 (Nikko) | 3 |

Polyethylene Glycol Alkyl Ethers: Ethers of polyethylene glycol and alkyl alcohols are suitable surfactants for use in the present invention. Preferred lipophilic ethers include PEG-3 oleyl ether (Volpo® 3) and PEG-4 lauryl ether (Brij® 30). Examples of these surfactants are shown in Table 12.

TABLE 12

Polyethylene Glycol Alkyl Ethers

| COMPOUND | COMMERCIAL PRODUCT (Supplier) | HLB |
|---|---|---|
| PEG-2 oleyl ether, oleth-2 | Brij 92/93 (Atlas/ICI) | 4.9 |
| PEG-3 oleyl ether, oleth-3 | Volpo 3 (Croda) | <10 |
| PEG-5 oleyl ether, oleth-5 | Volpo 5 (Croda) | <10 |
| PEG-10 oleyl ether, oleth-10 | Volpo 10 (Croda), Brij 96/97 (Atlas/ICI) | 12 |

TABLE 12-continued

Polyethylene Glycol Alkyl Ethers

| COMPOUND | COMMERCIAL PRODUCT (Supplier) | HLB |
|---|---|---|
| PEG-20 oleyl ether, oleth-20 | Volpo 20 (Croda), Brij 98/99 (Atlas/ICI) | 15 |
| PEG-4 lauryl ether, laureth-4 | Brij 30 (Atlas/ICI) | 9.7 |
| PEG-9 lauryl ether | | >10 |
| PEG-23 lauryl ether, laureth-23 | Brij 35 (Atlas/ICI) | 17 |
| PEG-2 cetyl ether | Brij 52 (ICI) | 5.3 |
| PEG-10 cetyl ether | Brij 56 (ICI) | 13 |
| PEG-20 cetyl ether | Brij 58 (ICI) | 16 |
| PEG-2 stearyl ether | Brij 72 (ICI) | 4.9 |
| PEG-10 stearyl ether | Brij 76 (ICI) | 12 |
| PEG-20 stearyl ether | Brij 78 (ICI) | 15 |
| PEG-100 stearyl ether | Brij 700 (ICI) | >10 |

Sugar Esters: Esters of sugars are suitable surfactants for use in the present invention. Preferred hydrophilic surfactants in this class include sucrose monopalmitate and sucrose monolaurate. Examples of such surfactants are shown in Table 13.

TABLE 13

Sugar Ester Surfactants

| COMPOUND | COMMERCIAL PRODUCT (Supplier) | HLB |
|---|---|---|
| Sucrose distearate | SUCRO ESTER 7 (Gattefosse), Crodesta F-10 (Croda) | 3 |
| Sucrose distearate/monostearate | SUCRO ESTER 11 (Gattefosse), Crodesta F-110 (Croda) | 12 |
| Sucrose dipalmitate | | 7.4 |
| Sucrose monostearate | Crodesta F-160 (Croda) | 15 |
| Sucrose monopalmitate | SUCRO ESTER 15 (Gattefosse) | >10 |
| Sucrose monolaurate | Saccharose monolaurate 1695 (Mitsubishi-Kasei) | 15 |

Polyethylene Glycol Alkyl Phenols: Several hydrophilic PEG-alkyl phenol surfactants are commercially available, and are suitable for use in the present invention. Examples of these surfactants are shown in Table 14.

TABLE 14

Polyethylene Glycol Alkyl Phenol Surfactants

| COMPOUND | COMMERCIAL PRODUCT (Supplier) | HLB |
|---|---|---|
| PEG-10-100 nonyl phenol | Triton X series (Rohm & Haas), Igepal CA series (GAF, USA), Antarox CA series (GAF, UK) | >10 |
| PEG-15-100 octyl phenol ether | Triton N-series (Rohm & Haas), Igepal CO series (GAF, USA), Antarox CO series (GAF, UK) | >10 |

Polyoxyethylene-Polyoxypropylene Block Copolymers: The POE-POP block copolymers are a unique class of polymeric surfactants. The unique structure of the surfactants, with hydrophilic POE and hydrophobic POP moieties in well-defined ratios and positions, allows for a wide variety of surfactants suitable for use in the present invention. These surfactants are available under various trade names, including Synperoni®c PE series (ICI); Pluronic® series (BASF), Emkalyx®, Lutrol® (BASF), Supronic®, Monolan®, Pluracare®, and Plurodac®. The generic term for these polymers is "poloxamer" (CAS 9003-11-6). These polymers have the formula $$HO(C_2H_4O)_a(C_3H_6O)_b(C_2H_4O)_aH$$

wherein "a" and "b" denote the number of polyoxyethylene and polyoxypropylene units, respectively.

Preferred hydrophilic surfactants of this class include Poloxamers 108, 188, 217, 238, 288, 338, and 407. Preferred lipophilic surfactants in this class include Poloxamers 124, 182, 183, 212, 331, and 335.

Examples of suitable surfactants of this class are shown in Table 15. Since the compounds are widely available, commercial sources are not listed in the Table. The compounds are listed by generic name, with the corresponding "a" and "b" values.

TABLE 15

POE-POP Block Copolymers

| COMPOUND | a, b values in $HO(C_2H_4O)_a(C_3H_6O)_b(C_2H_4O)_aH$ | | HLB |
|---|---|---|---|
| Poloxamer 105 | a = 11 | b = 16 | 8 |
| Poloxamer 108 | a = 46 | b = 16 | >10 |
| Poloxamer 122 | a = 5 | b = 21 | 3 |
| Poloxamer 123 | a = 7 | b = 21 | 7 |
| Poloxamer 124 | a = 11 | b = 21 | >7 |
| Poloxamer 181 | a = 3 | b = 30 | |

TABLE 15-continued

POE-POP Block Copolymers

| COMPOUND | a, b values in $HO(C_2H_4O)_a(C_3H_6O)_b(C_2H_4O)_aH$ | | HLB |
|---|---|---|---|
| Poloxamer 182 | a = 8 | b = 30 | 2 |
| Poloxamer 183 | a = 10 | b = 30 | |
| Poloxamer 184 | a = 13 | b = 30 | |
| Poloxamer 185 | a = 19 | b = 30 | |
| Poloxamer 188 | a = 75 | b = 30 | 29 |
| Poloxamer 212 | a = 8 | b = 35 | |
| Poloxamer 215 | a = 24 | b = 35 | |
| Poloxamer 217 | a = 52 | b = 35 | |
| Poloxamer 231 | a = 16 | b = 39 | |
| Poloxamer 234 | a = 22 | b = 39 | |
| Poloxamer 235 | a = 27 | b = 39 | |
| Poloxamer 237 | a = 62 | b = 39 | 24 |
| Poloxamer 238 | a = 97 | b = 39 | |
| Poloxamer 282 | a = 10 | b = 47 | |
| Poloxamer 284 | a = 21 | b = 47 | |
| Poloxamer 288 | a = 122 | b = 47 | >10 |
| Poloxamer 331 | a = 7 | b = 54 | 0.5 |
| Poloxamer 333 | a = 20 | b = 54 | |
| Poloxamer 334 | a = 31 | b = 54 | |
| Poloxamer 335 | a = 38 | b = 54 | |
| Poloxamer 338 | a = 128 | b = 54 | |
| Poloxamer 401 | a = 6 | b = 67 | |
| Poloxamer 402 | a = 13 | b = 67 | |
| Poloxamer 403 | a = 21 | b = 67 | |
| Poloxamer 407 | a = 98 | b = 67 | |

Other block co-polymers are also suitable for the present invention. The block co-polymers can be made of various block components in different combination and sequences, such as BA diblock, ABA triblock, BAB triblock, and other more complex combinations and sequences involving three or more block components. The block components can be any poly(alkylene oxide), poly(lactic acid), poly(glycolic acid), poly(lactic-co-glycolic acid), poly(vinylpyrrolidone) and poly(ε-caprolactone). The molecular weights of suitable block co-polymers can range from a few thouthand to a few million Daltons. These block co-polymers can be either hydrophilic or lipophilic depending on the distribution and ratios of different block components. Other co-polymers, not necessarily block co-polymers, are also suitable for the present invention. The co-polymers can be made of monomers of any combinations. The monomer component can be any alkylene oxide, lactic acid, glycolic acid, vinylpyrrolidone, or ε-caprolactone.

Sorbitan Fatty Acid Esters: Sorbitan esters of fatty acids are suitable surfactants for use in the present invention. Among these esters, preferred hydrophobic surfactants include sorbitan monolaurate (Arlacel® 20), sorbitan monopalmitate (Span-40®), sorbitan monooleate (Span-80®), sorbitan monostearate, and sorbitan tristearate. Examples of these surfactants are shown in Table 16.

TABLE 16

Sorbitan Fatty Acid Ester Surfactants

| COMPOUND | COMMERCIAL PRODUCT (Supplier) | HLB |
|---|---|---|
| Sorbitan monolaurate | Span-20 (Atlas/ICI), Crill 1 (Croda), Arlacel 20 (ICI) | 8.6 |
| Sorbitan monopalmitate | Span-40 (Atlas/ICI), Crill 2 (Croda), Nikkol SP-10 (Nikko) | 6.7 |
| Sorbitan monooleate | Span-80 (Atlas/ICI), Crill 4 (Croda), Crill 50 (Croda) | 4.3 |
| Sorbitan monostearate | Span-60 (Atlas/ICI), Crill 3 (Croda), Nikkol SS-10 (Nikko) | 4.7 |
| Sorbitan trioleate | Span-85 (Atlas/ICI), Crill 45 (Croda), Nikkol SO-30 (Nikko) | 4.3 |

TABLE 16-continued

Sorbitan Fatty Acid Ester Surfactants

| COMPOUND | COMMERCIAL PRODUCT (Supplier) | HLB |
| --- | --- | --- |
| Sorbitan sesquioleate | Arlacel-C (ICI), Crill 43 (Croda), Nikkol SO-15 (Nikko) | 3.7 |
| Sorbitan tristearate | Span-65 (Atlas/ICI) Crill 35 (Croda), Nikkol SS-30 (Nikko) | 2.1 |
| Sorbitan monoisostearate | Crill 6 (Croda), Nikkol SI-10 (Nikko) | 4.7 |
| Sorbitan sesquistearate | Nikkol SS-15 (Nikko) | 4.2 |

Lower Alcohol Fatty Acid Esters: Esters of lower alcohols ($C_2$ to $C_4$) and fatty acids ($C_8$ to $C_{18}$) are suitable for use in the present invention. Among these esters, preferred lipophilic surfactants include ethyl oleate (Crodamol® EO), isopropyl myristate (Crodamol® IPM), and isopropy palmitate (Crodamol® IPP). Examples of these surfactants are shown in Table 17.

TABLE 17

Lower Alcohol Fatty Acid Ester Surfactants

| COMPOUND | COMMERCIAL PRODUCT (Supplier) | HLB |
| --- | --- | --- |
| Ethyl oleate | Crodamol EO (Croda), Nikkol EOO (Nikko) | <10 |
| Isopropyl myristate | Crodamol IPM (Croda) | <10 |
| Isopropyl palmitate | Crodamol IPP (Croda) | <10 |
| Ethyl linoleate | Nikkol VF-E (Nikko) | <10 |
| Isopropyl linoleate | Nikkol VF-IP (Nikko) | <10 |

Ionic Surfactants: Ionic surfactants, including cationic, anionic, and zwitterionic surfactants, are suitable hydrophilic surfactants for use in the present invention. Preferred anionic surfactants include fatty acid salts and bile salts. Preferred cationic surfactants include carnitines. Specifically, preferred ionic surfactants include sodium oleate, sodium lauryl sulfate, sodium lauryl sarcosinate, sodium dioctyl sulfosuccinate, sodium cholate, sodium taurocholate, lauroyl camitine, palmitoyl carnitine, and myristoyl carnitine. Examples of such surfactants are shown in Table 18. For simplicity, typical counterions are shown in the entries in the Table. It will be appreciated by one skilled in the art, however, that any bioacceptable counterion may be used. For example, although the fatty acids are shown as sodium salts, other cation counterions can also be used, such as alkali metal cations or ammonium. Unlike typical non-ionic surfactants, these ionic surfactants are generally available as pure compounds, rather than as commercial (proprietary) mixtures. Because these compounds are readily available from a variety of commercial suppliers, such as Aldrich, Sigma, and the like, commercial sources are not generally listed in the Table.

TABLE 18

Ionic Surfactants

| COMPOUND | HLB |
| --- | --- |
| FATTY ACID SALTS | >10 |
| Sodium caproate | |
| Sodium caprylate | |
| Sodium caprate | |
| Sodium laurate | |
| Sodium myristate | |
| Sodium myristolate | |
| Sodium palmitate | |
| Sodium palmitoleate | |

TABLE 18-continued

Ionic Surfactants

| COMPOUND | HLB |
| --- | --- |
| Sodium oleate | 18 |
| Sodium ricinoleate | |
| Sodium linoleate | |
| Sodium linolenate | |
| Sodium stearate | |
| Sodium lauryl sulfate (dodecyl) | 40 |
| Sodium tetradecyl sulfate | |
| Sodium lauryl sarcosinate | |
| Sodium dioctyl sulfosuccinate [sodium docusate (Cytec)] | |
| BILE SALTS | >10 |
| Sodium cholate | |
| Sodium taurocholate | |
| Sodium glycocholate | |
| Sodium deoxycholate | |
| Sodium taurodeoxycholate | |
| Sodium glycodeoxycholate | |
| Sodium ursodeoxycholate | |
| Sodium chenodeoxycholate | |
| Sodium taurochenodeoxycholate | |
| Sodium glyco chenodeoxycholate | |
| Sodium cholylsarcosinate | |
| Sodium N-methyl taurocholate | |
| PHOSPHOLIPIDS | |
| Egg/Soy lecithin [Epikuron ® (Lucas Meyer), Ovothin ® (Lucas Meyer)] | |
| Cardiolipin | |
| Sphingomyelin | |
| Phosphatidylcholine | |
| Phosphatidyl ethanolamine | |
| Phosphatidic acid | |
| Phosphatidyl glycerol | |
| Phosphatidyl serine | |
| PHOSPHORIC ACID ESTERS | |
| Diethanolammonium polyoxyethylene-10 oleyl ether phosphate | |
| Esterification products of fatty alcohols or fatty alcohol ethoxylates with phosphoric acid or anhydride | |
| CARBOXYLATES | |
| Ether carboxylates (by oxidation of terminal OH group of fatty alcohol ethoxylates) | |
| Succinylated monoglycerides [LAMEGIN ZE (Henkel)] | |
| Sodium stearyl fumarate | |
| Stearoyl propylene glycol hydrogen succinate | |
| Mono/diacetylated tartaric acid esters of mono- and diglycerides | |
| Citric acid esters of mono-, diglycerides | |
| Glyceryl-lacto esters of fatty acids (CFR ref. 172.852) | |
| Acyl lactylates: | |
| lactylic esters of fatty acids | |
| calcium/sodium stearoyl-2-lactylate | |
| calcium/sodium stearoyl lactylate | |
| Alginate salts | |
| Propylene glycol alginate | |
| SULFATES AND SULFONATES | |
| Ethoxylated alkyl sulfates | |
| Alkyl benzene sulfones | |

TABLE 18-continued

Ionic Surfactants

| COMPOUND | HLB |
|---|---|
| α-olefin sulfonates | |
| Acyl isethionates | |
| Acyl taurates | |
| Alkyl glyceryl ether sulfonates | |
| Octyl sulfosuccinate disodium | |
| Disodium undecylenamideo-MEA-sulfosuccinate | |
| CATIONIC Surfactants | >10 |
| Hexadecyl triammonium bromide | |
| Dodecyl ammonium chloride | |
| Alkyl benzyldimethylammonium salts | |
| Diisobutyl phenoxyethoxydimethyl benzylammonium salts | |
| Alkylpyridinium salts | |
| Betaines (trialkylglycine): | |
| Lauryl betaine (N-lauryl,N,N-dimethylglycine) | |
| Ethoxylated amines: | |
| Polyoxyethylene-15 coconut amine | |

Non-Ionized Ionizable Surfactants: Ionizable surfactants, when present in their non-ionized (neutral, non-salt) form, are lipophilic surfactants suitable for use in the compositions and methods of the present invention. Particular examples of such surfactants include free fatty acids, particularly $C_6$-$C_{22}$ fatty acids, and bile acids. More specifically, suitable non-ionized ionizable surfactants include the free fatty acid and bile acid forms of any of the fatty acid salts and bile salts shown in Table 18.

Among the above-listed surfactants, several combinations are preferred. In some of the preferred combinations, the vehicle includes at least one hydrophilic surfactant. Preferred non-ionic hydrophilic surfactants include alkylglucosides; alkylmaltosides; alkylthioglucosides; lauryl macrogolglycerides; polyoxyethylene alkyl ethers; polyoxyethylene alkylphenols; polyethylene glycol fatty acids esters; polyethylene glycol glycerol fatty acid esters; polyoxyethylene sorbitan fatty acid esters; polyoxyethylene-polyoxypropylene block copolymers; polyglycerol fatty acid esters; polyoxyethylene glycerides; polyoxyethylene sterols, derivatives, and analogues thereof; polyoxyethylene vegetable oils; polyoxyethylene hydrogenated vegetable oils; reaction mixtures of polyols with fatty acids, glycerides, vegetable oils, hydrogenated vegetable oils, and sterols; sugar esters; sugar ethers; sucroglycerides; and mixtures thereof.

More preferably, the non-ionic hydrophilic surfactant is selected from the group consisting of polvoxyethylene alkylethers; polyethylene glycol fatty acid esters; polyethylene glycol glycerol fatty acid esters; polyoxyethylene sorbitan fatty acid esters; polyoxyethylene-polyoxypropylene block copolymers; polyglyceryl fatty acid esters; polyoxyethylene glycerides; polyoxyethylene vegetable oils; and polyoxyethylene hydrogenated vegetable oils. The glyceride can be a monoglyceride, diglyceride, triglyceride, or a mixture.

Also preferred are non-ionic hydrophilic surfactants that are reaction mixtures of polyols and fatty acids, glycerides, vegetable oils, hydrogenated vegetable oils, or sterols. These reaction mixtures are largely composed of the transesterification products of the reaction, along with commonly complex mixtures of other reaction products. The polyol is preferably glycerol, ethylene glycol, polyethylene glycol, sorbitol, propylene glycol, pentaerythritol, or a saccharide.

Several particularly preferred compositions are those that include as a non-ionic hydrophilic surfactant such as PEG-10 laurate, PEG-12 laurate, IIEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-1000 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, or a poloxamer.

Among these preferred surfactants, more preferred are PEG-20 laurate, PEG-20 oleate, PEG-35 castor oil, PEG-40 palm kernel oil, PEG-40 hydrogenated castor oil, PEG-60 corn oil, PEG-25 glyceryl trioleate, polyglyceryl-10 laurate, PEG-6 caprate/caprylate glycerides, PEG-8 caprate/caprylate glycerides, PEG-30 cholesterol, polysorbate 20 polysorbate 80, POE-9 lauryl ether, POE-23 lauryl ether, POE-10 oleyl ether, PEG-24 cholesterol, sucrose monostearate, sucrose monolaurate, and poloxamers. Most preferred are PEG-35 castor oil, PEG-40 hydrogenated castor oil, PEG-60 corn oil, PEG-25 glyceryl trioleate, PEG-6 caprate/caprylate glycerides, PEG-8 caprate/caprylate glycerides, polysorbate 20, polysorbate 80, tocopheryl PEG-1000 succinate, PEG-24 cholesterol, and hydrophilic poloxamers.

The hydrophilic surfactant can also be, or can include as a component, an ionic surfactant. Preferred ionic surfactants include alkyl ammonium salts; bile acids and salts, analogues, and derivatives thereof; fusidic acid and derivatives thereof; fatty acid derivatives of amino acids, oligopeptides, and polypeptides; glyceride derivatives of amino acids oligopeptides, and polypeptides; acyl lactylates; mono-and di-acetylated tartaric acid esters of mono- and di-glycerides; succinylated monoglycerides; citric acid esters of mono- and di-glycerides; alginate salts; propylene glycol alginate; lecithins and hydrogenated lecithins; lysolecithin and hydrogenated lysolecithins; lysophospholipids and derivatives thereof; phospholipids and derivatives thereof; salts of alkylsulfates; salts of fatty acids; sodium docusate; carnitines; and mixtures thereof.

More preferable ionic surfactants include bile acids and salts, analogues, and derivatives thereof; lecithins, lysolecithin, phospholipids, lysophospholipids and derivatives thereof; salts of alkylsulfates; salts of fatty acids; sodium docusate; acyl lactylates; mono- and di-acetylated tartaril acid esters of mono- and di-glycerides; succinylated monoglycerides; citric acid esters of mono- and di-glycerides; carnitines; and mixtures thereof.

More specifically, preferred ionic surfactants are lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono- and di-acetylated tartaric acid esters of mono- and di-glycerides, citric acid esters of mono- and di-glycerides, cholate, taurocholate, glycocholate, deoxycholate, taurodeoxycholate, chenodeoxycholate, glycodeoxycholate, glycochenodeoxycholate, taurochenodeoxycholate, ursodeoxycholate, tauroursodeoxycholate, glycoursodeoxycholate, cholylsarcosine, N-methyl taurocholate, caproate, caprylate, caprate, laurate, myristate, palmitate, oleate, ricinoleate, linoleate, linolenate, stearate, lauryl sulfate, teracecyl sulfate, docusate, lauroyl camitines, palmitoyl carnitines, myristoyl camitines, and salts and mixtures thereof.

Particularly preferred ionic surfactants are lecithin, lysolecithin, phosphatidylcholine, phosphatidylethanolamine, phosphatidylglycerol, lysophosphatidylcholine, PEG-phosphatidylethanolamine, lactylic esters of fatty acids, stearoyl-2-lactylate, stearoyl lactylate, succinylated monoglycerides, mono- and di-acetylated tartaric acid esters of mono- and di-glycerides, citric acid esters of mono- and di-glycerides cholate, taurocholate glycocholate, deoxycholate, taurodeoxycholate, glycodeoxycholate, cholylsarcosine, caproate, caprylate, caprate, laurate, oleate, lauryl sulfate, docusate, and salts and mixtures thereof, with the most preferred ionic surfactants being lecithin, lactylic esters of fatty acids, stearoyl-2-lactylate, stearoyl lactylate, succinylated monoglycerides, mono- and di-acetylated tartaric acid esters of mono- and di-glycerides, citric acid esters of mono- and di-glycerides, taurocholate, caprylate, caprate, oleate, lauryl sulfate, docusate, and salts and mixtures thereof.

Preferred lipophilic surfactants are alcohols; polyoxyethylene alkylethers; fatty acids; glycerol fatty acid esters; acetylated glycerol fatty acid esters; lower alcohol fatty acid esters; polyethylene glycol fatty acid esters; polyethylene glycol glycerol fatty acid esters; polypropylene glycol fatty acid esters; polyoxyethylene glycerides; lactic acid derivatives of mono- and di-glycerides; propylene glycol diglycerides; sorbitan fatty acid esters; polyoxyethylene sorbitan fatty acid esters; polyoxyethylene-polyoxypropylene block copolymers; transesterified vegetable oils; sterols; sterol derivatives; sugar esters; sugar ethers; sucroglycerides; polyoxyethylene vegetable oils; and polyoxyethylene hydrogenated vegetable oils.

As with the hydrophilic surfactants, lipophilic surfactants can be reaction mixtures of polyols and fatty acids, glycerides, vegetable oils, hydrogenated vegetable oils, and sterols.

Preferably, the lipophilic surfactant is selected from the group consisting of fatty acids; lower alcohol fatty acid esters; polyethylene glycol glycerol fatty acid esters; polypropylene glycol fatty acid esters; polyoxyethylene glycerides; glycerol fatty acid esters; acetylated glycerol fatty acid esters; lactic acid derivatives of mono- and di-glycerides; sorbitan fatty acid esters; polyoxyethylene sorbitan fatty acid esters; polyoxyethylene-polyoxypropylene block copolymers; polyoxyethylene vegetable oils; polyoxyethylene hydrogenated vegetable oils; and reaction mixtures of polyols and fatty acids, glycerides, vegetable oils, hydrogenated vegetable oils, and sterols.

More preferred are lower alcohol fatty acids esters; polypropylene glycol fatty acid esters; propylene glycol fatty acid esters; glycerol fatty acid esters; acetylated glycerol fatty acid esters; lactic acid derivatives of mono- and di-glycerides; sorbitan fatty acid esters; polyoxyethylene vegetable oils; and mixtures thereof, with glycerol fatty acid esters and acetylated glycerol fatty acid esters being most preferred. Among the glycerol fatty acid esters, the esters are preferably mono- or diglycerides, or mixtures of mono- and diglycerides, where the fatty acid moiety is a $C_6$ to $C_{22}$ fatty acid.

Also preferred are lipophilic surfactants that are the reaction mixture of polyols and fatty acids, glycerides, vegetable oils, hydrogenated vegetable oils, and sterols. Preferred polyols are polyethylene glycol, sorbitol, propylene glycol, and pentaerythritol.

Specifically preferred lipophilic surfactants include myristic acid; oleic acid; lauric acid; stearic acid; palmitic acid; PEG 1-4 stearate; PEG 2-4 oleate; PEG-4 dilaurate; PEG-4 dioleate; PEG-4 distearate; PEG-6 dioleate; PEG-6 distearate; PEG-8 dioleate; PEG 3-16 castor oil; PEG 5-10 hydrogenated castor oil; PEG 6-20 corn oil; PEG 6-20 almond oil; PEG-6 olive oil; PEG-6 peanut oil; PEG-6 palm kernel oil; PEG-6 hydrogenated palm kernel oil; PEG-4 capric/caprylic triglyceride, mono, di, tri, tetra esters of vegetable oil and sorbitol; pentaerythrityl di or tetra stearate, isostearate, oleate, caprylate, or caprate; polyglyceryl 2-4 oleate, stearate, or isostearate; polyglyceryl 4-10 pentaoleate; polyglyceryl-3 dioleate; polyglyceryl-6 dioleate; polyglyceryl-10 trioleate; polyglyceryl-3 distearate; propylene glycol mono- or diesters of a $C_6$ to $C_{20}$ fatty acid; monoglycerides of $C_6$ to $C_{20}$ fatty acids; acetylated monoglycerides of $C_6$ to $C_{20}$ fatty acids; diglycerides of $C_6$ to $C_{20}$ fatty acids; tocopheryl PEG-800 succinate; lactic acid derivatives of monoglycerides; lactic acid derivatives of diglycerides; cholesterol; phytosterol; PEG 5-20 soya sterol; PEG-6 sorbitan tetra, hexastearate; PEG-6 sorbitan tetraoleate; sorbitan monolaurate; sorbitan monopalmitate; sorbitan mono, trioleate; sorbitan mono, tristearate; sorbitan monoisostearate; sorbitan sesquioleate; sorbitan sesquistearate; PEG 2-5 oleyl ether; POE 2-4 lauryl ether; PEG-2 cetyl ether; PEG-2 stearyl ether; sucrose distearate; sucrose dipalmitate; ethyl oleate; isopropyl myristate; isopropyl palmitate; ethyl linoleate; isopropyl linoleate; and poloxamers.

Among the specifically preferred lipophilic surfactants, most preferred are oleic acid; lauric acid; glyceryl monocaprate; glyceryl monocaprylate; glyceryl monolaurate; glyceryl monooleate; glyceryl dicaprate; glyceryl dicaprylate; glyceryl dilaurate; glyceryl dioleate; acetylated monoglycerides; propylene glycol oleate; propylene glycol laurate; polyglyceryl-3 oleate; polyglyceryl-6 dioleate; PEG-6 corn oil; PEG-20 corn oil; PEG-20 almond oil; sorbitan monooleate; sorbitan monolaurate; POE-4 lauryl ether; POE-3 oleyl ether; ethyl oleate; tocopheryl PEG-800 succinate; and poloxamers.

B. Triglycerides:

Examples of triglycerides suitable for use in the present invention are shown in the following table. In general, these triglycerides are readily available from commercial sources. For several triglycerides, representative commercial products and/or commercial suppliers are listed.

TABLE 19

Representative Triglycerides

| TRIGLYCERIDE | COMMERCIAL SOURCE |
|---|---|
| Aceituno oil | |
| Almond oil | Super Refined Almond Oil (Croda) |
| Arachis oil | |
| Babassu oil | |
| Blackcurrant seed oil | |
| Borage oil | |
| Buffalo ground oil | |
| Candlenut oil | |
| Canola oil | Lipex 108 (Abitec) |
| Caster oil | |
| Chinese vegetable tallow oil | |
| Cocoa butter | |
| Coconut oil | |
| Coffee seed oil | Pureco 76 (Abitec) |

TABLE 19-continued

Representative Triglycerides

| TRIGLYCERIDE | COMMERCIAL SOURCE |
|---|---|
| Corn oil | Super Refined Corn Oil (Croda) |
| Cottonseed oil | Super Refined Cottonseed Oil (Croda) |
| Crambe oil | |
| Cuphea species oil | |
| Evening primrose oil | |
| Grapeseed oil | |
| Groundnut oil | |
| Hemp seed oil | |
| Illipe butter | |
| Kapok seed oil | |
| Linseed oil | |
| Menhaden oil | Super Refined Menhaden Oil (Croda) |
| Mowrah butter | |
| Mustard seed oil | |
| Oiticica oil | |
| Olive oil | Super Refined Olive Oil (Croda) |
| Palm oil | |
| Palm kernel oil | |
| Peanut oil | Super Refined Peanut Oil (Croda) |
| Poppy seed oil | |
| Rapeseed oil | |
| Rice bran oil | |
| Safflower oil | Super Refined Safflower Oil (Croda) |
| Sal fat | |
| Sesame oil | Super Refined Sesame Oil (Croda) |
| Shark liver oil | Super Refined Shark Liver Oil (Croda) |
| Shea nut oil | |
| Soybean oil | Super Refined Soybean Oil (Croda) |
| Stillingia oil | |
| Sunflower oil | |
| Tall oil | |
| Tea sead oil | |
| Tobacco seed oil | |
| Tung oil (China wood oil) | |
| Ucuhuba | |
| Vernonia oil | |
| Wheat germ oil | Super Refined Wheat Germ Oil (Croda) |
| Hydrogenated caster oil | Castorwax |
| Hydrogenated coconut oil | Pureco 100 (Abitec) |
| Hydrogenated cottonseed oil | Dritex C (Abitec) |
| Hydrogenated palm oil | Dritex PST (Abitec); Softisan 154 (Hüls) |
| Hydrogenated soybean oil | Sterotex HM NF (Abitec); Dritex S (Abitec) |
| Hydrogenated vegetable oil | Sterotex NF (Abitec): Hydrokote M (Abitec) |
| Hydrogenated cottonseed/castor oil | Sterotex K (Abitec) |
| Partially hydrogenated soybean oil | Hydrokote AP5 (Abitec) |
| Partially soy and cottonseed oil | Apex B (Abitec) |
| Glyceryl tributyrate | (Sigma) |
| Glyceryl tricaproate | (Sigma) |
| Glyceryl tricaprylate | (Sigma) |
| Glyceryl tricaprate | Captex 1000 (Abitec) |
| Glyceryl trundecanoate | Captex 8227 (Abitec) |
| Glyceryl trilaurate | (Sigma) |
| Glyceryl trimyristate | Dynasan 114 (Hüls) |
| Glyceryl tripalmitate | Dynasan 116 (Hüls) |
| Glyceryl tristearate | Dynasan 118 (Hüls) |
| Glyceryl triarcidate | (Sigma) |
| Glyceryl trimyristoleate (Sigma) | (Sigma) |
| Glyceryl tripalmitoleate | (Sigma) |
| Glyceryl trioleate | (Sigma) |
| Glyceryl trilinoleate | (Sigma) |
| Glyceryl trilinolenate | (Sigma) |
| Glyceryl tricaprylate/caprate | Captex 300 (Abitec); Captex 355 (Abitec); Miglyol 810 (Hüls); Miglyol 812 (Hüls) |
| Glyceryl tricaprylate/caprate/laurate | Captex 350 (Abitec) |
| Glyceryl tricaprylate/caprate/linoleate | Captex 810 (Abitec); Miglyol 818 (Hüls) |
| Glyceryl tricaprylate/caprate/stearate | Softisan 378 (Hüls); (Larodan) |
| Glyceryl tricaprylate/laurate/stearate | (Larodan) |
| Glyceryl 1,2-caprylate-3-linoleate | (Larodan) |
| Glyceryl 1,2-caprate-3-stearate | (Larodan) |
| Glyceryl 1,2-laurate-3-myristate | (Larodan) |
| Glyceryl 1,2-myristate-3-laurate | (Larodan) |
| Glyceryl 1,3-palmitate-2-butyrate | (Larodan) |
| Glyceryl 1,3-stearate-2-caprate | (Larodan) |
| Glyceryl 1,2-linoleate-3-caprylate | (Larodan) |

Fractionated triglycerides, modified triglycerides, synthetic triglycerides, and mixtures of triglycerides are also within the scope of the invention.

Preferred triglycerides include vegetable oils, fish oils, animal fats, hydrogenated vegetable oils, partially hydrogenated vegetable oils, medium and long-chain triglycerides, and structured triglycerides. It should be appreciated that several commercial surfactant compositions contain small to moderate amounts of triglycerides, typically as a result of incomplete reaction of a triglyceride starting material in, for example, a transesterification reaction. Such commercial surfactant compositions, while nominally referred to as "surfactants", may be suitable to provide all or part of the triglyceride component for the compositions of the present invention. Examples of commercial surfactant compositions containing triglycerides include some members of the surfactant families Gelucire (Gattefosse), Maisine (Gattefosse), and Imwitor® (Hüls), such as: Gelucire 44/14 (saturated polyglycolized glycerides); Gelucire 50/13 (saturated polyglycolized glycerides); Gelucire 53/10 (saturated polyglycolized glycerides);

Gelucire 33/01 (semi-synthetic triglycerides of $C_8$ to $C_{18}$ saturated fatty acids); Gelucire 39/01 (semi-synthetic glycerides); other Gelucires, such as 37/06, 43/01, 35/10, 37/02, 46/07, 48/09, 50/02, 62/05, etc.; Maisine 35-1 (linoleic glycerides); and Imwitor 742 (caprylic/capric glycerides).

Still other commercial surfactant compositions having significant triglyceride content are known to those skilled in the art. It should be appreciated that such compositions, which contain triglycerides as well as surfactants, may be suitable to provide all or part of the triglyceride component of the compositions of the present invention, as well as all or part of the surfactant component, as described below. Of course, none of the commonly known triglyceride-containing commercial surfactants alone provides the unique pharmaceutical compositions and characteristics as recited in the appended claims.

Among the above-listed triglycerides, preferred triglycerides include: almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; partially soy and cottonseed oil; glyceryl tricaproate; glyceryl tricaprylate; glyceryl tricaprate; glyceryl triundecanoate; glyceryl trilaurate; glyceryl trioleate;

glyceryl trilinoleate; glyceryl trilinolenate; glyceryl tricaprylate/caprate; glyceryl tricaprylate/caprate/laurate; glyceryl tricaprylate/caprate/linoleate; and glyceryl tricaprylate/caprate/stearate. Other preferred triglycerides are saturated polyglycolized glycerides (Gelucire 44/14, Gelucire 50/13 and Gelucire 53/10), linoleic glycerides (Maisine® 35-I), and caprylic/capric glycerides (Imwitor® 742).

Among the preferred triglycerides, more preferred triglycerides include: coconut oil; corn oil; olive oil; palm oil; peanut oil; safflower oil; sesame oil; soybean oil; hydrogenated castor oil; hydrogenated coconut oil; partially hydrogenated soybean oil; glyceryl tricaprate; glyceryl trilaurate; glyceryl trioleate; glyceryl trilinoleate; glyceryl tricaprylate/caprate; glyceryl tricaprylate/caprate/laurate; glyceryl tricaprylate/caprate/linoleate; glyceryl tricaprylate/caprate/stearate; saturated polyglycolized glycerides (Gelucire 44/14, Gelucire 14 50/13 and Gelucire 53/10); linoleic glycerides (Maisine® 35-1); and caprylic/capric glycerides (Imwitor® 742).

C. Solubilizers:

In one preferred embodiment, the vehicle comprises at least one solubilizer to increase the solubility of the active agent therein. Examples of such compounds, referred to as "solubilizers", include:

Alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins, and cyclodextrin derivatives;

Ethers of polyethylene glycols having an average molecular weight of about 200 to about 6000, such as tetrahydrofurfuryl alcohol PEG ether (glycofurol, available commercially from BASF under the trade name Tetraglycol) or methoxy PEG (Union Carbide);

Amides, such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide, and polyvinylpyrrolidone;

Esters, such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof;

Oil-soluble vitamin substances, such as tocopherol, tocopheryl acetate, tocopheryl succinate, tocotrienols, isomers thereof and mixtures thereof; and other solubilizers known in the art, such as dimethyl acetamide, dimethyl isosorbide (Arlasolve DMI (ICI)), N-methyl pyrrolidones (Pharmasolve (ISP)), monooctanoin, diethylene glycol monoethyl ether (available from Gattefosse under the trade name Transcutol), and water.

Mixtures of solubilizers are also within the scope of the invention.

Preferred solubilizers include triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol, and propylene glycol.

In preferred embodiments, the vehicle of the present compositions comprises at least two compounds selected from the group consisting of hydrophilic surfactants, lipophilic surfactants, triglycerides, and solubilizers. Among the more preferred embodiments, the vehicle includes at least two hydrophilic surfactants and at least one lipophilic surfactant; or at least one hydrophilic surfactant, at least one lipophilic surfactant, and at least one triglyceride.

The amount of hydrophilic surfactant, lipophilic surfactant, triglyceride, and solubilizer that can be included in compositions of the present invention is not particularly limited. Of course, when such compositions are ultimately administered to a patient, the amount of a given excipient is limited to a bioacceptable amount, which is readily determined by one of skill in the art. In some circumstances, it may be advantageous to include amounts of the excipient far in excess of bioacceptable amounts, for example, to maximize the concentration of a therapeutic agent, with excess solubilizer removed prior to providing the composition to a patient using conventional techniques, such as distillation or evaporation. Thus, if present, each can be present in an amount of about 0.5% to about 100% by weight, based on the weight of the vehicle. Typically, each is present at about 5% to about 70% by weight and more typically, about 10% to about 50% by weight.

In particularly preferred embodiments, the amount of hydrophilic surfactant, lipophilic surfactant, triglyceride, and solubilizer are such that upon mixing with an aqueous medium, the vehicle forms a clear aqueous dispersion. Any dilution ratio can be selected, but convenient dilutions are those within the range expected in vivo, about a 10 to 250-fold dilution in purified water, gastric fluid/simulated gastric fluid, or intestinal fluid/simulated intestinal fluid. The aqueous dispersion is then assessed qualitatively for optical clarity. The procedure can be repeated with incremental variations in the relative amount of lipophilic surfactant, triglyceride, and/or solubilizer added, to determine the maximum relative amount of that lipophilic surfactant, triglyceride, and/or solubilizer can be present for a given combination.

Alternatively, the optical clarity of the aqueous dispersion can be measured using standard quantitative techniques for turbidity assessment. One convenient procedure to measure turbidity is to measure the amount of light of a given wavelength transmitted by the solution, using, for example, a UV-visible spectrophotometer. Using this measure, optical clarity corresponds to high transmittance, since cloudier solutions will scatter more of the incident radiation, resulting in lower transmittance measurements. If this procedure is used, care should be taken to insure that any stabilizing agent or other additives that may contribute turbidity or absorbance to the aqueous dispersion is excluded from the suspending vehicle when the aqueous dispersion is prepared. It also should be noted whether the surfactant, triglyceride and/or solubilizer mixture does not itself absorb light of the chosen wavelength, as any true absorbance necessarily reduces the amount of transmitted light and falsely increases the quantitative turbidity value. In the absence of chromophores at the chosen wavelength, suitable dispersions, at an aqueous medium to vehicle ratio of 100:1 by weight, should have an apparent absorbance of less than about 0.5, preferably less than about 0.3, and more preferably less than about 0.1. At an aqueous medium to vehicle ratio of 10:1 by weight, suitable dispersions should have an apparent absorbance of less than about 0.7, preferably less than about 0.3, and more preferably less than about 0.1.

Optimally, the amounts of hydrophilic surfactant, lipophilic surfactant, triglyceride, and solubilizer are such that upon mixing with an aqueous medium, the vehicle forms an aqueous dispersion with a narrow particle size distribution. Any dilution amount can be chosen, but convenient dilutions are those within the range expected in vivo, about a 10 to 250-fold dilution in purified water, gastric fluid/simulated gastric fluid, or intestinal fluid/simulated intestinal fluid. Measurements of the particle size distribution of the aqueous dispersion can be performed on commercially available particle size analyzers, such as, for example, a Nicomp particle size analyzer available from Particle Size Systems, Inc., of Santa Barbara, Calif. It is desirable that the average particle size be less than about 1000 nm, preferably less than about 200 nm, more preferably less than about 50 nm, and still more preferably less than about 20 nm. It is also preferred that the particle size distribution be unimodal.

Other methods of determining optical clarity or particle size can be used as desired. Such methods are well known to those skilled in the art.

Although it should be understood that any aqueous dispersion having the properties described above is within the scope of the present invention, regardless of the specific relative amounts of lipophilic and hydrophilic surfactants and triglyceride, it is expected that the amount of lipophilic surfactant and/or triglyceride will generally be less than about 200% by weight of any hydrophilic surfactant present, and more specifically, in the range of about 1% to 200%. Further, it is expected that the amount of lipophilic surfactant and/or triglyceride will generally be less than about 100%, and more specifically in the range of about 5% to about 100% by weight, or about 10% to about 100% by weight, of any hydrophilic surfactant.

Other considerations well known to those skilled in the art will further facilitate the choice of specific proportions of each compound. These considerations include, for example, the degree of bioacceptability of the surfactants, and the desired dosage of active agent to be provided. In some cases, the amount of lipophilic surfactant and/or triglyceride actually used in a formulation of the present invention will be less than the maximum that could be used, and it should be apparent that such compositions are also within the scope of the present invention.

In a preferred embodiment, the pharmaceutical composition and the dosage form of the invention are substantially free of added water and are therefore substantially nonaqueous. By "substantially aqueous" is meant that a composition or dosage form, as prepared, contains less than about 20% (v/v) free water, wherein "free" water refers to any water present that is capable of forming a continuous aqueous phase or otherwise has the ability to migrate freely (e.g., into the interior wall of a gelatin capsule). More preferably, a composition or dosage form of the invention contains less than about 10% free water, and, most preferably, the composition or dosage form contains less than about 5% free water. In turn, as alluded to above, this means that any water present will not form a continuous aqueous phase and/or does not have the mobility to migrate freely within or out of the composition or dosage form.

The lack of water provides pharmaceutical compositions and dosage forms with improved stability and compatibility, if the presence of a significant amount of water would present such problems. For example, numerous active agents and excipients are prone to hydrolysis. Excluding significant amounts of water from the composition would help slow down or stop the chemical degradation caused by water. Water-free compositions would allow such excipients to maintain the desired physical form and preserve their intended functions. Significant amounts of water may not be compatible with certain dosage forms such as gelatin capsules. Large amounts of water present in the fill may change the water content in the shells and eventually cause softening, dissolving, leaking, or breaking of the capsules during storage.

In a preferred embodiment of the present invention, however, a small percentage of water is present in the composition, so that an appropriate equilibrium can be established between the filled material and the hard or soft gelatin capsule shells, to prevent cracking or brittleness of the capsules. Compositions containing an appropriate amount of water would help to maintain the integrity of the dosage form, making such encapsulations practical. It also appreciated that in a preferred embodiment, certain excipients may undergo phase changes, such as precipitation, swelling, and gelation, in the presence of significant amounts of water. In some such cases, water would thus provide useful stabilizing or suspending effects on the suspension. Appropriate amounts of water would be thus desirable in these cases. For similar reasons, it is also preferred that the compositions of the present invention comprise appropriate amount of other hydrophilic components, such as propylene glycol, glycerol, sorbitol, polyethylene oxides, or mixtures thereof.

IV. The Suspension:

The pharmaceutical suspension is minimally comprised of an active agent and a vehicle, sometimes referred to herein as a "suspending" vehicle. In some cases, a significant fraction of the active agent may be solubilized in the vehicle for immediate release and/or absorption, while the rest of the active agent may be suspended in the vehicle for delayed, sustained, and/or rapid release. By varying the fractions of solubilized and suspended active agent, the release and/or absorption profile of the active agent can be modulated and controlled. It is surprisingly found that when the fraction of active agent that is solubilized varies from about 20 to 95 wt %, and the fraction that is suspended correspondingly varies from about 5 to 80 wt %, desirable release and/or absorption profile characteristics of the active agent are obtained that can increase the therapeutic efficacy of the active agent. More preferably, about 30 to 80 wt % of the active agent present in the suspension is solubilized and about 20 to 70 wt % of the active agent is suspended in the vehicle. Most preferably, about 50 to 70 wt % of the active agent present in the suspension is solubilized and about 30 to 50 wt % of the active agent is suspended in the vehicle.

The invention enables facile modulation of the pharmacokinetic/pharmacodynamic profile of an active agent because of the high degree of control provided over the timing and rate of drug release. If a rapid onset or a large initial loading dose of the active agent is desired, immediate release of active agent can be accomplished by solubilizing the majority of the active agent in the vehicle and/or providing rapid dissolution of suspended particles to obtain a shorter $T_{max}$ (the time from dosing to reach the highest blood concentration of the active agent) and higher $C_{max}$ (the maximum blood concentration of the active agent; the concentration at $T_{max}$). In this way, a release profile is obtained that involves both rapid onset and rapid apparent elimination. By "immediate release" is meant that the at least 50%, preferably at least 75%, and most preferably at least 90%, of the solubilized active agent is released within 30 minutes at 37° C. as evaluated using standard USP dissolution test equipment (Apparatus 1 or Apparatus 2) described in USP 24-NF 19, Supplement 4, Section 71 1, published by the United States Pharmacopeia & National Formulary in 2001.

Another preferred release profile is characterized as having rapid onset, as above, but also provides for delayed and/or sustained release of some fraction of the active agent, such that some of the drug is not "immediately" released. The sustained and/or delayed release fraction, which is generally provided by the suspension fraction of the formulation, allows for a longer duration of action, eliminating or at least minimizing the need for repeated dosing.

If a slower onset or a more sustained plasma level of the active agent is desired, more of the active agent may be incorporated into the suspension fraction of the formulation than is solubilized, but a significant solubilized fraction should still be present so that the bioavailability of the active agent is not compromised. In many cases, the suspension can take advantage of the entire length of the intestines for complete absorption.

The suspended fraction of the active agents is in the form of a plurality of solid particles, which may associate to form one or more larger dosage units such as a granule, pellet, bead or tablet, suspended in the vehicle. The particles may be single phase, or comprised of two or more phases. When the solid particles are wholly comprised of the active agent, the particulate phase can be amorphous or in a high energy state, i.e., a metastable crystalline phase or a stable crystalline phase (wherein the crystalline state may include any of various polymorphs or solvates), or it may be a mixture of at least one amorphous phase and at least one crystalline phase. When the particles include one or more excipients, additives, or the like, the particulate material can be amorphous, crystalline, in the form of a solid solution with the excipient(s) and/or additive(s), or a mixture of two or more of these phases. The solid particles may contain a core comprised of the active agent, an excipient, or mixtures thereof, and may optionally be further coated with at least one layer of the active agent, the excipient, or mixtures thereof. The solid particles may be core-free, in the form of a powder or a plurality of granules, pellets, and/or beads, or combinations thereof.

Any high energy phase in the particulate fraction may contain a phase stabilizing agent. Suitable phase stabilizing agents are typically: (1) hydrophilic polymers selected from the group consisting of (a) polyalkylene oxides, e.g., polyethylene glycol or ethylene glycol-propylene glycol copolymers), (b) polyalkylene oxide-substituted $C_2$-$C_6$ diols and triols, e.g., mono-poly(oxyethylene)-substituted propylene glycol, di-(polyoxyethylene)-substituted propylene glycol, mono-poly(oxyethylene)-substituted glycerol, di-(polyoxyethylene)-substituted glycerol, and tri-(polyoxyethylene)-substituted glycerol, (c) polyalkylene oxide-substituted saccharides such as polyoxyethylated sorbitol, and polyoxyethylated glucose, (d) poly(N-vinyl lactams) such as polyvinyl pyrrolidone and poly(N-vinyl caprolactam), (e) acidic polymers and salts and esters thereof, such as vinyl polymers having pending carboxylic acid, sulfonic acid or phosphonic acid groups, optionally esterified, ionized by association with a base, or otherwise derivatized (e.g., polystyrene sulfonate) and (f) polymers of carboxyvinyl monomers such as acrylic acid, methacrylic acid, and/or esters thereof; (2) surfactants such as any of those described in Section IIIA above; (3) saccharides, including monosaccharides, disaccharides and polysaccharides and derivatives thereof (e.g., dextran sulfate), with cellulosic polymers (e.g., hydroxypropylmethylcellulose) preferred; (4) gelatins; and (5) inorganic salts such as sodium chloride. Particulate material in an amorphous state may also include any of the above phase stabilizing agents in groups (1) through (5).

Particle size distribution and surface properties can be critical factors affecting the release of the active agent from the particulate. In general, the smaller the particle size, the faster the release of the active agent, due to the larger total surface area available for dissolution and a higher surface-to-volume ratio. In addition, the more readily the surface of a particle is wetted, the faster the dissolution. To increase the release rate of the active agent from the suspended particles, various size reduction techniques can be applied. Typically, processes like grinding, milling, micronization, and nanosizing are well known in the art and can be utilized to obtain a mean particle size from several tens of micrometers to a tenth of a micrometer. Size reduction can be carried out in the presence of the vehicle, and/or in the presence of a surfactant, a hydrophilic polymer, a lipid, a gelatin, a saccharide, or a mixture thereof.

To modify the surface properties of the active agent particles, a surface coating of an interfacial modifying agent can be applied, wherein the interfacial modifying agent is as described above, i.e., selected from a surfactant, a hydrophilic polymer, a lipid, a gelatin, a saccharide, or a mixture thereof. Such agents may also be admixed with the particles (by, for example, co-grinding or co-micronizing), applied to the particles as a dry powder, and/or selected to chemically bind to the particle surface. If faster dissolution is desirable, the surface coating may be one that speeds wetting and comprises, for example, a hydrophilic surfactant, a sugar such as lactose, sucrose, or dextrose, or a hydrophilic polymer. If controlled release is desirable, e.g., sustained and/or delayed release, a suitable sustained and/or delayed release coating can be applied. Various pharmaceutically acceptable materials can be used for such coatings, including cellulose derivatives, polysaccharides, acrylic polymers, lipophilic surfactants, triglycerides, and mixtures thereof. Some of these materials can erode or dissolve slowly, whereas some do not dissolve in the acidic conditions of the stomach but will dissolve in the non-acidic conditions of the intestines. To further modify the release profile of an active agent from the solid particles, any of a variety of different particle preparation techniques may also be employed.

That is, particulates comprised of solid solutions, amorphous mixtures, fused mixtures, eutectic compositions, or mixtures thereof can be prepared with similar polymers, lipids, sugars, and any other pharmaceutically acceptable excipients. In addition, solid particles comprising a water-soluble complex of an active agent with a complexing agent, such as cyclodextrin or a derivative thereof, can also be utilized in the present invention. In general, the solid solution, amorphous mixture, fused mixture, or eutectic composition should dissolve faster than the crystalline active agent alone. To further modify the release profile of the active agent from the active agent particles, size reduction and surface coatings can be applied. For example, a eutectic mixture formed from an active agent and an excipient using a melting and cooling process can be ground into smaller particles. These particles can then be spray-coated with a polymer to modify their surface and consequently the dissolution profile of the active agent. Additional details regarding suitable particle preparation techniques are described in the following section.

The solid particulate material (i.e., that fraction of the active agent that does not become solubilized in the vehicle) may or may not be present in the same dosage form as the solubilized fraction of active agent. When the particulate fraction is present in the same dosage form as the solubilized fraction of the active agent, as illustrated in FIG. 1, the particles can be in direct contact with the vehicle solubilizing the active agent, such that the vehicle containing the suspended active agent particles also contains the solubilized fraction of the active agent. The suspended active agent may be in the form of particles individually suspended in the vehicle; see embodiment A of FIG. 1, illustrating the suspended particles as powder or larger pellets, granules, beads, or the like. Alternatively, the suspended active agent may be in the form of a larger dosage unit, such that the suspended "particles" are in association (e.g., compressed) to form at least one tablet, pellet, granule, or the like, and it is this larger dosage unit or units that are then suspended in the vehicle. See, e.g., embodiments C and D of FIG. 1.

Figure 2A:
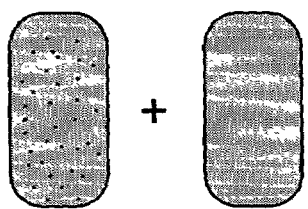
FIGS. 2A through 2D schematically alternative embodiments of the invention wherein the solubilized fraction of the drug and the remainder of the drug are incorporated into different dosage forms. Again, the shaded regions represent the solubilized fractions of the formulation, wherein the active agent is solubilized in the vehicle.
Figure 2B:
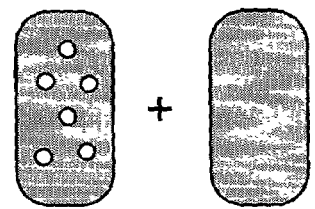
Figure 2C:
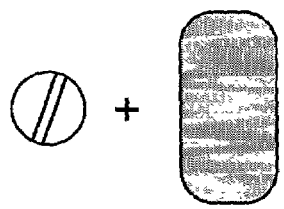
Figure 2D:
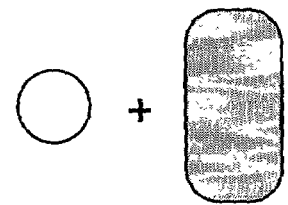

However, the solid particulate material and the solubilized fraction of active agent can also be present in separate dosage form (for concomitant or separate administration); see FIGS. 2A through 2D. In FIG. 2A, one capsule is shown as having suspended particulate material of very small particle size (e.g., powder) and the other capsule as containing solubilized drug. The embodiment of FIG. 2B is similar, except that the suspended particulate in the first dosage form is in the form of larger granules, pellets or beads. In FIGS. 2C and 2D, the non-solubilized fraction is a tablet or capsule, respectively.

If desired, the suspended and solubilized fractions of the active agent in a single dosage form can be segregated using any suitable separation means. One such means involves incorporating the suspended and solubilized fractions into discrete regions or compartments of the dosage form. For example, as illustrated in FIGS. 3A and 3B, a plug or a septum can be placed in a two-piece hard gelatin capsule to create two separate compartments, one containing the vehicle in which the active agent is solubilized, and the other containing the vehicle in which the active agent is suspended (again, in the form of particles or an aggregate thereof) Alternatively, as illustrated in FIGS. 4A, 4B and 4C, a wall or partition can also be inserted into a capsule during the manufacture of the capsule by providing a third gelatin ribbon in between the two shell ribbons to create two compartments as described above. A capsule may also be designed so that an interior capsule is wedged into an exterior capsule, leaving some space therebetween, so that the dosage form contains two segregated regions. See FIGS. 5A, 5B and 5C.

Other suitable separation means involves coating the suspended active agent particles or suspended active agent "aggregate" (e.g., tablet) with a layer of a material that is impermeable to the vehicle, such that the vehicle contains both the solubilized active agent and the suspended active agent coated with a vehicle-impermeable coating. See embodiment B of FIG. 1. Still another separation means involves the use of nested capsules, with a first, interior capsule containing particulate active agent (e.g., powder, granules, pellets, a compressed tablet), and a second capsule containing both the first capsule and an active agent-vehicle solution. The interior capsule may or may not be coated with a vehicle-impermeable coating to further ensure segregation of the active agent fractions. See embodiments B and D of FIG. 1.

V. Particle Manufacture:

The active agent particles can be manufactured using any of a wide variety of suitable techniques, including dry and wet granulation, pelletization, application of one or more coatings on an inert or active core, and the like. Commonly utilized coating and pelletization processes include balling, spheronization, extrusion, fusion, precipitation, co-precipitation, spray congealing, spray drying, pan coating, fluidized bed coating, melt extrusion, crystallization, cryopelletization, nanoencapsulation, coacervation, etc. Conventional, pharmaceutically acceptable additives can be introduced prior to or during particle manufacture to facilitate particle preparation, depending on the process, the active agent, and the nature of the final particulate material.

Coating processes preferably involve spraying a coating solution onto a substrate. The coating solution can be a molten solution of the encapsulation coat material, free of a dispersing medium. The coating solution can also be prepared by solubilizing or suspending the encapsulation coat material in an aqueous medium, an organic solvent, a supercritical fluid, or a mixture thereof. After the coating process is complete, the residual dispersing medium can be further removed to a desirable level utilizing appropriate drying processes, such as vacuum evaporation, heating, freeze drying, etc.

Pelletization typically involves preparation of a molten solution or a dispersion of the particulate solubilized or suspended in an aqueous medium, an organic solvent, a supercritical fluid, or a mixture thereof. Such a solution or dispersion is then extruded through an opening to achieve pellets of the desired shape, size, and other properties. As above, appropriate drying processes can be adopted to control the level of the residual dispersing medium, if necessary.

As is generally known, pellets, granules, and beads are formed with the aid of a pelletizer, spheronizer, or extruder. The pelletizer, spheronizer, or extruder is able to continuously form approximately spherical bodies from a mass of finely divided particles, by a rolling or tumbling action on a flat or curved surface with the addition of a liquid.

Pelletizers can be classified based on the angle of their axis as horizontal drum or inclined dish pelletizers. Rotary fluidized granulators can also be used for pelletization. A standard fluidized drier bowl can be replaced with a rotating plate as an air distributor. For granulation, a binder liquid is sprayed from via one or two binary nozzles located axially to the rotational movement of the powder bed. This operation results in rounding of the granules to approximately spherical pellets. Such balling or agitation techniques can be influenced by operating conditions, such as bridging/binding liquid requirements, residence time of the material in the pelletizer, speed and angle of inclination of the pelletizer, amount of material fed to the pelletizer, choice and levels of binder, etc. One skilled in the art can readily adjust such factors to produce a satisfactory product.

The components of the present formulations can also be self-binding. Liquid components can be pelletized with the aid of suitable solidifying, binding, or thickening agents.

The choice of an appropriate binder for a given application may be readily determined by one of ordinary skill in the art. At a minimum, the binder must be capable of wetting the surfaces of the particle being pelletized or granulated. Binders must have sufficient wet strength to allow agglomerates to be handled, and sufficient dry strength to make them suitable for their intended purposes. Each process, however, makes use of a different system of forces and may require a different agglomerate strength. The final selection of the binder should be made on the basis of the type of equipment that is used. The size and size distribution of pellets, bulk density, strength, and flow properties also affect the performance of the pellets, and these properties can be adjusted by one skilled in the art by the inclusion of additives, choice of equipment, and processing conditions.

Extrusion: Extrusion is a well-known method of applying pressure to a damp or melted composition until it flows through an orifice or a defined opening. The extrudable length varies with the physical characteristics of the material to be extruded, the method of extrusion, and the process of manipulation of the particles after extrusion. Various types of extrusion devices can be employed, such as screw, sieve and basket, roll, and ram extruders.

Encapsulation by Extrusion: In this method, the particles' components are added to a low moisture melt of a saccharide, e.g., a low maltodextrin (or sucrose or modified edible starch), mixed and extruded into a cold bath. The solidified composition can be further ground down. Optionally, centrifugal extrusion can be utilized for efficiency.

Melt Extrusion: The active agent particles can also be melted and extruded with a continuous, solvent-free extrusion process, with or without inclusion of additives.

Spheronization: Spheronization, as the term suggests, is the process of converting material into spheres, the particle shape having the lowest ratio of surface area to volume. Spheronization typically begins with damp extruded particles. The extruded particles are broken into uniform lengths and gradually transformed into spherical shapes. In addition, powdered raw materials, which require addition of either liquid or material from a mixer, can be processed in an air-assisted spheronizer.

Disk Spinning: Spinning disk technology involves formation of particles from either a molten or solubilized composition sprayed onto a rotating disc maintained at a predetermined temperature and rotating at a predetermined speed. When a molten composition contacts the spinning disk, particles congeal, while with a liquid composition, the liquid rapidly evaporates from the solution resulting in formation of solid drug particles. The composition may or may not contain various inert excipients and additives in addition to the active agent or agents. As will be appreciated by those of ordinary skill in the art, the temperature of the disc and its rotation may be adjusted to produce particles of predetermined size and shape.

Spray Congealing: Spray congealing is process in which a substance of interest is allowed to melt, disperse, or dissolve in a hot melt of other additives, and is then sprayed into an air chamber wherein the temperature is below the melting point of the formulation components, to provide spherical congealed pellets. The air removes the latent heat of fusion. The temperature of the cooled air used depends on the freezing point of the product. Due to the absence of solvent evaporation in most spray congealing processes, the particles are generally nonporous and strong, and remain intact upon agitation. The characteristics of the final congealed product depend in part on the properties of the additives used. The feeding rate and inlet/outlet temperatures are adjusted to ensure congealing of the atomized liquid droplet. The feed should have adequate viscosity to ensure homogeneity. The conversion of molten feed into powder is a single, continuous step. Proper atomization and a controlled cooling rate are critical to obtain high surface area, uniform and homogeneous congealed pellets. Adjustment of these parameters is readily achieved by one skilled in the art. Spray congealing can, for example, be used to produce free-flowing powders from liquids and pellets ranging in size from about 0.25 to 2.0 mm.

The spray congealing method is particularly suitable for heating labile substances (since the ambient temperature is used for drying) and for moisture sensitive substances (since non-aqueous compositions can be utilized). Spray congealing is similar to spray drying, except that no solvent is utilized. Spray congealing is a uniform and rapid process, and is completed before the product comes in contact with any equipment surface. Most additives and active agents that are solid at room temperature and melt without decomposition are suitable for use with this method.

Conventional spray dryers operating with cool inlet air have been used for spray congealing. Several methods of atomizing molten materials can be employed, such as pressure, pneumatic, or centrifugal atomization. For persons skilled in the spray congealing art, it is well known that several formulation aspects (such as matrix materials and viscosity) and processing factors (such as temperature, atomization, and cooling rate) affect the quality (morphology, particle size distribution, polymorphism, and dissolution characteristics) of spray-congealed pellets. The spray-congealed particles can be used in tablets or capsules, or they can be incorporated into a liquid suspension form.

Solvent Dehydration (Spray Drying): For compositions that are oily in nature, the spray drying technique is commonly employed. The oily material is commonly mixed with a polymeric material, such as gelatin, vegetable gum, modified starch, dextrin, or other appropriate additives. An emulsifier is added, if needed, to form an oil-in-water emulsion. The emulsion is atomized into a column of heated air in a drying chamber, resulting in rapid evaporation of water. Alternatively, the emulsion is atomized directly into a non-aqueous polar solvent, such as isopropanol, ethanol, glycerol, or polyglycols, to dehydrate the aerosolized particle. This method is particularly suitable for compositions containing a lipophilic active agent or additives that result in lipophilic cores. Spray drying/solvent dehydration can also be applied to hydrophilic active agents or additives to form an oil-in-water emulsion, which is spray dried. This results in a homogenous solid composition. Furthermore, water or organic solvent-based formulations can be spray dried using an inert process gas, such as nitrogen, argon, or the like.

Crystallization: Components of the present invention can be dissolved in appropriate solvents and subjected to spherical crystallization techniques well known in the art.

Nanoencapsulation: Nanoencapsulation involves solubilizing an aqueous solution of an active agent and other components in a weakly polar vehicle. Micelles are formed with the active in an organic outer phase. Then, an amphiphilic monomer is added to the lipophilic external phase. The mixed micelles thus formed are then polymerized with the aid of a suitable procedure, such as UV or gamma radiation, heat, or chemical agents. The hardened solidified micelles are made to undergo phase exchange by replacing an outer lipophilic vehicle by water. By selecting appropriate monomers, networking agents, and auxiliary materials, nanocapsules as small as 80 to 250 nm can be prepared.

Precipitation by Anti-Solvent: A solution of active agent and optionally other excipients in a solvent, preferably a volatile one, is mixed with an anti-solvent that has significantly lower solubility for the formulation components than does the solvent. As a result, the active agent precipitates out, together with excipients if present. The precipitate can be collected and subjected to further processes, such as size reduction. A pure precipitate of the active agent can be obtained from a solvent if no excipients are present.

Supercritical Fluid Processes: Components of the present invention can be dispersed in a supercritical fluid and crystallized as needed. Current techniques involving supercritical fluids include precipitation by rapid expansion of supercritical solutions, gas anti-solvent processes, and precipitation from gas-saturated solutions.

Coacervation: Coacervation is a transfer of macromolecules with film properties from a solvated state in a coacervation phase into a phase in which there is a film around each particle. The coacervation method involves dispersing the composition in a dispersion of a polymeric colloid, such as gelatin alginate, and shock treating the mixture will temperature or pH, etc., to generate a two-phase system. The desired phase is then hardened with a cross-linking agent, such as glutaraldehyde.

Cryopelletization: The cryopelletization procedure allows conversion of a molten mass, aqueous solution, or suspension into solid, bead-like particles. The molten mass solutions or suspensions are dripped by means of an appropriately designed device into liquid nitrogen. The production of small drops and liquid nitrogen cooling permit very rapid and uniform freezing of the material processed. The pellets are further dried in conventional freeze dryers. Cryopelletization can also be carried out under aseptic conditions for sterile processing. The most critical step in producing spherical particles by this process is droplet formation. Droplet formation is influenced by formulation related variables, such as the nature of the active agent and additives, viscosity, total solid content, surface tension, etc. Extra care must be undertaken with the processing of suspensions to ensure homogeneity. In addition, equipment design and processing variables also play an important role. One skilled in the art can readily balance the various factors to produce a satisfactory product. Enteric matrix pellets can be formed that include polyacrylic acid (e.g. Carbopol) with a high molecular weight polyethylene glycol (such as PEG-20, 000).

Other processes suitable for producing solid pharmaceutical compositions of the present invention include extrusion and spray chilling. These processes are described in detail in U.S. Pat. Nos. 5,965,161 and 5,539,000 respectively, the disclosures of which are incorporated herein by reference.

For processing of encapsulated compositions, various methods can be used. The term "microencapsulation" applies to enclosure or encasement in microcapsules. Microencapsulation is a means of applying coatings to small particles of solids or droplets of liquids and dispersions. The terms "coated," "protected," or "layered" are commonly used interchangeably with the term "encapsulated". All of these terms can be used to refer to practically any core material that is encased or enclosed in an outer shell. Typical equipment used to apply coating includes a conventional pan (Pellegrini; Italy), a modified perforated pan (multicoater, Thomas Eng., IL) or a Wurster coater in a Glatt powder coater/granulator (Glatt Airtechniques).

Solvent Based Solution Coating: Solvent-based coating uses coating materials that are solubilized and/or dispersed in a solvent. The solvent can be aqueous or non-aqueous. When the solvent is aqueous-based, the components can be emulsified with an appropriate emulsifier, organic solvent, or a supercritical fluid. Solvents with a lower melting point than water and higher vapor pressures are preferred. Solvent mixtures with other organic solvents or water are often employed to achieve appropriate viscosity and component solubilization. Typical solvents include ethanol, methanol, isopropanol, acetone, dichloromethane, trichloromethane, and ethyl acetate. Appropriate polymers can also be added as needed. Cellulosic derivatives and polymethacrylates are particularly suitable additives for organic solvent coating. Dissolution and solubilization of the components is facilitated by rigorous stirring or heating. Plasticizers may be also be added to stimulate dissolution. Colorants and antisticking agents can be employed as needed.

Substrate surface area, shape, porosity, and stability are important determinants of good coating. Spherical particles are preferred, and these may be produced through spheronization or a spherical crystallization process. Crystals or compact granules from dry compaction or extrusion processes, often available commercially, serve as good substrates.

Encapsulation can be conducted by traditional pan coating or fluidized bed techniques. Several process factors (air supply, temperature, spray rate, spray system, powder feed, attrition) and formulation factors determine the quality of the end product, and one skilled in the art can readily adjust such parameters as needed.

Air suspension in a rotary fluidized bed granulator can be used to deposit the encapsulation coat on to a substrate, thus allowing a high rate of coating application with low coating loss. Furthermore, both aqueous and organic solvents can be used. The Wurster process, an air suspension technique, is more suitable for encapsulations involving very fine powders.

Solvent-Free Coating: This process entails using coating materials that can be applied in a molten state. The selection of proper coating materials depends on melting point, melting point range, and the viscosity in the liquid state. A fluidized bed is ideal for molten coatings of substrates that range from about 100 micrometers to about 2000 micrometers in size. Fluidized bed coating using sprayed molten materials involves achieving a proper balance of process parameters that allow proper encapsulation to occur. Substrate particles that are suspended and separated from each other by the fluidization air enter a zone of finely atomized coating liquid. Coating occurs as the liquid droplets, which are substantially smaller in size than the substrate, impact the particles, spread, and solidify. Multiple layers can be coated, and the completion of spraying is followed by a product stabilization or cooling step. Some critical success parameters include bed temperature, atomization, atomization fluid temperature, droplet size, spray type, spray rate, rate of coating droplet solidification on particle surfaces, particle size, shape, etc. Inert materials such as sodium chloride, citric acid, and potassium chloride can serve as substrates. One skilled in the art can readily adjust such parameters to achieve a satisfactory product.

The processes described above are suitable for producing substrate-based particles or non-substrate-based particles. In the latter case, the particulate material does not include any seed particle (e.g., a conventional drug or other additive aggregate starch or sugar bead). Instead, the compositions are processed, and the components are chosen, such that a solid composition is formed without need for a substrate bead. The particles formed can be in the form of beadlets, beads, granules, pellets, etc., that have an approximately homogenous distribution. These particulates can be produced by means of balling in pelletizers or fluid bed granulators, and compaction or extrusion/ spheronization. In addition, these particulates can be produced using solvent-free spray congealing processes or dropping (globulization) methods. Dropping procedures involve conversion of aqueous solutions or suspensions to a solid form. Congealing of the liquid droplets in cooling baths can be aided by a chemical reaction (e.g., insoluble salt or complex formation), a sol/gel transition, or by freezing in a coolant bath of liquid nitrogen or halogenated hydrocarbons.

VI. Stabilizing Agents:

The formulations of the present invention optionally include one or more stabilizing agents to increase the stability and/or compatibility of the suspension when formulated into a dosage form. Suitable stabilizing agents are suspending agents, flocculating agents, thickening agents, gelling agents, buffering agents, antioxidants, preservatives, antimicrobial agents, and mixtures thereof. Ideally, the agent acts to minimize irreversible aggregation of suspended particles, and to maintain proper flow characteristics to ease manufacturing processes, e.g., to ensure that the formulation can be readily pumped and filled into desired dosage forms, such as capsules. In some instances, however, it may be desirable that the formulation have a high viscosity, so that no leakage will occur before a capsule or other dosage form is permanently sealed.

A preferred stabilizing agent in most cases is a suspending agent that imparts increased viscosity and retards sedimentation, to prevent caking. Any pharmaceutically acceptable excipient with such attributes, of the many well known in the art, can be used as such a suspending agent. Suitable suspending agents include cellulose derivatives, clays, natural gums, synthetic gums, or other agents known in the art. Specific suspending agents, by way of example, include microcrystalline cellulose, sodium carboxymethylcellulose, powdered cellulose, ethymethylcellulose, hydroyxypropyl methylcellulose, methylcellulose, ethylcellulose, ethylhydroxy ethylcellulose, hydroxypropyl cellulose, attapulgite, bentonite, hectorite, montmorillonite, silica gel, fumed silicon dioxide, colloidal silicon dioxide, acacia, agar, carrageenan, guar gum, locust bean gum, pectin, sodium alginate, propylene glycol alginate, tamarind gum, xanthan gum, carbomer, povidone, sodium starch glycolate, starches, tragacanth, magnesium aluminum silicate, aluminum silicate, magnesium silicate, gelatin, and glycyrrhizin. These suspending agents can further impart different flow properties to the suspension. The flow properties of the suspension can be Newtonian, plastic, pseudoplastic, thixotropic or combinations thereof. Mixtures of suspending agents may also be used to optimize flow properties and viscosity.

The stabilizing agent may also be a flocculating agent that enables particles to associate in loose aggregates or "flocs." Although these flocs may settle rapidly, they are easily redispersed. Many flocculating agents known in the art can be utilized, including surfactants, hydrophilic polymers, clays, and electrolytes. Any other pharmaceutically acceptable excipient with such attributes can also be utilized as a flocculating agent. In some cases, the flocculating agent may serve a dual purpose, serving not only as a stabilizing agent but also, for example, as a component of the solid particles or as a suspending agent. Suitable flocculating agents include, but are not limited to, sodium lauryl sulfate, sodium docusate, benzalkonium chloride, polysorbate 80, sorbitan monolaurate, sodium carboxymethylcellulose, xanthan gum, tragacanth, methylcellulose, magnesium aluminum silicate, attapulgite, bentonite, potassium dihydrogen phosphate, aluminum chloride, and sodium chloride. The formulation may include both a flocculating agent and a suspending agent, so that the sedimentation of flocs can be retarded.

The stabilizing agent may also be a thickening agent, selected to increase the viscosity of the suspension to a degree sufficient to reduce and retard sedimentation of suspended active agent particles. Any pharmaceutically acceptable excipient with such attributes can be used in the present invention. Typically, compounds that soften slightly above ambient temperature are desirable for this purpose. Preferred thickening agents have a melting point greater than about 25° C., and can be reversibly liquified and solidified. With an appropriate amount of such a thickening agent, the formulation as a whole can acquire this thermosoftening property.

The formulations of the invention preferably provide for immediate release of that fraction of the active agent that is solubilized in the vehicle, such that the active agent is immediately available for absorption following administration to a patient. Therefore, it is preferred that the stabilized suspension remain readily water-dispersible at a temperature around body temperature, so that a rapid release of the solubilized fraction of the active agent can be achieved. Accordingly, preferred stabilizing agents are not only able to suspend, flocculate, and/or thicken the formulation, but also capable of facilitating release of the active agent. Hydrophilic polymers, hydrophilic surfactants with a melting point greater than about 25° C., or mixtures thereof are particularly useful in this regard.

However, it is also preferred that the formulation be substantially free of any water-indispersible suspending/thickening agent, so that the overall water dispersibility of the suspension is not compromised. Accordingly, the formulation should be substantially free of materials such as beeswax, paraffin, yellow wax, hydrogenated oils, hydrogenated vegetable oil, hydrogenated soybean oil flakes, and other similar water-indispersible waxy materials having a melting point greater than about 50° C. By "substantially free" of water-indispersible materials, e.g., "substantially wax-free," is meant that any such materials represent less than 5 wt. % of the formulation, preferably less than 3 wt. %, more preferably less than about 1 wt. %.

The stabilizing agent may also be a buffering agent, an antioxidant, or a preservative, and mixtures thereof.

Although optional, stabilizing agents are preferred components of the present formulations, providing a number of advantages as described above. In particular, preferred agents are used to form thixotropic (shear thinning) formulations, so that the active agent particles can remain in suspension for an extended time period, while at the same time providing compositions that are readily processable for encapsulation procedures or the like. Other preferred stabilizing agents give rise to thermosoftening preparations, which, as noted above, are advantageous in that they can be reversibly liquified at the capsule filling temperature, and then solidified at the storage temperature, to provide good manufacturability and stability. Most preferred are formulations containing one or more stabilizing agents that provide the formulations with both thixotropic and thermosoftening properties.

VII. Other additives:

Other additives conventionally used in pharmaceutical compositions can be included, and these additives are well known in the art. Such additives include detackifiers, antifoaming agents, chelating agents, tonicifiers, flavorants, colorants, odorants, opacifiers, binders, fillers, plasticizers, taste-masking agents, lubricants, and mixtures thereof. The amounts of such additives can be readily determined by one skilled in the art, according to the particular properties desired.

The formulations may also include one or more enzyme inhibitors, as described in commonly assigned U.S. Pat. No. 6,309,633 to Patel et al.; see also A. Bemskop-Schnurch (1998), "The use of inhibitory agents to overcome enzymatic barriers to perorally administered therapeutic peptides and proteins," *J. Controlled Release* 52:1-16. Suitable inhibitors may function as either competitive or noncompetitive inhibitors. Generally, enzyme inhibitors can be divided into the following classes: inhibitors that are not based on amino acids, such as p-aminobenzamidine, FK-448 (4-(4-isopropyl-piperazinocarbonyl)phenyl 1,2,3,4-tetrahydro-1-naphthoate methanesulfonate), camostat mesylate, and sodium glycocholate; amino acids and modified amino acids, such as aminoboronic acid derivatives and n-acetyl-cysteine; peptides and modified peptides, such as bacitracin, phosphinic acid dipeptide derivatives, pepstatin, antipain, leupeptin, chymostatin, elastatin, bestatin, phosphoramindon, puromycin, cytochalasin potatocarboxy peptidase inhibitor, and amastatin; polypeptide protease inhibitors, such as aprotinin (bovine pancreatic trypsin inhibitor), Bowman-Birk inhibitor and soybean trypsin inhibitor, chicken egg white trypsin inhibitor, chicken ovoinhibitor, and human pancreatic trypsin inhibitor; complexing agents, such as EDTA, EGTA, 1,10-phenanthroline and hydroxychinoline; and mucoadhesive polymers and polymer-inhibitor conjugates, such as polyacrylate derivatives, chitosan, cellulosics, chitosan-EDTA, chitosan-EDTA-antipain, polyacrylic acid-bacitracin, carboxymethyl cellulose-pepstatin, and polyacrylic acid-Bowman-Birk inhibitor.

The selection and amount of any enzyme inhibitor will depend on toxicity, specificity, and potency.

The formulations may also include an absorption promoter, which can facilitate the absorption of active agent released, particularly suspended active agent. Accordingly, in one alternative embodiment of the invention, part or all of the solubilized drug fraction may be replaced by an absorption promoter. Suitable absorption promoters are described, for example, in co-pending U.S. patent application Ser. No. 09/751,968 to Chen et al. for "Pharmaceutical Dosage Forms for Oral Administration of Hydrophilic Drugs, Particularly Low Molecular Weight Heparin," filed Dec. 29, 2000 and assigned to Lipocine, Inc. (Salt Lake City, Utah), published on Sep. 27, 2001 under Publication No. 20010024658. The absorption enhancers described in commonly assigned U.S. Pat. No. 6,309,633 to Patel et al. may also serve as suitable absorption promoters in the present compositions and systems.

Preferred absorption promoters are bile acids and bile salts. As well known in the art, bile acids are naturally occurring surfactants having a nucleus derived from cholanic acid and are substituted with a 3α-hydroxyl group and optionally with other hydroxyl groups as well, typically at the $C_6$, $C_7$ or $C_{12}$ position of the sterol nucleus. Bile acids include, for example, cholic acid, deoxycholic acid, lithocholic acid, chenodeoxycholic acid (also referred to as "chenodiol" or "chenic acid"), and ursodeoxycholic acid. The aforementioned acids are "unconjugated" bile acids in that the carboxyl group extending from the $C_{17}$ position of the sterol nucleus is in free acid form. Bile acids may also be "conjugated," typically by reaction of the aforementioned carboxyl group with the free amine moiety of glycine ($H_2NCH_2COOH$) or taurine ($H_2NCH_2CH_2SO_3H$) to form a peptide linkage. Conjugated bile acids thus include, for example, taurocholic acid, taurodeoxycholic acid, taurolithocholic acid, taurochenodeoxycholic acid, tauroursodeoxycholic acid, glycocholic acid, glycodeoxycholic acid, glycolithocholic acid, glycochenodeoxycholic acid, and glycoursodeoxycholic acid. Any of the aforementioned bile acids can be advantageously used in conjunction with the present invention. The bile acids may also be in the form of a salt, in which case the acidic functionality is ionized and associated with a cationic counter-ion, e.g., sodium, potassium, ammonium, or the like. In addition, the bile acids herein may be in the form of a choleic acid, wherein a bile acid forms a coordination complex with another compound, typically although not necessarily a fatty acid.

Particularly preferred bile acids for use herein are ursodeoxycholic acid and chenodeoxycholic acid, and when used in the salt form, the sodium salt is particularly preferred.

It will be appreciated by those of skill in the art that bile "acids" and bile "salts herein are interchangeable, in that the form of the compound will depend on the pH of the surrounding environment. That is, at lower pH, a bile acid will be in the form of the free acid, while at higher pH, the salt form will predominate.

The bile salt or acid in the present compositions and dosage forms may be an integral part of the formulation (e.g., included in the vehicle), or it may represent a coating on a dosage form, e.g., on a capsule, tablet, or caplet, or on each of a plurality of granules, beads, or pellets. The bile salt or acid may take any number of physical forms, e.g., it may be in crystalline, amorphous, nanosized, micronized or milled form.

VIII. Dosage Forms and Administration Routes:

The pharmaceutical compositions and systems of the present invention are preferably formulated for oral administration, although other modes of administration are contemplated as well. For oral administration, the suspension can be formulated as a liquid or solid (e.g., powdered) concentrate, or as an aqueous or organic diluted concentrate. In the diluted form, the diluent can be water, an aqueous solution, a buffer, an organic solvent, a beverage, a juice, or mixtures thereof. If desired, the diluent can include components dissolved or suspended therein, such as an active agent, an enzyme inhibitor, solubilizers, additives, and the like.

In a preferred embodiment, the oral dosage form is comprised of an encapsulated composition, wherein the pharmaceutical formulation is typically contained in a capsule. The capsule can be a hard or soft gelatin capsule, a starch capsule, or a cellulosic capsule. For a two-piece capsule, the capsule can be further sealed either by a banding or a spray sealing mechanism after filling with the suspension formulation. Such dosage forms (as well as other solid dosage forms, such as tablets, caplets, granules, pellets, and beads) can further be coated with, for example, a seal coating, an enteric coating, an extended release coating, a targeted delayed release coating, a film coating, a barrier coating, a compressed coating, a fast disintegrating coating, or an enzyme degradable coating. As a result, the dosage form can be designed for immediate release, controlled release, extended release, delayed release, targeted release, synchronized release, or targeted delayed release. Multicompartment capsules can also be utilized for multi-stage release or pulsatile release of one or more than one active agent. Different active agents can be mixed or separated in different compartments such that they can be released at different stages or released according to different profiles. Multiple coatings can be applied for a desired performance.

The formulations of the invention can also be formulated as an osmosis-based dosage form for oral administration or for implants. The osmosis-based dosage form can be an osmotic capsule or an osmotic tablet filled with the suspension formulation. Different coatings can further be applied to the capsule or tablet depending on the administration routes and desired release profile of the active agent.

These various coatings are known in the art, but for clarity, the following brief descriptions are provided:

Seal coating, or coating with isolation layers: Thin layers of up to 20 micrometers in thickness can be applied for variety of reasons, including particle porosity reduction, to reduce dust, for chemical protection, to mask taste, to reduce odor, to minimize gastrointestinal irritation, etc. The isolating effect is proportional to the thickness of the coating. Water-soluble cellulose ethers are preferred for this application. Hydroxypropyl methyl cellulose and ethyl cellulose in combination, or Eudragit E100, may be particularly suitable for taste-masking applications. Such coating materials can also be applied to form an isolating layer.

Extended Release Coating: The term "extended release coating" as used herein means a coating designed to effect delivery over an extended period of time. Preferably, the extended release coating is a pH-independent coating formed of, for example, ethyl cellulose, hydroxypropyl cellulose, methylcellulose, hydroxymethyl cellulose, hydroxyethyl cellulose, acrylic esters, or sodium carboxymethyl cellulose. Various extended release dosage forms can be readily designed by one skilled in the art to achieve delivery to both the small and large intestines, to only the small intestine, or to only the large intestine, depending upon the choice of coating materials and/or coating thickness.

Enteric Coating: The term "enteric coating" as used herein relates to a mixture of pharmaceutically acceptable excipients that is applied to, combined with, mixed with, or otherwise added to the carrier or composition. The coating may be applied to a compressed, molded, or extruded tablet; a capsule; and/or pellets, beads, granules or particles of the carrier or composition. The coating may be applied through an aqueous dispersion or after dissolving in appropriate solvent. Additional additives and their levels, and selection of a primary coating material or materials, will depend on the following properties: resistance to dissolution and disintegration in the stomach; impermeability to gastric fluids and drugs/carriers/enzymes while in the stomach; ability to dissolve or disintegrate rapidly at the target intestine site; physical and chemical stability during storage; lack of toxicity; ease of application as a coating; and economical practicality.

Delayed release formulations herein enable drug release at some generally predictable location in the lower intestinal tract more distal to that which would have been accomplished if there had been no delayed release feature. The preferred method for delay of release is coating. Such coatings should be applied at a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention to achieve delivery to the lower gastrointestinal tract. The preferred polymers for use in the present invention are anionic carboxylic polymers. The more preferred polymers and compatible mixtures thereof, and some of their properties, include, but are not limited to:

Shellac, also called purified lac, a refined product obtained from the resinous secretion of an insect. This coating dissolves in media of pH>7.

Acrylic polymers (preferred). The performance of acrylic polymers (primarily their solubility in biological fluids) can vary based on the degree and type of substitution. Examples of suitable acrylic polymers include methacrylic acid copolymers and ammonio methacrylate copolymers. The Eudragit® series E, L, S, RL, RS, and NE (Rohm Pharma) are available solubilized in organic solvent, aqueous dispersion, or dry powders. The Eudragit® series RL, NE, and RS are insoluble in the gastrointestinal tract but are permeable and are used primarily for extended release. The Eudragit® series E dissolve in the stomach. The Eudragit® series L, L-30D, and S are insoluble in the stomach and dissolve in the intestine.

Cellulose Derivatives (also preferred). Examples of suitable cellulose derivatives are ethyl cellulose and reaction mixtures of partial acetate esters of cellulose with phthalic anhydride. The performance can vary based on the degree and type of substitution. Cellulose acetate phthalate (CAP) dissolves in pH>6. Aquateric® (FMC) is an aqueous-based system and is a spray dried CAP psuedolatex with particles <1 µm. Other components in Aquateric can include pluronics, Tweens, and acetylated monoglycerides. Other examples of suitable cellulose derivatives are cellulose acetate trimellitate (Eastman); methylcellulose (Pharmacoat®, Methocel®); hydroxypropyl methyl cellulose phthalate (HPMCP; the performance can vary based on the degree and type of substitution; HP-50, HP-55, HP-55S, HP-55F grades are suitable); hydroxypropyl methyl cellulose succinate (HPMCS; available as Aqoate from Shin Etsu); the performance can vary based on the degree and type of substitution; suitable grades include AS-LG (LF), which dissolves at pH 5, AS-MG (MF), which dissolves at pH 5.5, and AS-HG (HF), which dissolves at higher pH; these polymers are offered as granules, or as fine powders for aqueous dispersions); and polyvinyl acetate phthalate (PVAP, which dissolves in pH>5, and it is much less permeable to water vapor and gastric fluids). Combinations of the above materials can also be used.

The coating can, and usually does, contain a plasticizer and possibly other coating excipients such as colorants, talc, and/or magnesium stearate, which are well known in the art. Suitable plasticizers include: triethyl citrate (Citroflex® 2), triacetin (glyceryl triacetate), acetyl triethyl citrate (Citroflex® A-2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually will contain 10-25% by weight of a plasticizer, especially dibutyl phthalate, polyethylene glycol, triethyl citrate, and triacetin. Conventional coating techniques such as spray or pan coating are employed to apply coatings. The coating thickness must be sufficient to ensure that the oral dosage form remains intact until the desired site of topical delivery in the lower intestinal tract is reached.

Colorants, detackifiers, surfactants, antifoaming agents, lubricants, stabilizers (such as hydroxy propyl cellulose), acids, or bases may be added to the coatings in addition to plasticizers to solubilize or disperse the coating material and to improve coating performance.

A particularly suitable methacrylic copolymer is Eudragit L, particularly L-30D and L-100-55, manufactured by Rohm Pharma, Germany. In Eudragit L-30 D, the ratio of free carboxyl groups to ester groups is approximately 1:1. Further, the copolymer is known to be insoluble in gastrointestinal fluids having pH below 5.5, generally 1.5-5.5 (i.e., the pH generally present in the fluid of the upper gastrointestinal tract), but is readily soluble or partially soluble at pH above 5.5 (i.e., the pH generally present in the fluid of lower gastrointestinal tract).

Another methacrylic acid polymer that is suitable for use in coating the composition or solid carrier, which can be employed in the compositions and methods described herein, either alone or in combination with other coatings, is Eudragit S, manufactured by Rohm Pharma, Germany. Eudragit S differs from Eudragit L-30-D only insofar as the ratio of free carboxyl groups to ester groups is approximately 1:2. Eudragit S is insoluble at pH below 5.5, but unlike Eudragit L-30-D, is poorly soluble in gastrointestinal fluids having pH of 5.5-7.0, such as is present in the small intestine fluids. This copolymer is soluble at pH 7.0 and above (i.e., the pH generally found in the colon). Eudragit S can be used alone as a coating to provide delivery beginning at the large intestine via a delayed release mechanism. In addition, Eudragit S, being poorly soluble in intestinal fluids below pH 7, can be used in combination with Eudragit L-30-D, which is soluble in intestinal fluids above pH 5.5, in order to effect a delayed release composition. The more Eudragit L-30 D used, the more proximal the release and delivery begins, and the more Eudragit S used, the more distal the release and delivery begins Both Eudragit L-30-D and Eudragit S can be substituted with other pharmaceutically acceptable polymers that have similar pH solubility characteristics.

Preferred coating materials include shellac, acrylic polymers, cellulosic derivatives, polyvinyl acetate phthalate, and mixtures thereof. More preferred materials include Eudragit series E, L, S, RL, RS, NE, L, L300, S, and 100-55, cellulose acetate phthalate (including that commercially available as Aquateric®), cellulose acetate trimellitate, ethyl cellulose, hydroxypropyl methyl cellulose phthalate, hydroxypropyl methyl cellulose succinate, and polyvinyl acetate phthalate (including that commercially available from Colorcon as Sureteric®). Most preferred materials include Eudragit series L, L300, S, and Li00-55, cellulose acetate phthalate, ethyl cellulose, hydroxypropyl methyl cellulose phthalate, hydroxypropyl methyl cellulose succinate, and polyvinyl acetate phthalate.

Extended release and targeted delayed release coatings for dosage forms of the four compositions of the present invention are described more completely in U.S. Pat. Nos. 5,622,721 and 5,686,105, the disclosures of which are incorporated herein by reference.

Fast-Disintegrating Coatings for Immediate Release: An immediate release coating is commonly used to improve product appearance as well as to provide a moisture barrier and for taste and odor masking. Rapid breakdown of the film in gastric fluids is necessary, leading to rapid disintegration and dissolution. Eudragit RD100 (Rohm) is an example of such a coating. It is a combination of a water-insoluble cationic methacrylate copolymer with water-soluble cellulose ether. In powder form, it is readily dispensable into an easily sprayable suspension that dries to leave a smooth film. Such films rapidly disintegrate in aqueous media at a rate that is independent of pH and film thickness.

Although the compositions of the present invention are specifically suited to oral administration, which is presently preferred, they can also be formulated as injectable dosage forms for intravenous, intramuscular, subcutaneous, and intraperitoneal administration. The compositions of the present invention can also be formulated for topical, transdermal, buccal, ocular, pulmonary, vaginal, rectal, transmucosal, or other modes of administration.

The formulations of the present invention can be further processed according to conventional processes known to those skilled in the art. Such processes include, without limitation, lyophilization, encapsulation, compression, melting, extrusion, drying, chilling, molding, spraying, coating, comminution, mixing, homogenization, sonication, and granulation, to produce a desired dosage form. Upon administration or upon dispersion, the further-processed composition can be reconstituted back to the suspension formulation. Alternatively, the suspension can be reconstituted prior to administration. The compositions of the present invention are not limited to particular solid dosage forms. Thus, compositions of the present invention can be formulated as, for example, pills, capsules, caplets, tablets, granules, beads, pellets, or powders. Granules, beads, and powders can, of course, be further processed to form pills, capsules, caplets, or tablets.

It is to be understood that while the invention has been described in conjunction with the preferred specific embodiments thereof, the foregoing description as well as the examples that follow are intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

Experimental

The practice of the present invention will employ, unless otherwise indicated, conventional techniques and equipment used in the fields of pharmaceutical formulation and drug delivery, which are within the skill of the art and described in the pertinent texts and literature. See, for example, *Remington: The Science and Practice of Pharmacy, Nineteenth Ed.* (Easton, Pa.: Mack Publishing Company, 1995). In the following examples, efforts have been made to ensure accuracy with respect to numbers used (e.g., amounts, temperatures, etc.) but some experimental error and deviation should be accounted for. Unless otherwise indicated, temperature is in degrees Celsius and pressure is at or near atmospheric pressure at sea level. All reagents were obtained commercially unless otherwise indicated.

Also, in these examples, the tradenames used are as follows:

Capryol® 90=propylene glycol monocaprylate, a lipophilic surfactant (Gattefosse);

Captex® 810D=glycerol tricaprylate/caprate/linoleate, a triglyceride composition (Abitec);

Cremophor® EL=PEG-35 castor oil, a hydrophilic surfactant (BASF);

Cremophor® RH40=PEG-40 hydrogenated castor oil, a hydrophilic surfactant (BASF);

Gelucire® 44/14=lauroyl macrogol-32 glyceride, including triglycerides (Gattefosse);

Etocas® 35=PEG-35 castor oil, a hydrophilic surfactant (Croda);

Imwitor® 742=an esterification product of a mixture of approximately 60 parts by weight (ppw) of caprylic acid and approximately 40 parts by weight (ppw) of capric acid with glycerol, a lipophilic surfactant (Hüls);

Kollidon® K17=polyvinyl pyrrolidone, molecular weight 7K-11K, a solubilizer (BASF);

Kollidon® K30=polyvinyl pyrrolidone, molecular weight 44K-54K, a solubilizer (BASF);

Labrafil® M2125CS=PEG-6 corn oil, a lipophilic surfactant (Gattefosse);

Labrasol® =PEG-8 caprylic/capric glycerides, a hydrophilic surfactant;

Lutrol® F68=poloxamer 188, a copolymer of 81% PEG and 19% PPG, a hydrophilic surfactant (BASF);

Maisine® 35-1=glyceryl monolinoleate, a lipophilic surfactant (Gattefosse);

Methocel® E3=hydroxypropyl methylcellulose, a delayed release coating material (Dow Chemical);

Miglyol® 812=glyceryl tricaprylate/caprate, a triglyceride composition (Hüls);

Myvacet® 9-45=mono-and diacetylated monoglycerides, a lipophilic surfactant (Eastman); and Vitamin TPGS=d-α-tocopheryl PEG-1000 succinate, a solubilizer (Eastman).

EXAMPLES 1-4

Pharmaceutical suspension formulations containing isotretinoin were prepared containing the components indicated below.

| Composition | (mg) |
| --- | --- |
| Example 1 | |
| Isotretinoin | 40 |
| Soybean Oil | 200 |
| Maisine ® 35-1 | 100 |
| Lutrol ® F68 | 100 |
| Example 2 | |
| Isotretinoin | 40 |
| Labrafil ® M2125CS | 200 |
| Cremophor ® RH40 | 200 |
| Vitamin E TPGS | 100 |
| Example 3 | |
| Isotretinoin | 40 |
| Soybean Oil | 100 |
| Labrafil ® M2125CS | 100 |
| Cremophor ® RH40 | 200 |
| Lutrol ® F68 | 100 |
| Example 4 | |
| Isotretinoin | 40 |
| Miglyol ® 812 | 200 |
| Imwitor ® 742 | 200 |
| Vitamin E TPGS | 400 |
| PEG 3350 | 100 |

In Example 1, the formulation was prepared by admixing soybean oil and Maisine 35-1 and warming the mixture to about 40-50° C. to provide a liquid. Any antioxidant, for example, butylated hydroxyanisole (BHA) or butylated hydroxytoluene (BHT), in an appropriate amount, can be added to the mixture by further raising the temperature of the liquid to about 70° C. and using an appropriate mixer to facilitate dissolution of the antioxidant. The solution of the antioxidant may be cooled to about 40-50° C. or maintained at a higher temperature, for example 70° C. as a liquid. Isotretinoin was stirred into the liquid to give a homogeneous dispersion. To prevent the settling of solid particles of isotretinoin and in order to maintain homogeneity, Lutrol F68 was added. Addition of a chelating agent such as disodium ethylene diamine tetraacetic acid (EDTA) can also be advantageous in this regard. Mixing was continued until the Lutrol F68 was uniformly incorporated and a homogeneous suspension formed. The same procedures were used to prepare the formulations of Examples 2-4.

Alternatively, Lutrol F68 can be first stirred into the oily base of soybean oil and Maisine 35-1 at about 60-70° C. until it is uniformly incorporated. Isotretinoin can then be directly stirred into the mixture to a homogeneous suspension. As another alternative, the isotretinoin can be first dispersed in a fraction of the oily base of soybean oil and Maisine 35-1 prepared as described above, and then stirred into the Lutrol F68 containing mixture. However, it should be appreciated that the order and the extent of mixing and heat of individual component of the composition can be arranged differently to obtain a homogeneous suspension of isotretinoin.

If size reduction of isotretinoin particles is desired, various conventional processes such as grinding, milling, and/or homogenization can be applied to reduce the active agent particle size. The active agent can be size reduced in the absence of soybean oil, Maisine 35-1, and Lutrol F68. The size of the isotretinoin particles can be directly reduced to about 5-30 μm by a high shear homogenizer, such as impeller-type shear mixers from Arde Barinco, Koruma, GEI Krieger and Silverson and wet mills from VMA-Getzmann GMBH and Willy Bachofen AG Maschinenfabrik). Alternatively, the size of the active agent particles can be reduced to about 50-70 μm using a high shear homogenizer. In a two-step size reduction, the size of the isotretinoin can be further reduced to about 5-30 μm subsequently using a liquid jut micronizer, for example, Microfluidizer® by Mirofluidics Corp.

The isotretinoin in Example 3 can be size reduced in the oily base of soybean oil with or without an antioxidant such as BHA. The isotretinoin can also be co-size reduced with the remaining components using the processes described above. The size reduction can be performed at any conventional temperature at which the desired size reduction may be achieved. However, it is preferred to carry out the size reduction in the range of 15-50° C., particularly at room temperature.

EXAMPLES 5-11

Pharmaceutical suspension formulations containing isotretinoin are prepared containing the components indicated below, using the procedures of Examples 1-4.

| Composition | (mg) |
| --- | --- |
| Example 5 | |
| Isotretinoin | 80 |
| Soybean Oil | 200 |
| Maisine ® 35-1 | 100 |
| Lutrol ® F68 | 100 |
| Sodium Lauryl Sulfate | 20 |
| Example 6 | |
| Isotretinoin | 100 |
| Soybean Oil | 200 |
| Maisine ® 35-1 | 100 |
| Lutrol ® F68 | 100 |
| Kollidon ® K30 | 100 |
| Example 7 | |
| Isotretinoin | 40 |
| Maisine ® 35-1 | 400 |
| Gelucire ® 44/14 | 200 |
| Lutrol ® F68 | 100 |
| Example 8 | |
| Isotretinoin | 40 |
| Maisine ® 35-1 | 150 |
| Cremophor ® RH40 | 150 |
| Lutrol ® F68 | 100 |
| Example 9 | |
| Isotretinoin | 40 |
| Labrafil ® M2125CS | 200 |
| Cremophor ® RH40 | 200 |
| Lutrol ® F68 | 100 |
| Example 10 | |
| Isotretinoin | 40 |
| Labrafil ® M1944CS | 150 |
| Cremophor ® RH40 | 100 |
| Gelucire ® 53/13 | 150 |
| Example 11 | |
| Isotretinoin | 40 |
| Glyceryl Cocoate | 100 |
| Lauroglycol FCC | 200 |

| Composition | (mg) |
|---|---|
| Vitamin E TPGS | 350 |
| PEG 3350 | 150 |

EXAMPLE 12

Preparation of dosage forms containing the formulations of Examples 1-11, containing at least 20% solubilized active agent:

The suspension formulations of Examples 1-11 can be processed to provide pharmaceutically acceptable dosage forms containing a sufficient amount of isotretinoin so that a therapeutically effective level of isotretinoin can be achieved in the treated subject upon administration of the dosage form. The compositions can be included in a unit dosage form to provide 5-100 mg of isotretinoin per unit dosage form. A preferred dosage form is a capsule encapsulating the formulation. The capsule shell can be made of any conventional capsule material, e.g., gelatin, starch, or cellulose. The preferred capsule is a soft gelatin capsule. The suspension formulation can be filled into the capsule using conventional filling machines. If a two-piece hard gelatin capsule is used, the filled capsule can be further banded or spray sealed with a sealing solution to prevent leakage of the formulation from the capsule.

EXAMPLE 13

Figure 6:
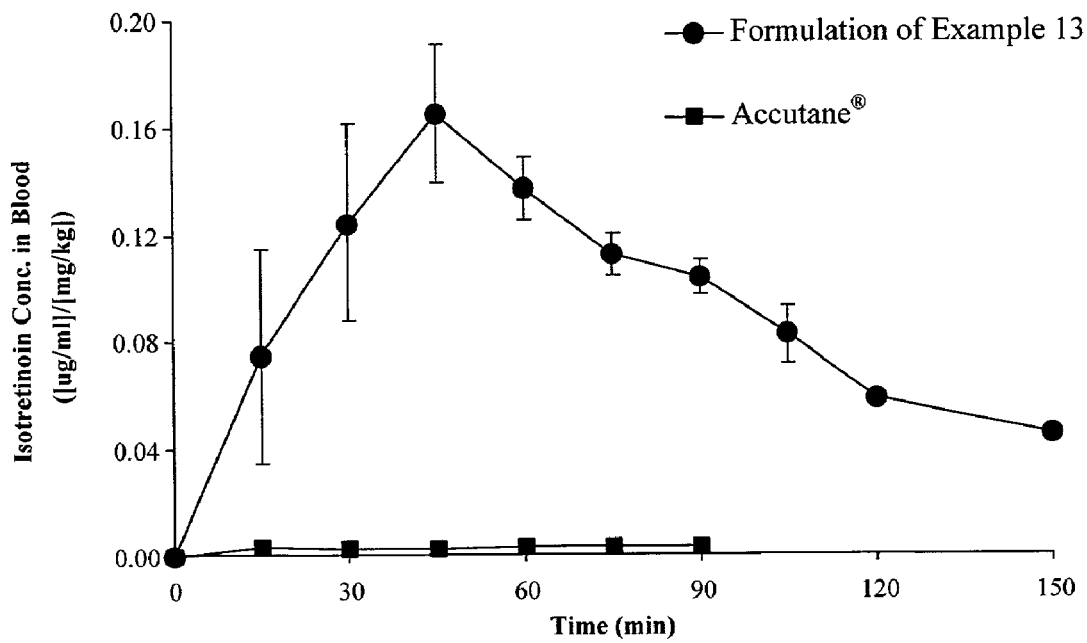
FIG. 6 is a graph comparing the absorption of isotretinoin in rats from a formulation of the invention and from Accutane®, a commercially available isotretinoin product, as evaluated in Example 13.

Absorption of Isotretinoin from the Composition of the Present Invention:

Absorption of isotretinoin from formulations of the present invention was compared with that obtained with a conventional suspension formulation (Accutane®) in rats. The composition of Example 4 (containing at least 20% solubilized isotretinoin) and Accutane® were given to fasted male Sprague-Dawley rats at about 10 mg/kg by intra-duodenum injection followed by infusing Ringer's solution in an amount of about 1% of the animal's body weight at a rate of 0.1 ml/ml. The blood was withdrawn from the rats by heart puncturing at an interval of 15-30 min for at least 90 min. The isotretinoin in the blood samples was extracted by acetonitrile and injected to HPLC for quantitative analysis. The absorption of isotretinoin in rats from the suspension of the invention was found to be significantly better than that from the conventional commercial suspension formulation (wherein less than 10% of the isotretinoin is solubilized), as illustrated in FIG. 6.

EXAMPLES 14-26

Pharmaceutical suspension formulations containing the lipid-regulating agent fenofibrate were prepared containing the components indicated below.

| Composition | (mg) |
|---|---|
| Example 14 | |
| Fenofibrate | 134 |
| Myvacet ® 9-45 | 335 |
| Etocas ® 35 | 335 |
| PEG 3350 | 100 |

| Composition | (mg) |
|---|---|
| Example 15 | |
| Fenofibrate | 135 |
| Myvacet ® 9-45 | 335 |
| Etocas ® 35 | 335 |
| Sodium Lauryl Sulfate | 6 |
| Example 16 | |
| Fenofibrate | 160 |
| Myvacet ® 9-45 | 350 |
| Etocas ® 35 | 350 |
| Sodium Lauryl Sulfate | 20 |
| Water | 20 |
| Example 17 | |
| Fenofibrate | 135 |
| Cremophor ® EL | 280 |
| Labrasol ® | 180 |
| Labrafil ® M2125CS | 280 |
| Glycerol | 10 |
| Propylene Glycol | 25 |
| Example 18 | |
| Fenofibrate | 135 |
| Cremophor ® EL | 280 |
| Labrasol ® | 100 |
| Labrafil ® M2125CS | 280 |
| Lutrol ® F68 | 50 |
| Fumed Silicon Dioxide | 30 |
| Example 19 | |
| Fenofibrate | 135 |
| Cremophor ® EL | 200 |
| Labrasol ® | 120 |
| Labrafil ® M2125CS | 200 |
| Sodium Lauryl Sulfate | 27 |
| Kollidon ® K17 | 50 |
| Example 20 | |
| Fenofibrate | 135 |
| Cremophor ® EL | 200 |
| Labrasol ® | 120 |
| Labrafil ® M2125CS | 200 |
| Methocel ® E3 | 90 |
| Sodium Carboxymethyl-cellulose | 50 |
| Example 21 | |
| Fenofibrate | 100 |
| Cremophor ® RH40 | 150 |
| Labrafil ® M2125CS | 150 |
| Vitamin E TPGS | 150 |
| α-tocopherol | 100 |
| Lutrol ® F68 | 50 |
| Example 22 | |
| Fenofibrate | 90 |
| Etocas ® 35 | 150 |
| Capryol ® 90 | 150 |
| Vitamin E TPGS | 150 |
| Triethyl Citrate | 50 |
| Microcrystalline Cellulose | 100 |
| Example 23 | |
| Fenofibrate | 135 |
| Cremophor ® EL | 240 |
| Labrafil ® M2125CS | 200 |
| Vitamin E TPGS | 240 |
| α-tocopherol | 80 |
| Propylene Glycol | 40 |
| Example 24 | |
| Fenofibrate | 135 |
| Cremophor ® EL | 338 |
| Labrafil ® M2125CS | 187 |
| Labrasol ® | 225 |

-continued

| Composition | (mg) |
|---|---|
| Example 25 | |
| Fenofibrate | 135 |
| Cremophor ® EL | 338 |
| Polysorbate 80 | 187 |
| Labrasol ® | 225 |
| Example 26 | |
| Fenofibrate | 135 |
| Cremophor ® EL | 450 |
| Labrasol ® | 300 |

In Example 14, micronized fenofibrate was dispersed in the mixture of Myvacet 9-45 and Etocas 35, and molten PEG was then added and homogenized to obtain the suspension.

In Example 15, the composition was prepared as follows. 60 mg of fenofibrate was mixed with sodium lauryl sulfate. The resulting powder mixture was added to a Myvacet 9-45/Etocas 35 mixture containing an already solubilized 75 mg of fenofibrate, and the dispersion was homogenized until a homogeneous suspension was obtained. Alternatively, to prepare the suspended fraction of fenofibrate, 60 mg of fenofibrate may be heated to its melting point or slightly above and held as a liquid. Sodium lauryl sulfate may then be added to form a fused mixture, which is then allowed to cool and solidify. As another alternative, the mixture may be prepared by dissolving fenofibrate and sodium lauryl sulfate in a volatile solvent, and subsequently removing the solvent. The resulting solid may be ground into a fine powder for preparing the suspension.

In Example 16, 60 mg of fenofibrate was dissolved in the mixture of Myvacet 9-45 and Etocas 35 to obtain a clear solution. To this solution, 100 mg micronized fenofibrate intimately mixed with sodium lauryl sulfate was added and mixing was continued until a homogenous dispersion was obtained. Water, as a gelling agent, was then introduced to the dispersion and mixed evenly to obtain the final suspension. Similarly in Example 18, to a homogenous dispersion of an intimate mixture of fenofibrate and sodium lauryl sulfate in a solution in which 45 mg of fenofibrate are "predissolved" in a mixture of Cremophor EL, polysorbate 80, Labrasol, and Labrafil M2125CS, aluminum monostearate (a gelling agent) was added and mixed evenly to obtain the final suspension.

In Example 19, 90 mg of fenofibrate was suspended in an aqueous solution of Kollidon K17. The water was removed by spray drying and fenofibrate particles coated with Kollidon K17 were obtained. The coated particles were ground with sodium lauryl sulfate and then suspended in a mixture of Cremophor EL, Labrasol, and Labrafil M2125CS in which 45 mg of fenofibrate was already solubilized, to obtain the final suspension.

Similar procedures were used to prepare the remaining formulations.

EXAMPLES 27-33

Pharmaceutical suspension formulations containing fenofibrate are prepared containing the components indicated below, using the procedures of Examples 14-26.

| Composition | (mg) |
|---|---|
| Example 27 | |
| Fenofibrate | 135 |
| Cremophor ® EL | 280 |
| Labrasol ® | 100 |
| Polysorbate 80 | 80 |
| Labrafil ® M2125CS | 280 |
| Sodium Lauryl Sulfate | 15 |
| Aluminum monostearate | 15 |
| Example 28 | |
| Fenofibrate | 100 |
| Cremophor ® RH40 | 150 |
| Labrafil ® M2125CS | 150 |
| Vitamin E TPGS | 150 |
| α-tocopherol | 100 |
| Magnesium Aluminum Silicate | 50 |
| Example 29 | |
| Fenofibrate | 135 |
| Cremophor ® EL | 180 |
| Labrafil ® M2125CS | 140 |
| Vitamin E TPGS | 180 |
| Kollidon ® K30 | 45 |
| Mannitol | 45 |
| Propylene Glycol | 25 |
| Example 30 | |
| Fenofibrate | 160 |
| Pravastatin | 40 |
| Cremophor ® EL | 250 |
| Polysorbate 80 | 170 |
| Labrafil ® M2125CS | 250 |
| Example 31 | |
| Fenofibrate | 100 |
| Simvastatin | 20 |
| Cremophor ® EL | 200 |
| Vitamin E TPGS | 200 |
| Example 32 | |
| Fenofibrate | 67 |
| Cremophor ® EL | 300 |
| Example 33 | |
| Fenofibrate | 200 |
| α-tocopherol | 500 |

EXAMPLE 34

Preparation of Dosage Forms Containing the Suspension Formulations of Examples 14-33:

The suspension formulations of Examples 14-33 can be processed to provide pharmaceutically acceptable dosage forms containing a sufficient amount of fenofibrate so that a therapeutically effective level of the lipid-regulating agent can be achieved in the treated subject upon administration of the dosage form. The compositions can be included in a unit dosage form to provide 10-200 mg of fenofibrate per unit dosage form. A preferred dosage form is a capsule encapsulating the formulation. The capsule shell can be made of any conventional capsule material, e.g., gelatin, starch, or cellulose. The preferred capsule is a soft gelatin capsule. The suspension formulation can be filled into the capsule using conventional filling machines. If a two-piece hard gelatin capsule is used, the filled capsule can be further banded or spray sealed with a sealing solution to prevent leakage of the formulation from the capsule.

EXAMPLE 35

Figure 7:
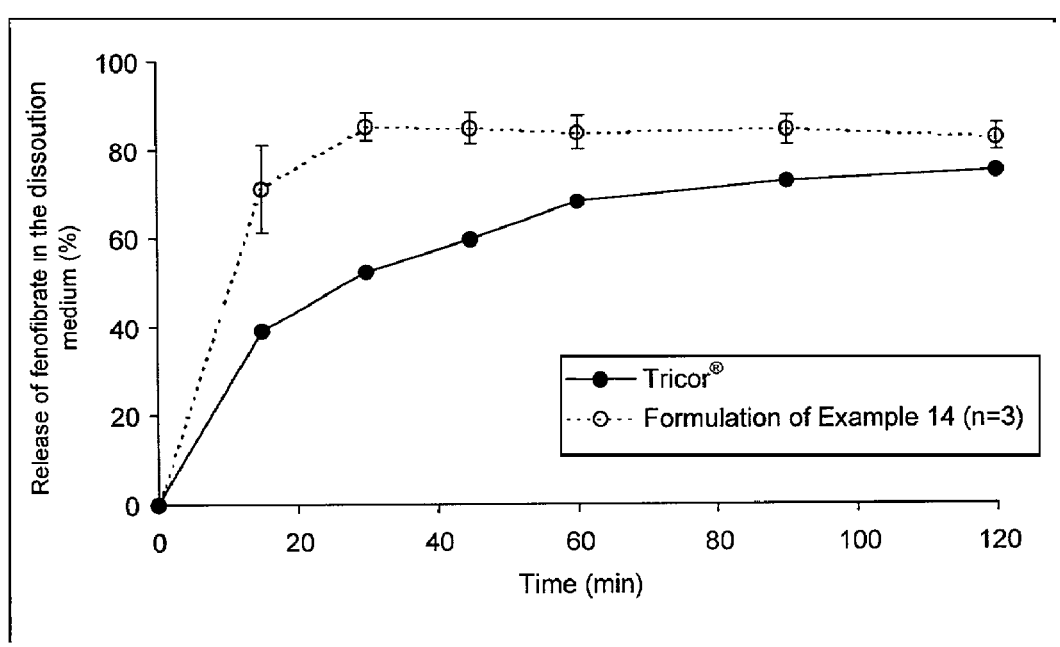
FIG. 7 is a graph illustrating the results of the dissolution tests described in Example 35, with respect to a comparison of the fenofibrate formulation of Example 14 and a commercially available fenofibrate product, Tricor®.
Figure 8:
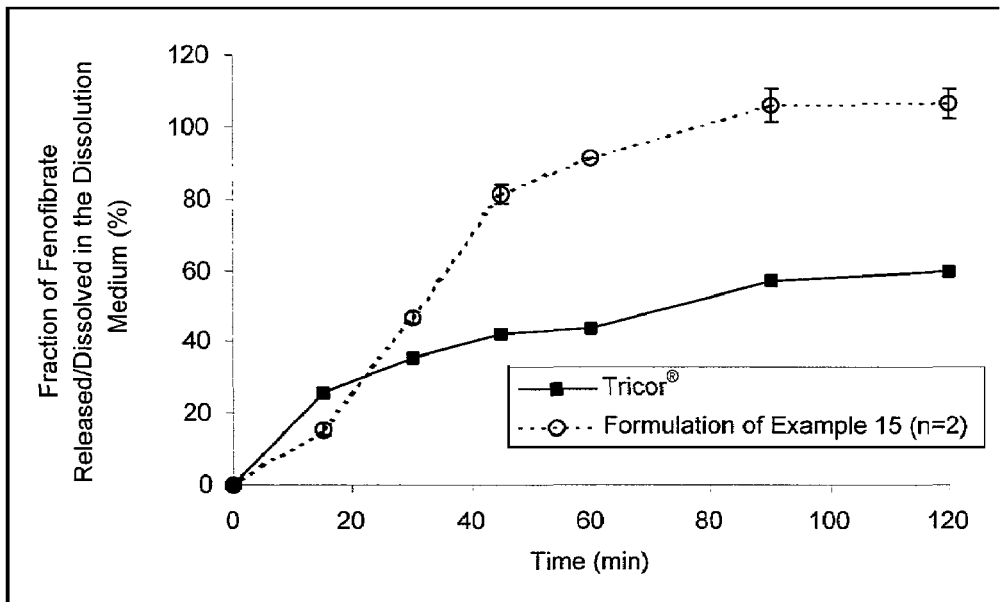
FIG. 8 is a graph illustrating the results of the dissolution tests described in Example 35, with respect to a comparison of the fenofibrate formulation of Example 15 and a commercially available fenofibrate product, Tricor®.

Dissolution of Fenofibrate from the Formulations of the Present Invention:

The fenofibrate formulations of Examples 14 and 15, in which the fraction of solubilized fenofibrate is greater than 30%, were filled into gelatin capsules for a dissolution study to compare the release profile with that of a commercial product, the Tricor® fenofibrate capsule (Abbott). The dissolution study was carried out using a USP type I dissolution apparatus at 100 rpm, 37° C., in 1L of dissolution medium containing SGF and 25 mM sodium lauryl sulfate or 2% Tween 80. One capsule containing 134 mg fenofibrate of Example 14 or Example 15 or two Tricor 67 mg capsules were placed in the basket. At a given time, the dissolution medium was filtered and assayed by HPLC to determine the release of fenofibrate. The dissolution results shown in FIGS. 7 and 8 demonstrate the superior release of fenofibrate from the novel suspension formulation in which a significant fraction of the drug is solubilized in the highly water-dispersible vehicle, in turn facilitating the dissolution of suspended particles. Compared with the commercial product, the rate and the extent of dissolution of fenofibrate from a single capsule of the present invention was found to be superior to that observed two Tricor 67 mg capsules combined.

EXAMPLE 36

Figure 9:
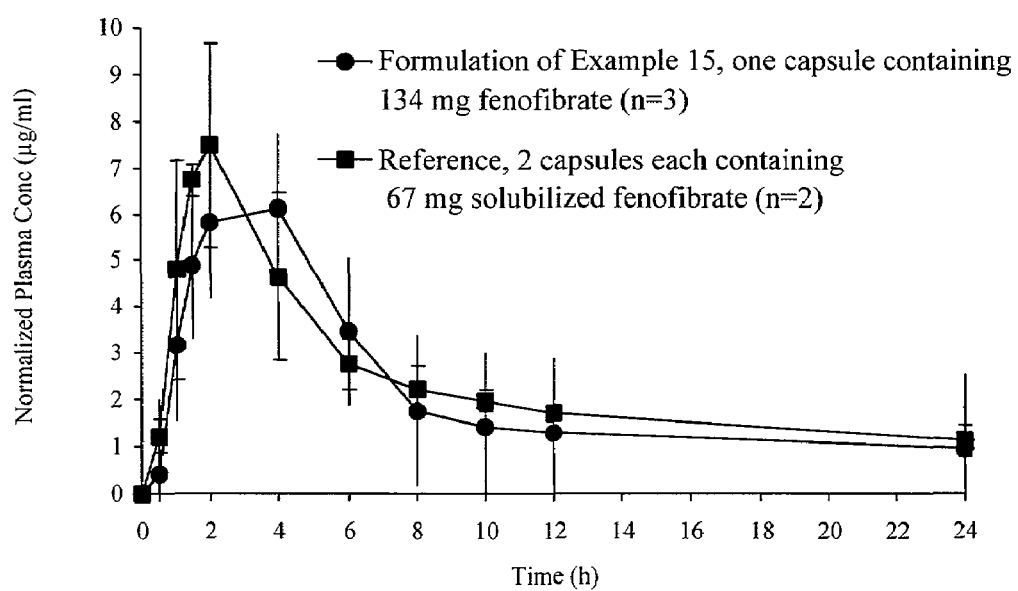
FIG. 9 is a graph illustrating the results of the in vivo absorption tests described in Example 36 for the fenofibrate formulation of Example 15.

Absorption of Fenofibrate from the Formulations of the Present Invention in Dogs:

The absorption of fenofibrate in dogs using suspension formulations of the invention was determined. The capsules prepared in Example 15 were administered to a group of fed Beagle dogs at a dose of 134 mg/dog (one capsule per dog for the composition of Example 15 of the present invention and two capsules for a solubilized formulation). The plasma concentrations of fenofibric acid were determined by HPLC. Concentrations were normalized to a 13.4 mg/kg dose in each dog. FIG. 9 presents the resulting data and indicates that the suspension formulation of the present invention, with a significant fraction of the active ingredient solubilized as a loading dose, is able to provide comparable bioavailability to a completely solubilized formulation at the same dose strength but with only one capsule. This demonstrates the advantage of the present invention being able to increase the drug loading in a single unit dosage form and yet provide sufficient absorption of the active ingredient with only one capsule to improve the patient compliance. From the plasma profile, it also demonstrates that the suspension formulation is able to alleviate the high peak concentration frequently associated with a completely solubilized formulation. This has the potential benefit of reducing the risk of toxicity resulted from the high exposure of certain organs/tissues to the active ingredient by a completely solubilized formulation.

EXAMPLE 37

A pharmaceutical suspension formulation containing progesterone was prepared containing the following components:

| Composition | (mg) |
|---|---|
| Progesterone | 100 |
| Capryol ® 90 | 250 |
| Etocas ® 35 | 250 |
| PEG 3350 | 100 |

Micronized progesterone was dispersed in the mixture of Capryol® 90 and Etocas® 35, and molten PEG was then added and homogenized to provide a suspension. The suspension was heated slightly so that it was fluid enough to be filled into hard gelatin capsules. After filling and cooling at room temperature, the fill material became viscous and incapable of freely flowing ensuring that the formulation would not leak out of the capsule even if the capsule were not to be banded or sealed.

EXAMPLES 38-47

Pharmaceutical suspension formulations containing progesterone and/or estradiol were prepared with the components indicated below.

| Composition | (mg) |
|---|---|
| Example 38 | |
| Progesterone | 100 |
| α-tocopherol | 130 |
| Vitamin E TPGS | 260 |
| Labrafil M2125CS | 230 |
| Propylene Glycol | 90 |
| Cremophor EL | 280 |
| Example 39 | |
| Progesterone | 75 |
| α-tocopherol | 80 |
| Vitamin E TPGS | 240 |
| Labrafil ® M2125CS | 200 |
| Propylene Glycol | 40 |
| Cremophor ® EL | 240 |
| Example 40 | |
| Progesterone | 75 |
| Cremophor ® RH40 | 600 |
| Example 41 | |
| Progesterone | 75 |
| Miglyol ® 812 | 500 |
| Polysorbate 80 | 25 |
| Example 42 | |
| Progesterone | 75 |
| Maisine ® 35-1 | 500 |
| Lutrol ® 68 | 5 |
| Example 43 | |
| Estradiol | 2 |
| Capryl ® 90 | 100 |
| Cremophor ® RH40 | 100 |
| Lactose | 50 |
| Example 44 | |
| Progesterone | 75 |
| Estradiol | 2 |
| PEG 400 | 300 |
| Cremophor ® EL | 200 |
| Example 45 | |
| Progesterone | 50 |
| Estradiol | 2 |
| Vitamin E TPGS | 120 |

-continued

| Composition | (mg) |
|---|---|
| Labrafil ® M2125CS | 200 |
| Cremophor ® EL | 240 |
| Propylene Glycol | 40 |
| Lactose | 50 |
| Example 46 | |
| Progesterone | 75 |
| Estradiol | 1 |
| PEG 400 | 300 |
| Tween 80 | 30 |
| Example 47 | |
| Progesterone | 75 |
| Estradiol | 1 |
| Vitamin E TPGS | 400 |

In Example 38, micronized progesterone is dispersed in a mixture of the remaining components and homogenized to obtain the suspension. The suspension may be heated slightly, as in Example 37, so that it is fluid enough to be filled into hard gelatin capsules.

In Example 41, 1 mg of estradiol mixed with 50 mg of lactose and encapsulated in a small two-piece hard gelatin capsule (size 6) is then further encapsulated in a larger two-piece hard gelatin capsule (size 3) containing the other 1 mg of estradiol solubilized in the mixture of Capryol 90 and Cremophor RH40. Both of the capsules can be sealed or banded to prevent leakage of the fill material, using methods well known in the art.

In Example 43, 2 mg of estradiol and 30 mg of progesterone is mixed with 50 mg of lactose and encapsulated in a small two-piece hard gelatin capsule (size 6), then further encapsulated in a larger two-piece hard gelatin capsule (size 0) that contains the remaining 20 mg of progesterone solubilized in the mixture of α-tocopherol, Labrafil M2125CS, propylene glycol and Cremophor EL. Again, both of the capsules can be sealed or banded to prevent the leakage of the fill material using conventional methods.

The remaining formulations are prepared using similar procedures.

EXAMPLE 48

Preparation of Dosage Forms Containing the Compositions Comprising Suspended Sex Hormone in Examples 37-47:

The suspension formulations of Examples 37-47 can be processed to provide pharmaceutically acceptable dosage forms containing a therapeutically effective amount of at least one sex hormone. The compositions can be included in a unit dosage form to provide 0.5-2 mg of estradiol and/or 25-150 mg of progesterone per unit dosage form. However, the dose and the composition in each formulation can be further adjusted or exchanged with the compositions of other active agents described herein the example section based upon the actual clinical need. A preferred dosage form is a capsule encapsulating the formulation. The capsule shell can be made of any conventional capsule material, e.g., gelatin, starch, or cellulose. The preferred capsule is a soft gelatin capsule. The suspension formulation can be filled into the capsule using conventional filling machines. If a two-piece hard gelatin capsule is used, the filled capsule can be further banded or spray sealed with a sealing solution to prevent leakage of the formulation from the capsule.

EXAMPLE 49

Figure 10:
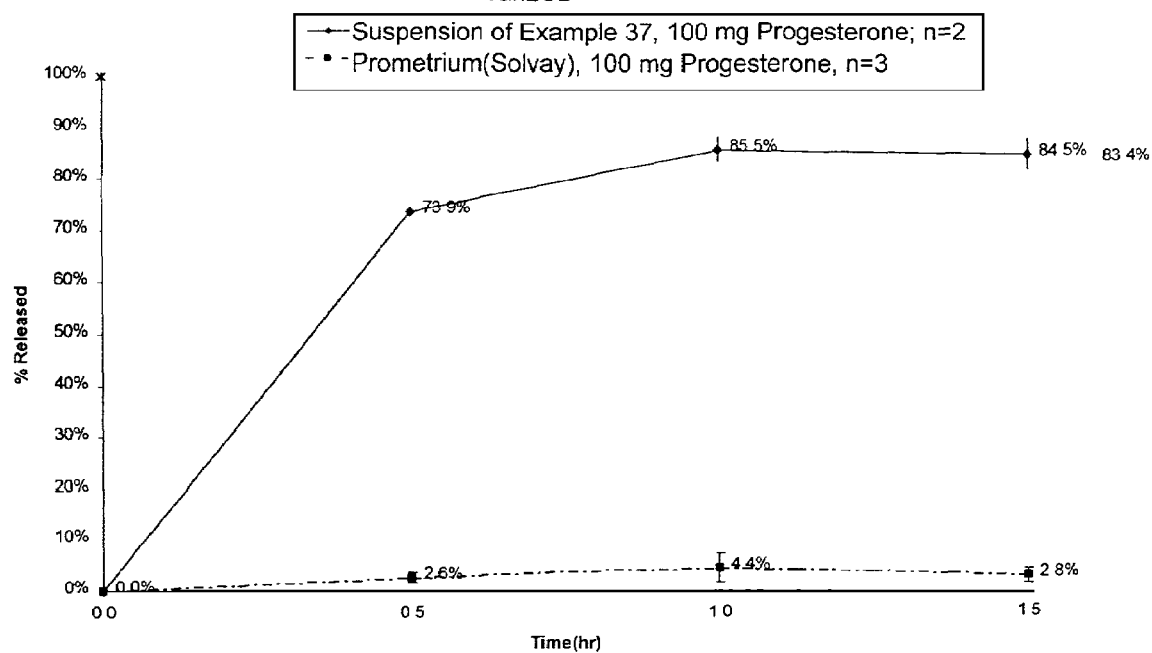
FIG. 10 is a graph illustrating the results of the dissolution tests described in Example 49, with respect to a comparison of the progesterone formulation of Example 37 and a commercially available progesterone suspension, Prometrium®.

Dissolution of Progesterone from the Formulations of the Present Invention:

The formulation prepared based on the composition in Example 37 was filled into a hard gelatin capsule for a dissolution study to compare the release profile with that of a commercial product, Prometrium® (Solvay). The dissolution study was carried out using a USP type I dissolution apparatus at 100 rpm, 37° C., in 1L of dissolution medium containing SGF and 12.5 mM sodium lauryl sulfate. One capsule containing 100 mg progesterone (in the formulation of Example 37) or one Prometrium® 100 mg capsule was placed in the basket. At a given time, the dissolution medium was filtered and assayed by HPLC to determine the release of progesterone. The dissolution results are shown in FIG. 10, and demonstrate the superior release of progesterone from the novel suspension formulation in which a significant fraction of the drug is solubilized in the highly water-dispersible vehicle, in turn facilitating dissolution of suspended particles.

EXAMPLE 50

Figure 11A:
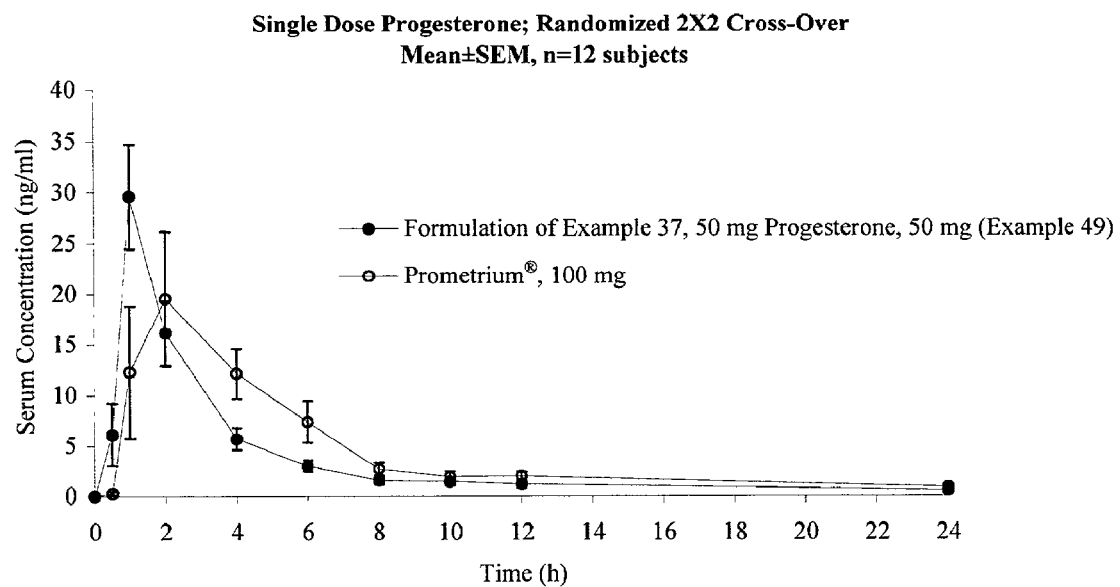
FIGS. 11A and 11B are graphs illustrating the results of the in vivo absorption tests described in Example 50 for the progesterone formulation of Example 37 and a commercially available progesterone suspension, Prometrium®.
Figure 11B:
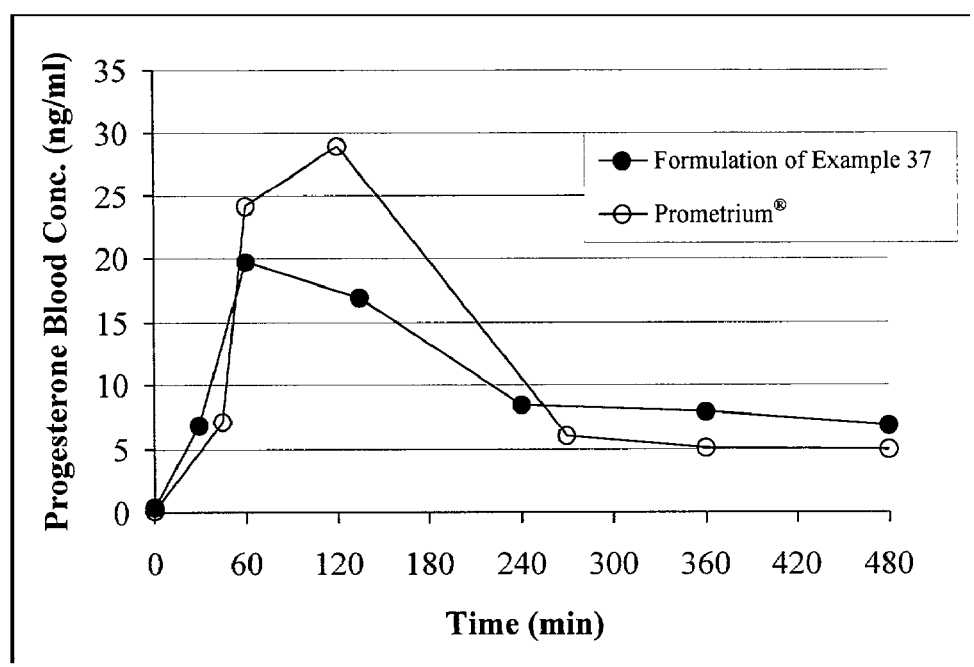

Absorption of Progesterone:

The suspension composition of Example 37 was tested in human volunteers. The crossover study consisted of oral administration of a suspension (that of Example 37), and a commercial product, Prometrium® (Solvay), under fasted condition. For comparison, in a separate study, the formulation of Example 37 (with progesterone greater than 50% solubilized) was dosed (2 capsules of 25 mg of progesterone) in a crossover design with Prometrium®. The plasma concentrations of progesterone were determined by both RIA and a fluorescence method. The resulting progesterone blood concentrations were normalized against 100 mg dose and are summarized in FIGS. 11A and 11B. As can be seen in FIG. 11A, the formulation of Example 37 exhibited a rapid $T_{max}$ and higher $C_{max}$ compared to the commercial product. However, the solubilized formulation plasma levels drop precipitously relative to those of the commercial product. After 2 hours, the plasma levels were below that of the commercial product. FIG. 11B shows that the plasma profile can be modulated with the current invention (Example 37) relative to the commercial product. The peak plasma level ($C_{max}$) is lower and $T_{max}$ occurs earlier than with the commercial product. However, the extended plasma levels remained well above those of the commercial product and can result in sustained activity. Such sustained blood concentration may potentially be beneficial to the therapeutic effect of the active ingredient. It also should be noted that a lower peak plasma concentration of progesterone could also have the advantage of reducing any side effects, such as drowsiness, associated with high plasma concentration of progesterone or its metabolites while not losing the opportunity to sufficiently saturate endometrial receptors to render desirable efficacy. These data exemplify the wide range of plasma profiles that can be achieved with the current invention.

EXAMPLES 51-74

Pharmaceutical suspension formulations containing other active agents are prepared containing the components indicated below.

| Composition | (mg) |
|---|---|
| Example 51 | |
| Modafinil | 200 |
| Labrasol ® | 400 |
| Example 52 | |
| Zolpidem | 10 |
| Capmul ® MCM | 200 |
| Example 53 | |
| Spironolactone | 200 |
| PEG 400 | 600 |
| Example 54 | |
| Celecoxib | 200 |
| Miglyol ® 812 | 240 |
| Example 55 | |
| Zafirlukast | 20 |
| Transcutol ® | 100 |
| Myvacet ® 9-45 | 200 |
| Example 56 | |
| Rofecoxib | 25 |
| Cremophor ® EL | 30 |
| Labrafil ® M2125CS | 60 |
| α-tocopherol | 210 |
| Example 57 | |
| Amprenavir | 150 |
| α-tocopherol | 400 |
| Vitamin E TPGS | 100 |
| Example 58 | |
| Atovaquone | 150 |
| Peceol | 100 |
| Labrafil ® M2125CS | 100 |
| Cremophor ® RH40 | 100 |
| Example 59 | |
| Cilostazol | 100 |
| Cremophor ® EL | 200 |
| Triethyl Citrate | 100 |
| Example 60 | |
| Ursodeoxycholic Acid | 200 |
| Propylene Glycol | 100 |
| Vitamin E TPGS | 300 |
| Example 61 | |
| Thalidomide | 100 |
| Vitamin E TPGS | 200 |
| Transcutol ® | 150 |
| Triacetin | 150 |
| Example 62 | |
| Terbinafine | 100 |
| Olive Oil | 100 |
| Cremophor ® RH40 | 400 |
| Maisine ® 1-35 | 250 |
| Ethanol | 50 |
| Example 63 | |
| Nelfinavir | 200 |
| Tween 80 | 100 |
| Captex ® 810D | 400 |
| Example 64 | |
| Pioglitazone | 10 |
| Lutrol ® 68 | 50 |
| Triethyl Citrate | 50 |
| Propylene Glycol | 50 |
| Example 65 | |
| Zaleplon | 10 |
| Cremophor ® EL | 150 |

-continued

| Composition | (mg) |
|---|---|
| Labrafil ® M2125CS | 80 |
| Labrasol ® | 100 |
| Example 66 | |
| Zaleplon | 10 |
| Cremophor ® EL | 70 |
| Labrafil ® M2125CS | 60 |
| Vitamin E TPGS | 60 |
| Propylene Glycol | 10 |
| Example 67 | |
| Zolpidem | 10 |
| Cremophor ® EL | 100 |
| Labrafil ® M2125CS | 54 |
| Labrasol ® | 30 |
| Propylene Glycol | 10 |
| Example 68 | |
| Zolpidem | 10 |
| Cremophor ® EL | 120 |
| Labrafil ® M2125CS | 100 |
| Vitamin E TPGS | 120 |
| α-tocopherol | 40 |
| Propylene Glycol | 20 |
| Example 69 | |
| Ondansetron | 8 |
| Cremophor ® EL | 250 |
| Labrafil ® M2125CS | 130 |
| Water | 20 |
| Example 70 | |
| Lisinopril | 40 |
| Vitamin E TPGS | 170 |
| PEG 400 | 400 |
| Water | 30 |
| Example 71 | |
| Nifedipine | 60 |
| Cremophor ® RH40 | 420 |
| Imwitor ® 742 | 150 |
| Ethanol | 30 |
| Example 72 | |
| Amiodarone | 200 |
| Transcutol ® | 300 |
| Tween ® 80 | 250 |
| Ethanol | 50 |
| Example 73 | |
| Butorphanol | 20 |
| Cremophor ® EL | 250 |
| Labrafil ® M2125CS | 130 |
| Acetic Acid | 10 |
| Example 74 | |
| Rizatriptan | 10 |
| Vitamin E TPGS | 100 |
| PEG 400 | 100 |
| Water | 5 |

We claim:

1. A pharmaceutical formulation, comprising: (a) fenofibrate having a first fraction and a second fraction, wherein the first fraction is comprised of a plurality of solid particles; and (b) a pharmaceutically acceptable vehicle comprising at least one compound selected front the group consisting of a hydrophilic surfactant, a lipophilic surfactant, a triglyceride and a solubilizer, wherein said formulation is encapsulated in an exterior capsule and the first fraction and the second fraction are segregated the first fraction of the fenofibrate is suspended in the vehicle and the second fraction of the fenobibrate is solubilized in the vehicle, said first fraction representing about 5 wt. % to about 80 wt. % of the total fenofibrate and said second fraction representing about 20 wt. % to about 95 wt. % of the total fenofibrate.

2. The pharmaceutical formulation of claim 1, further including an additional active agent.

3. The pharmaceutical formulation of claim 1, wherein the first fraction represents about 30 wt. % to about 80 wt. % of the fenofibrate, and the second fraction represents about 20 wt. % to about 70 wt. % of the fenofibrate.

4. The pharmaceutical formulation of claim 3, wherein the first fraction represents about 50 wt. % to about 70 wt. % of the fenofibrate, and the second fraction represents about 30 wt. % to about 50 wt. % of the fenofibrate.

5. The pharmaceutical formulation of claim 1, wherein the solid particles are comprised of powder, granules, pellets, beads, or combinations thereof.

6. The pharmaceutical formulation of claim 1, wherein the solid particles are associated with each other to form at least one dosage unit comprised of a granule, pellet, bead or tablet suspended in the vehicle.

7. The pharmaceutical formulation of claim 1, wherein the solid particles are contained within at least one capsule suspended in the vehicle.

8. The pharmaceutical formulation of claim 1, wherein the solid particles are prepared by a process selected from melt extrusion, nanoencapsulation, lyophilization, spheronization, coacervation, cryopelletization, crystallization, antisolvent precipitation, precipitation from expanded supereritical fluid, spray drying, spray coating, spray congealing, and combinations thereof.

9. The pharmaceutical formulation of claim 8, wherein the solid particles are subjected to further processing after preparation thereof.

10. The pharmaceutical formulation of claim 9, wherein the further processing comprises size reduction.

11. The pharmaceutical formulation of claim 10, wherein the size reduction is carried out by a process selected from grinding, milling, micronization, nanosizing, and combination thereof.

12. The pharmaceutical formulation of claim 11, wherein the solid particles have a mean diameter in the range of about 0.1 μm to about 100 μm.

13. The pharmaceutical formulation of claim 10, wherein the size reduction is carried out in the presence of a surfactant, a hydrophilic polymer, a lipid, a gelatin, a saccharide, or a mixture thereof.

14. The pharmaceutical formulation of claim 10, wherein the size reduction is carried out in the presence of the vehicle.

15. The pharmaceutical formulation of claim 1, wherein the solid particles contain at least one pharmaceutically acceptable excipient.

16. The pharmaceutical formulation of claim 1, further comprising at least one pharmaceutically acceptable additive selected from the group consisting of a stabilizing agent, an antioxidant, a bufferant, an antifoaming agent, a detackifier, a preservative, a chelating agent, a viscomodulator, a tonicifier, a flavorant, a colorant, an odorant, an opacifier, a binder, a filler, a plasticizer, a taste-masking agent, a lubricant, and an enzyme inhibitor.

17. The pharmaceutical formulation of claim 16, wherein said at least one pharmaceutically acceptable additive is a stabilizing agent.

18. The pharmaceutical formulation of claim 17, wherein the stabilizing agent is a suspending agent.

19. The pharmaceutical formulation of claim 18, wherein the suspending agent is selected from the group consisting of microcrystalline cellulose, sodium carboxymethylcellulose, powdered cellulose, hydroxypropyl cellulose, hydroxypropyl methylcellulose, methylcellulose, ethylcellulose, ethyl methylcellulose, ethyl hydroxyethylcellulose, attapulgite, bentonite, hectorite, montmorillonita, silica gel, fumed silicon dioxide, colloidal silicon dioxide, acacia, agar, carrageenan, guar gum, locust bean gum, pectin, sodium alginate, propylene glycol alginate, tamarind gum, xanthan gum, carbomers, polyvinyl pyrrolidone, starch, sodium starch glycolate, tragacanth, magnesium aluminum silicate, aluminum silicate, magnesium silicate, gelatin, and glycyrrhizin.

20. The pharmaceutical formulation of claim 1, wherein the solid particles comprise at least one amorphous phase, at least one crystalline phase, or a mixture of at least one amorphous phase and at least one crystalline phase.

21. The pharmaceutical formulation of claim 1, wherein the solid particles further include a stabilizing agent.

22. The pharmaceutical formulation of claim 21, wherein said stabilizing agent is selected from the group consisting of synthetic hydrophilic polymers, surfactants, saccharides, gelatin, and combinations thereof.

23. The pharmaceutical formulation of claim 22, wherein the synthetic hydrophilic polymers are selected from the group consisting of polyalkylene oxides, polyalkylene oxide-substituted $C_2$-$C_6$ diols and triols, polyalkylene oxide-substituted saccharides, poly(N-vinyl lactams), and polymers of carboxyvinyl monomers.

24. The pharmaceutical formulation of claim 23, wherein the synthetic hydrophilic polymers are selected from the group consisting of polyethylene glycol, mono-poly(oxyethylene)-substituted propylene glycol, di-(polyoxyethylene)-substituted propylene glycol, mono-poly(oxyethylene)-substituted glycerol, di-(polyoxyethylene)-substit-uted glycerol, tri-(polyoxyethylene)-substituted glycerol, polyoxyethylated sorbitol, polyoxyethylated glucose, polyvinyl pyrrolidone, poly(N-vinyl caprolactam), and polymers and copolymers of acrylic acid, methacrylic acid and/or esters thereof.

25. The pharmaceutical formulation of claim 22, wherein the saccharides are cellulosic polymers.

26. The pharmaceutical formulation of claim 25, wherein the stabilizing agent is hydroxypropyl methylcellulose.

27. The pharmaceutical formulation of claim 1, wherein the vehicle is substantially free of water-indispersible wax materials.

28. The pharmaceutical formulation of claim 27, wherein the water-indispersible wax materials are selected front the group consisting of beeswax, paraffin, yellow wax, hydrogenated oils, hydrogenated vegetable oil, hydrogenated soybean oil flakes and mixtures thereof.

29. The pharmaceutical formulation of claim 1, wherein the vehicle contains less than about 20 wt. % water.

30. The pharmaceutical formulation of claim 1, wherein the vehicle contains less than about 10 wt. % water.

31. The pharmaceutical formulation of claim 1, wherein the vehicle comprises (a) at least one hydrophilic surfactant, (b) at least one lipophilic surfactant, or (c) at least one hydrophilic surfactant and at least one lipophilic surfactant.

32. The pharmaceutical formulation of claim 31, wherein the vehicle comprises at least one hydrophilic surfactant and at least one lipophilic surfactant.

33. The pharmaceutical formulation of claim 1, wherein the vehicle comprises a triglyceride, a solubilizer, or a mixture thereof.

34. The pharmaceutical formulation of claim 1, wherein said at least one compound represents about 1 wt. % to about 99 wt. % of the formulation.

35. The pharmaceutical formulation of claim 34, wherein said at least one compound represents about 10 wt. % to about 90 wt. % of the formulation.

36. The pharmaceutical formulation of claim 35, wherein said at least one compound represents about 20 wt. % to about 80 wt. % of the formulation.

37. The pharmaceutical formulation of claim 1, wherein either the first fraction of the fenofibrate, the second fraction of the fenofibrate, or both the first and second fractions of the fenofibrate are formulated for immediate release, pulsatile release, controlled release, extended release, delayed release, targeted release, or targeted delayed release of the fenofibrate.

38. The pharmaceutical formulation of claim 37, wherein the first fraction of the fenofibrate and the second fraction of the fenofibrate have different release profiles.

39. The pharmaceutical formulation of claim 37, wherein the first fraction of the fenofibrate further comprises a means for controlling release of the fenofibrate from the suspended particles.

40. The pharmaceutical formulation of claim 39, wherein the second fraction of the fenofibrate comprises an immediate release composition.

41. The pharmaceutical formulation of claim 40, wherein the second fraction of the fenofibrate exhibits an immediate release profile.

42. The pharmaceutical formulation of claim 40, wherein the second fraction provides for release of at least 50% of the fenofibrate contained therein within 30 minutes at 37° C. as evaluated using standard USP dissolution test equipment.

43. The pharmaceutical formulation of claim 42, wherein the second fraction provides for release of at least 75% of the fenofibrate contained therein within 30 minutes at 37° C. as evaluated using standard USP dissolution test equipment.

44. The pharmaceutical formulation of claim 43, wherein the second fraction provides for release of at least 90% of the fenofibrate contained therein within 30 minutes at 37° C. as evaluated using standard USP dissolution test equipment.

45. A dosage form comprising the pharmaceutical formulation of claim 1.

46. A pharmaceutical system for administration of an fenofibrate, comprising: (a) fenofibrate; and (b) a pharmaceutically acceptable vehicle comprising at least one compound selected from the group consisting of a hydrophilic surfactant, a lipophilic surfactant, a triglyceride and a sohtbilizer, wherein the relative amounts of the fenofibrate and the vehicle are such that upon admixture thereof, a first fraction of the fenofibrate is suspended in the vehicle, and a second fraction of the fenofibrate is solubilized in the vehicle, wherein said first and second fractions of are encapsulated in an exterior capsule and the first fraction and the second fraction are segregated, and wherein the second fraction represents about 20 wt. % to about 95 wt. % of the total fenofibrate in the formulation.

47. The pharmaceutical system of claim 46, wherein the first fractidn represents about 10 wt. % to about 80 wt. % of the fenofibrate, and the second fraction represents about 20 wt. % to about 90 wt. % of the fenofibrate.

48. The pharmaceutical system of claim 47, wherein the first fraction represents about 30 wt. % to about 80 wt. % of the fenofibrate, and the second fraction represents about 20 wt. % to about 70 wt. % of the fenofibrate.

49. The pharmaceutical system of claim 48, wherein the first fraction represents about 50 wt. % to about 70 wt. % of the fenofibrate, and the second fraction represents about 30 wt. % to about 50 wt. % of the fenofibrate.

50. The pharmaceutical system of claim 49, wherein the solid particles are comprised of powder, granules, pellets, beads, or combinations thereof.

51. The pharmaceutical system of claim 46, wherein the solid particles are associated with each other to form at least one dosage unit comprised of a granule, pellet, bead or tablet.

52. The pharmaceutical system of claim 51, wherein the solid particles are contained within a capsule.

53. The pharmaceutical system of claim 51, wherein the solid particles are prepared by a process selected from melt extrusion, nanoencapsulation, lyophilization, spheronization, coacervation, cryopelletization, crystallization, antisolvent precipitation, precipitation from expanded supercritical fluid, spray drying, spray coating, spray congealing, and combinations thereof.

54. The pharmaceutical system of claim 53, wherein the solid particles are subjected to further processing after preparation thereof.

55. The pharmaceutical system of claim 54, wherein the further processing comprises size reduction.

56. The pharmaceutical system of claim 55, wherein the size reduction is carried out by a process selected from grinding, milling, micronization; nanosizing, and combination thereof.

57. The pharmaceutical system of claim 56, wherein the solid particles have a mean diameter in the range of about 0.1 µm to about 100 µm.

58. The pharmaceutical system of claim 55, wherein the size reduction is carried out in the presence of a surfactant, a hydrophilic polymer, a lipid, a gelatin, a saccharide, or a mixture thereof.

59. The pharmaceutical system of claim 55, wherein the size reduction is carried out in the presence of the vehicle.

60. The pharmaceutical system of claim 46, wherein the solid particles contain at least one pharmaceutically acceptable excipient.

61. The pharmaceutical system of claim 46, wherein the vehicle further comprises at least one pharmaceutically acceptable additive selected from the group consisting of a stabilizing agent, an antioxidant, a bufferant, an antifoaming agent, a detackifier, a preservative, a chelating agent, a viscomodulator, a tonicifier, a flavorant, a colorant, an odorant, an opacifier, a binder, a filler, a plasticizer, a taste-masking agent, a lubricant, and an enzyme inhibitor.

62. The pharmaceutical system of claim 61, wherein said at least one pharmaceutically acceptable additive is a stabilizing agent.

63. The pharmaceutical system of claim 62, wherein the stabilizing agent is a suspending agent.

64. The pharmaceutical system of claim 63, wherein the suspending agent is selected from the group consisting of microcrystalline cellulose, sodium carboxymethylcellulose, powdered cellulose, hydroxypropyl cellulose, hydroxypropyl methylcellulose, methylcellulose, ethylcellulose, ethyl methylcellulose ethyl hydroxyethylcellulose, attapulgite, bentonire, hectorite, montmorillonite, silica gel, fumed silicon dioxide, colloidal silicon dioxide, acacia, agar, carrageenan, guar gum, locust bean gum, pectin, sodium alginate, propylene glycol alginate, tamarind gum, xanthan gum, carbomers, polyvinyl pyrrolidone, starch, sodium starch glycolate, tragacanth, magnesium aluminum silicate, aluminum silicate, magnesium silicate, gelatin, and glycyrrhizin.

65. The pharmaceutical system of claim 46, wherein the solid particles comprise at least one amorphous phase, at least one crystalline phase, or a mixture of at least one amorphous phase and at least one crystalline phase.

66. The pharmaceutical system of claim 65, wherein the solid particles further include a stabilizing agent.

67. The pharmaceutical system of claim 66, wherein said stabilizing agent is selected from the group consisting of synthetic hydrophilic polymers, surfactans, saccharides, gelatin, and combinations thereof.

68. The pharmaceutical system of claim 67, wherein the synthetic hydrophilic polymers are selected from the group consisting of polyalkylene oxides, polyalkylene oxide-substituted $C_2$-$C_6$ diols and triols, polyalkylene oxide-substituted saccharides, poly(N-vinyl lactams), and polymers of carboxyvinyl monomers.

69. The pharmaceutical system of claim 68, wherein the synthetic hydrophilic polymers are selected from the group consisting of polyethylene glycol, mono-poly(oxyethylene)-substituted propylene glycol, di-(polyoxyethylene)-substituted propylene glycol, mono-poly(oxyethylene)-substituted glycerol, di-(polyoxyethylene)-substit-uted glycerol, tri-(polyoxyethylene)-substituted glycerol, polyoxyethylated sorbitol, polyoxyethylated glucose, polyvinyl pyrrolidone, poly(N-vinyl caprolactam), and polymers and copolymers of acrylic acid, methacrylic acid and/or esters thereof.

70. The pharmaceutical system of claim 69, wherein the saccharides are cellulosic polymers.

71. The pharmaceutical system of claim 70, wherein the stabilizing agent is hydroxypropyl methylcellulose.

72. The pharmaceutical system of claim 46, wherein the vehicle is substantially free of water-indispersible wax materials.

73. The pharmaceutical system of claim 72, wherein the water-indispersible wax materials are selected from the group consisting of beeswax, paraffin, yellow wax, hydrogenated oils, hydrogenated vegetable oil, hydrogenated soybean oil flakes and mixtures thereof.

74. The pharmaceutical system of claim 46, wherein the vehicle contains less than about 20 wt. % water.

75. The pharmaceutical system of claim 74, wherein the vehicle contains less than about 10 wt. % water.

76. The pharmaceutical system of claim 46, wherein the vehicle comprises (a) at least one hydrophilic surfactant, (b) at least one lipophilic surfactant, or (c) at least one hydrophilic surfactant and at least one lipophilic surfactant.

77. The pharmaceutical system of claim 76, wherein the vehicle comprises at least one hydrophilic surfactant and at least one lipophilic surfactant.

78. The pharmaceutical system of claim 46, wherein the vehicle comprises a triglyceride, a solubilizer, or a mixture thereof.

79. The pharmaceutical system of claim 46, wherein either the first fraction of the fenofibrate, the second fraction of the fenofibrate, or both the first and second fractions of the fenofibrate are formulated for immediate release, pulsatile release, controlled release, extended release, delayed release, targeted release, or targeted delayed release of the fenofibrate.

80. The pharmaceutical system of claim 79, wherein the first fraction of the agent and the second fraction of the fenofibrate have different release profiles.

81. The pharmaceutical system of claim 79, wherein the first fraction of the fenofibrate further comprises a means for controlling release of the fenofibrate from the suspended particles.

82. The pharmaceutical system of claim 81, wherein the second fraction of the fenofibrate comprises an immediate release composition.

83. The pharmaceutical system of claim 81, wherein the second fraction of the fenofibrate exhibits an immediate release profile.

84. The pharmaceutical system of claim 83, wherein the second fraction provides for release of at least 50% of the fenofibrate contained therein within 30 minutes at 37° C. as evaluated using standard USP dissolution test equipment.

85. The pharmaceutical system of claim 84, wherein the second fraction provides for release of at least 75% of the fenofibrate contained therein within 30 minutes at 37° C. as evaluated using standard USP dissolution test equipment.

86. The pharmaceutical system of claim 85, wherein the second fraction provides for release of at least 90% of the fenofibrate contained therein within 30 minutes at 37° C. as evaluated using standard USP dissolution test equipment.

* * * * *